United States Patent
De La Huerga

(10) Patent No.: US 9,750,872 B2
(45) Date of Patent: Sep. 5, 2017

(54) METHOD AND APPARATUS FOR CONTROLLING AN INFUSION PUMP OR THE LIKE

(75) Inventor: Carlos A. De La Huerga, Milwaukee, WI (US)

(73) Assignee: B. BRAUN MEDICAL INC., Bethlehem, PA (US)

(*) Notice: Subject to any disclaimer, the term of this patent is extended or adjusted under 35 U.S.C. 154(b) by 1198 days.

(21) Appl. No.: 13/085,670

(22) Filed: Apr. 13, 2011

(65) Prior Publication Data

US 2011/0196306 A1  Aug. 11, 2011

Related U.S. Application Data

(63) Continuation of application No. 10/004,941, filed on Dec. 3, 2001, now Pat. No. 7,933,780, which is a
(Continued)

(51) Int. Cl.
*A61B 5/00* (2006.01)
*A61M 5/142* (2006.01)
(Continued)

(52) U.S. Cl.
CPC .... *A61M 5/14212* (2013.01); *A61M 5/16827* (2013.01); *G06F 19/3468* (2013.01); *G06Q 50/22* (2013.01); *G06Q 50/24* (2013.01); *A61J 2205/10* (2013.01); *A61J 2205/30* (2013.01); *A61J 2205/60* (2013.01); *A61J 2205/70* (2013.01); *A61M 37/00* (2013.01); *A61M 2205/3561* (2013.01);
(Continued)

(58) Field of Classification Search
CPC ........ G06C 50/00; A61M 31/00; A61M 37/00

USPC ............. 235/375; 434/236; 604/131, 65, 67, 604/500; 700/214; 702/114
See application file for complete search history.

(56) References Cited

U.S. PATENT DOCUMENTS 3,227,127 A   1/1966   Gayle
3,762,601 A   10/1973  McLaughlin
(Continued)

FOREIGN PATENT DOCUMENTS

EP   0372692 A2   6/1990
EP   0672427      9/1995
(Continued)

OTHER PUBLICATIONS

"Computer-Assisted Continuous Infusion of the Intravenous Analgesic Fentanyl During General Anesthesia—An Interactive System", Reves et al., vol. BME-32, May 5, 1985, pp. 323-329.
(Continued)

*Primary Examiner* — Dilek B Cobanoglu
(74) *Attorney, Agent, or Firm* — RatnerPrestia

(57) ABSTRACT

A method and apparatus for controlling IV medication delivery and monitoring, the method including providing information tags on IV bags that specify delivery parameters, obtaining delivery parameters for at least one bag, associating a controller with a particular patient, comparing patient information for the particular patient with the delivery parameters, determining the efficacy of delivering the medicant to the patient and affecting pump control as a function of the comparison. The method also includes various timing rules and other verification procedures.

26 Claims, 30 Drawing Sheets

Related U.S. Application Data continuation-in-part of application No. 09/426,553, filed on Oct. 22, 1999, now Pat. No. 7,216,802, and a continuation-in-part of application No. 09/832,770, filed on Apr. 11, 2001, now Pat. No. 7,978,564, and a continuation-in-part of application No. 09/833,358, filed on Apr. 12, 2001, now Pat. No. 6,838,163.

(51) Int. Cl.
- A61M 5/168 (2006.01)
- G06Q 50/22 (2012.01)
- G06Q 50/24 (2012.01)
- A61M 37/00 (2006.01)
- G06F 19/00 (2011.01)

(52) U.S. Cl.
CPC .............. A61M 2205/3569 (2013.01); A61M 2205/3592 (2013.01); A61M 2205/60 (2013.01); A61M 2205/6063 (2013.01); A61M 2205/6072 (2013.01); G06F 19/323 (2013.01)

(56) References Cited

U.S. PATENT DOCUMENTS

| | | |
|---|---|---|
| 4,094,561 A | 6/1978 | Wolff et al. |
| 4,207,992 A | 6/1980 | Brown |
| 4,282,872 A | 8/1981 | Franetzki et al. |
| 4,360,125 A | 11/1982 | Martindale et al. |
| 4,368,988 A | 1/1983 | Tahara et al. |
| 4,384,288 A | 5/1983 | Walton |
| 4,437,579 A | 3/1984 | Obland |
| 4,476,381 A | 10/1984 | Rubin |
| 4,483,626 A | 11/1984 | Noble |
| 4,504,153 A | 3/1985 | Schollmeyer et al. |
| 4,526,404 A | 7/1985 | Vazquez |
| 4,526,474 A | 7/1985 | Simon |
| 4,546,901 A | 10/1985 | Buttarazzi |
| 4,560,979 A | 12/1985 | Rosskopf |
| 4,573,606 A | 3/1986 | Lewis et al. |
| 4,573,994 A | 3/1986 | Fischell et al. |
| 4,575,621 A | 3/1986 | Dreifus |
| 4,598,275 A | 7/1986 | Ross et al. |
| 4,616,316 A | 10/1986 | Hanpeter et al. |
| 4,617,557 A | 10/1986 | Gordon |
| 4,626,105 A | 12/1986 | Miller |
| 4,664,289 A | 5/1987 | Shimizu et al. |
| 4,674,651 A | 6/1987 | Scidmore et al. |
| 4,674,652 A | 6/1987 | Aten et al. |
| 4,694,284 A | 9/1987 | Leveille et al. |
| 4,695,954 A | 9/1987 | Rose et al. |
| 4,696,671 A | 9/1987 | Epstein et al. |
| 4,705,506 A | 11/1987 | Archibald |
| 4,717,261 A | 1/1988 | Kita et al. |
| 4,725,997 A | 2/1988 | Urquhart et al. |
| 4,730,849 A | 3/1988 | Siegel |
| 4,732,411 A | 3/1988 | Siegel |
| 4,733,362 A | 3/1988 | Haraguchi |
| 4,733,797 A | 3/1988 | Haber |
| 4,741,732 A | 5/1988 | Crankshaw et al. |
| 4,741,736 A | 5/1988 | Brown |
| 4,756,706 A | 7/1988 | Kerns et al. |
| 4,785,969 A | 11/1988 | McLaughlin |
| 4,811,764 A | 3/1989 | McLaughlin |
| 4,817,050 A | 3/1989 | Komatsu et al. |
| 4,823,982 A | 4/1989 | Aten et al. |
| 4,828,545 A | 5/1989 | Epstein et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,857,713 A | 8/1989 | Brown |
| 4,857,716 A * | 8/1989 | Gombrich et al. ............ 235/375 |
| 4,865,584 A | 9/1989 | Epstein et al. |
| 4,885,571 A | 12/1989 | Pauley et al. |
| 4,898,578 A | 2/1990 | Rubalcaba, Jr. |
| 4,911,327 A | 3/1990 | Shepherd et al. |
| 4,916,441 A | 4/1990 | Gombrich |
| 4,925,444 A | 5/1990 | Orkin et al. |
| 4,939,705 A | 7/1990 | Hamilton et al. |
| 4,952,928 A | 8/1990 | Carroll et al. |
| 4,953,745 A | 9/1990 | Rowlett, Jr. |
| 4,967,928 A | 11/1990 | Carter |
| 4,971,221 A | 11/1990 | Urquhart et al. |
| 4,973,944 A | 11/1990 | Maletta |
| 4,978,335 A | 12/1990 | Arthur, III |
| 4,980,671 A | 12/1990 | McCurdy |
| 4,984,709 A | 1/1991 | Weinstein |
| 5,006,699 A | 4/1991 | Felkner et al. |
| 5,012,229 A | 4/1991 | Lennon et al. |
| 5,014,875 A | 5/1991 | McLaughlin et al. |
| 5,032,823 A | 7/1991 | Bower et al. |
| 5,041,086 A | 8/1991 | Koenig et al. |
| 5,047,948 A | 9/1991 | Turner |
| 5,048,870 A | 9/1991 | Mangini et al. |
| 5,071,168 A | 12/1991 | Shamos |
| 5,075,670 A | 12/1991 | Bower et al. |
| 5,078,683 A | 1/1992 | Sancoff et al. |
| 5,088,056 A | 2/1992 | McIntosh et al. |
| 5,094,829 A | 3/1992 | Krivak et al. |
| 5,099,463 A | 3/1992 | Lloyd et al. |
| 5,100,380 A | 3/1992 | Epstein et al. |
| 5,104,374 A | 4/1992 | Bishko et al. |
| 5,108,367 A | 4/1992 | Epstein et al. |
| 5,115,223 A | 5/1992 | Moody |
| 5,153,827 A | 10/1992 | Coutre et al. |
| 5,161,199 A | 11/1992 | David |
| 5,166,498 A | 11/1992 | Neeley |
| 5,171,977 A | 12/1992 | Morrison |
| 5,176,285 A | 1/1993 | Shaw |
| 5,181,189 A | 1/1993 | Hafner |
| 5,193,855 A | 3/1993 | Shamos |
| 5,202,929 A | 4/1993 | Lemelson |
| 5,204,670 A | 4/1993 | Stinton |
| 5,207,642 A | 5/1993 | Orkin et al. |
| 5,208,762 A | 5/1993 | Charhut et al. |
| 5,213,232 A | 5/1993 | Kraft et al. |
| 5,233,571 A | 8/1993 | Wirtschafter |
| 5,233,658 A | 8/1993 | Bianco et al. |
| 5,256,157 A | 10/1993 | Samiotes et al. |
| 5,272,318 A | 12/1993 | Gorman |
| 5,273,318 A | 12/1993 | Nakayama et al. |
| 5,289,157 A | 2/1994 | Rudick et al. |
| 5,291,399 A | 3/1994 | Chaco |
| 5,313,439 A | 5/1994 | Albeck |
| 5,317,506 A * | 5/1994 | Coutre et al. ............ 604/65 |
| 5,319,363 A | 6/1994 | Welch et al. |
| 5,319,711 A | 6/1994 | Servi |
| 5,337,919 A | 8/1994 | Spaulding et al. |
| 5,338,157 A | 8/1994 | Biomquist |
| 5,347,453 A | 9/1994 | Maestre |
| 5,348,061 A | 9/1994 | Riley et al. |
| 5,376,070 A | 12/1994 | Purvis et al. |
| 5,378,231 A | 1/1995 | Johnson et al. |
| 5,381,487 A | 1/1995 | Shamos |
| 5,383,858 A | 1/1995 | Reilly et al. |
| 5,392,952 A | 2/1995 | Bowden |
| 5,398,220 A | 3/1995 | Barker |
| 5,401,059 A | 3/1995 | Ferrario |
| 5,405,048 A | 4/1995 | Rogers et al. |
| 5,408,443 A | 4/1995 | Weinberger |
| 5,408,655 A | 4/1995 | Oren et al. |
| 5,412,372 A | 5/1995 | Parkhurst et al. |
| 5,429,602 A | 7/1995 | Hauser |
| 5,431,299 A | 7/1995 | Brewer et al. |
| 5,445,621 A | 8/1995 | Poli et al. |
| 5,458,123 A | 10/1995 | Unger |
| 5,460,294 A | 10/1995 | Williams |
| 5,465,082 A | 11/1995 | Chaco |
| 5,472,113 A | 12/1995 | Shaw |
| 5,477,511 A | 12/1995 | Englehardt |
| 5,480,062 A | 1/1996 | Rogers et al. |
| 5,485,408 A | 1/1996 | Blomquist |

(56) References Cited

U.S. PATENT DOCUMENTS

| | | |
|---|---|---|
| 5,491,482 A | 2/1996 | Dingwall et al. |
| 5,491,774 A | 2/1996 | Norris et al. |
| 5,493,805 A | 2/1996 | Pennuela et al. |
| 5,499,626 A | 3/1996 | Willham et al. |
| 5,502,445 A | 3/1996 | Dingwall et al. |
| 5,502,944 A | 4/1996 | Kraft et al. |
| 5,504,474 A | 4/1996 | Libman et al. |
| 5,508,499 A | 4/1996 | Ferrario |
| 5,511,000 A | 4/1996 | Kaloi et al. |
| 5,512,879 A | 4/1996 | Stokes |
| 5,512,880 A | 4/1996 | Abrams et al. |
| 5,519,808 A | 5/1996 | Benton, Jr. et al. |
| 5,522,525 A | 6/1996 | McLaughlin et al. |
| 5,522,798 A | 6/1996 | Johnson et al. |
| 5,525,969 A | 6/1996 | LaDue |
| 5,527,289 A | 6/1996 | Foster et al. |
| 5,531,679 A | 7/1996 | Schulman et al. |
| 5,531,697 A | 7/1996 | Olsen et al. |
| 5,531,698 A | 7/1996 | Olsen |
| 5,532,705 A | 7/1996 | Hama |
| 5,536,084 A | 7/1996 | Curtis et al. |
| 5,541,580 A | 7/1996 | Gerston et al. |
| 5,541,583 A | 7/1996 | Mandelbaum |
| 5,547,470 A | 8/1996 | Johnson et al. |
| 5,548,566 A | 8/1996 | Barker |
| 5,548,660 A | 8/1996 | Lemelson |
| 5,558,638 A | 9/1996 | Evers et al. |
| 5,558,640 A | 9/1996 | Pfeiler et al. |
| 5,564,005 A | 10/1996 | Weber et al. |
| 5,564,803 A | 10/1996 | McDonald et al. |
| 5,569,187 A | 10/1996 | Kaiser |
| 5,573,506 A | 11/1996 | Vasko |
| 5,582,593 A | 12/1996 | Hultman |
| 5,593,267 A | 1/1997 | McDonald et al. |
| 5,594,786 A | 1/1997 | Chaco et al. |
| 5,602,963 A | 2/1997 | Bissonnette et al. |
| 5,609,268 A | 3/1997 | Shaw |
| 5,609,716 A | 3/1997 | Mosher, Jr. |
| 5,612,675 A | 3/1997 | Jennings et al. |
| 5,621,384 A | 4/1997 | Crimmins et al. |
| 5,623,242 A | 4/1997 | Dawson, Jr. et al. |
| 5,627,520 A | 5/1997 | Grubbs et al. |
| 5,629,981 A | 5/1997 | Nerlikar |
| 5,642,906 A | 7/1997 | Foote et al. |
| 5,643,212 A | 7/1997 | Coutre et al. |
| 5,646,912 A | 7/1997 | Cousin |
| 5,647,854 A | 7/1997 | Olsen et al. |
| 5,650,766 A | 7/1997 | Burgmann |
| 5,651,775 A | 7/1997 | Walker et al. |
| 5,658,250 A | 8/1997 | Blomquist et al. |
| 5,659,741 A | 8/1997 | Eberhardt |
| 5,660,176 A | 8/1997 | Lliff |
| 5,664,270 A | 9/1997 | Bell et al. |
| 5,669,877 A | 9/1997 | Blomquist |
| 5,678,925 A | 10/1997 | Garmaise et al. |
| 5,681,285 A | 10/1997 | Ford et al. |
| 5,687,717 A | 11/1997 | Halpern et al. |
| 5,689,229 A | 11/1997 | Chaco et al. |
| 5,689,567 A | 11/1997 | Miyauchi |
| 5,713,350 A | 2/1998 | Yokota et al. |
| 5,713,856 A | 2/1998 | Eggers et al. |
| 5,719,761 A | 2/1998 | Gatti et al. |
| RE35,743 E | 3/1998 | Pearson |
| 5,732,401 A | 3/1998 | Conway |
| 5,738,102 A | 4/1998 | Lemelson |
| 5,742,233 A | 4/1998 | Hoffman et al. |
| 5,745,366 A | 4/1998 | Higham et al. |
| 5,764,159 A | 6/1998 | Neftel |
| 5,768,813 A | 6/1998 | Reboul et al. |
| 5,771,001 A | 6/1998 | Cobb |
| 5,772,635 A | 6/1998 | Dastur et al. |
| 5,781,442 A * | 7/1998 | Engleson et al. ............ 700/214 |
| 5,782,805 A | 7/1998 | Meinzer et al. |
| 5,793,290 A | 8/1998 | Eagleson et al. |
| 5,807,336 A * | 9/1998 | Russo et al. ................ 604/131 |
| 5,814,015 A | 9/1998 | Gargano et al. |
| 5,822,544 A | 10/1998 | Chaco et al. |
| 5,826,217 A | 10/1998 | Lerner |
| 5,827,180 A | 10/1998 | Goodman |
| 5,833,599 A | 11/1998 | Schrier et al. |
| 5,839,836 A | 11/1998 | Yuyama et al. |
| 5,851,186 A | 12/1998 | Wood et al. |
| 5,852,590 A | 12/1998 | De La Huerga |
| 5,852,911 A | 12/1998 | Yuyama et al. |
| 5,855,395 A | 1/1999 | Foote et al. |
| 5,856,929 A * | 1/1999 | McClendon et al. ......... 702/114 |
| 5,868,669 A | 2/1999 | Lliff |
| 5,871,465 A * | 2/1999 | Vasko ............................ 604/65 |
| 5,877,675 A | 3/1999 | Rebstock et al. |
| 5,877,742 A | 3/1999 | Klink |
| 5,882,338 A | 3/1999 | Gray |
| 5,883,370 A | 3/1999 | Walker et al. |
| 5,883,576 A | 3/1999 | De La Huerga |
| 5,885,245 A | 3/1999 | Lynch et al. |
| 5,895,371 A | 4/1999 | Levitas et al. |
| 5,924,074 A | 7/1999 | Evans |
| 5,936,529 A | 8/1999 | Reisman et al. |
| 5,941,846 A | 8/1999 | Duffy et al. |
| 5,945,651 A | 8/1999 | Chorosinski et al. |
| 5,954,700 A | 9/1999 | Kovelman |
| 5,959,529 A | 9/1999 | Kail, IV |
| 5,960,085 A | 9/1999 | De La Huerga |
| 5,970,388 A | 10/1999 | Will |
| 5,979,757 A | 11/1999 | Tracy et al. |
| 5,980,501 A | 11/1999 | Gray |
| 5,997,476 A | 12/1999 | Brown |
| 6,003,006 A | 12/1999 | Colella et al. |
| 6,012,034 A | 1/2000 | Hamparian et al. |
| 6,012,088 A | 1/2000 | Li et al. |
| 6,019,745 A | 2/2000 | Gray |
| 6,021,392 A | 2/2000 | Lester et al. |
| 6,024,539 A | 2/2000 | Blomquist |
| 6,032,155 A | 2/2000 | de la Huerga |
| 6,032,676 A | 3/2000 | Moore |
| 6,036,231 A | 3/2000 | Foote et al. |
| 6,053,887 A * | 4/2000 | Levitas et al. ................ 604/500 |
| 6,070,148 A | 5/2000 | Mori et al. |
| 6,070,761 A | 6/2000 | Bloom et al. |
| 6,076,106 A | 6/2000 | Hammer et al. |
| 6,104,295 A | 8/2000 | Gaisser et al. |
| 6,110,152 A | 8/2000 | Kovelman |
| 6,113,554 A | 9/2000 | Gilcher et al. |
| 6,140,936 A | 10/2000 | Armstrong |
| 6,144,303 A | 11/2000 | Federman |
| 6,169,707 B1 | 1/2001 | Newland |
| 6,195,589 B1 | 2/2001 | Ketcham |
| 6,215,992 B1 | 4/2001 | Howell et al. |
| 6,219,587 B1 | 4/2001 | Ahlin et al. |
| 6,224,057 B1 | 5/2001 | Morton |
| 6,241,704 B1 | 6/2001 | Peterson et al. |
| 6,255,951 B1 | 7/2001 | De La Huerga |
| 6,259,355 B1 | 7/2001 | Chaco et al. |
| 6,259,654 B1 | 7/2001 | De La Huerga |
| 6,263,330 B1 | 7/2001 | Bessette |
| 6,270,455 B1 | 8/2001 | Brown |
| 6,283,761 B1 * | 9/2001 | Joao ............................ 434/236 |
| 6,286,038 B1 | 9/2001 | Reichmeyer et al. |
| 6,294,999 B1 | 9/2001 | Yarin et al. |
| 6,295,506 B1 | 9/2001 | Heinonen et al. |
| 6,312,227 B1 | 11/2001 | Davis |
| 6,317,390 B1 | 11/2001 | Cardoza |
| 6,324,123 B1 | 11/2001 | Durso |
| 6,338,007 B1 | 1/2002 | Broadfield et al. |
| 6,346,886 B1 | 2/2002 | De La Huerga |
| 6,401,072 B1 | 6/2002 | Haudenschild et al. |
| 6,406,426 B1 | 6/2002 | Reuss et al. |
| 6,408,330 B1 | 6/2002 | De La Huerga |
| 6,480,147 B2 | 11/2002 | Durst et al. |
| 6,519,569 B1 | 2/2003 | White et al. |
| 6,539,281 B2 | 3/2003 | Wan et al. |
| 6,640,246 B1 | 10/2003 | Gary, Jr. et al. |
| 6,641,533 B2 | 11/2003 | Causey, III et al. |
| 6,671,563 B1 | 12/2003 | Engelson et al. |
| 6,689,091 B2 * | 2/2004 | Bui et al. ....................... 604/67 |

(56) References Cited

U.S. PATENT DOCUMENTS

| | | | |
|---|---|---|---|
| 6,731,989 B2 | 5/2004 | Engleson et al. | |
| 6,752,787 B1 | 6/2004 | Causey, III et al. | |
| 6,779,024 B2 | 8/2004 | De La Huerga | |
| 6,790,198 B1 | 9/2004 | White et al. | |
| 6,988,075 B1 | 1/2006 | Hacker | |
| 7,041,941 B2 | 5/2006 | Faries, Jr. et al. | |
| 7,051,120 B2 | 5/2006 | Greene et al. | |
| 7,384,410 B2* | 6/2008 | Eggers et al. | 604/67 |
| 2001/0025156 A1 | 9/2001 | Bui et al. | |
| 2001/0027634 A1 | 10/2001 | Hebron et al. | |
| 2001/0028308 A1 | 10/2001 | De La Huerga | |
| 2001/0031944 A1 | 10/2001 | Peterson et al. | |
| 2001/0041920 A1 | 11/2001 | Starkweather et al. | |
| 2001/0044731 A1 | 11/2001 | Coffman et al. | |
| 2001/0049608 A1 | 12/2001 | Hochman | |
| 2002/0002326 A1 | 1/2002 | Causey et al. | |
| 2002/0019606 A1 | 2/2002 | Lebel et al. | |
| 2002/0143290 A1* | 10/2002 | Bui et al. | 604/67 |
| 2002/0169636 A1 | 11/2002 | Eggers et al. | |
| 2003/0139701 A1 | 7/2003 | White et al. | |

FOREIGN PATENT DOCUMENTS

| | | |
|---|---|---|
| GB | 2154344 | 9/1985 |
| GB | 2309801 A | 8/1997 |
| WO | 9910029 | 3/1999 |
| WO | WO 99/10029 | 3/1999 |
| WO | 0013588 | 3/2000 |
| WO | 0043941 | 7/2000 |
| WO | 0052626 | 9/2000 |
| WO | 0057339 | 9/2000 |
| WO | 0069331 | 11/2000 |
| WO | 0072181 | 11/2000 |
| WO | 0060522 | 12/2000 |

OTHER PUBLICATIONS

"Automated Infusion Pump", J. Bisera et al., Jan., 1976, pp. 25-30.
"Accuracy of Drug Infusion Pumps Under Computer Control", Connor et al., vol. 39, No. 9, Sep. 1992, pp. 980-982.
"HP VueLink Module Makes Data from B. Braun", Gale Group, Dec. 23, 1998.
"A Review of Programmed Insulin Delivery Systems", Spencer, vol. BME-28, No. 3, Mar. 1981, pp. 237-251.
"A Computer System for Real-Time Monitoring and Management of the Critically Ill", Stewart, et al., Fall Joint Computer Conference 1968, pp. 797-807.
IMED Status "Infusion Management System", pp. 1-6.
"PinPoint Enhances Local Positioning System Technology; Incorporates Features Specifically Designed for Healthcare", Business Wire, Apr. 10, 2000.
"Assisted Drug Risk Management Using Computer-Controlled Infusion Pumps and a Programmable Bedside Monitor", D.A. Silvern et al., Journal of Clinical Engineering, vol. 14, No. 5, Sep.-Oct. 1989, pp. 381-389.
"Electronic Medical Record in the Intensive Care Unit", Sado, vol. 15, No. 3, Jul. 1999, pp. 499-522.
International Search Report, Application No. PCT/US00/13267.
Magic Medicine Cabinet: A Situated Portal for Consumer Healthcaer, HUC '99, Dadong Wan, Center for Strategic Technology Research Accenture, Northbrook IL (4 pages).
Paul Lavin, "Small but Perfectly Informed Will a Java Ring Become the Next Must-Have Fashion Accessory?" The Independent, London, Apr. 7, 1998.
"Medical Alerty Systems," The University of California Berkley Wellness Letter, vol. 7, No. 1, p. 1, Oct. 1990.
"Surgical Patients Carry Records on Wristband," USA Today, vol. 126, No. 2631, p. 7, Dec. 1997.

* cited by examiner

| 20 | Memory Contents -- Patient Identification Device 10 |
|---|---|
| 21 | Specific Patient Information |
| 22 |     Patient Identification Number |
| 23 |     Patient Name |
| 24 |     List of Medications to which Patient is Allergic |
| 25 |     Admitting Physician |
| 26 |     Patient Blood Type |
| 27 |     Height |
| 28 |     Weight |
| 29 |     Body surface area |

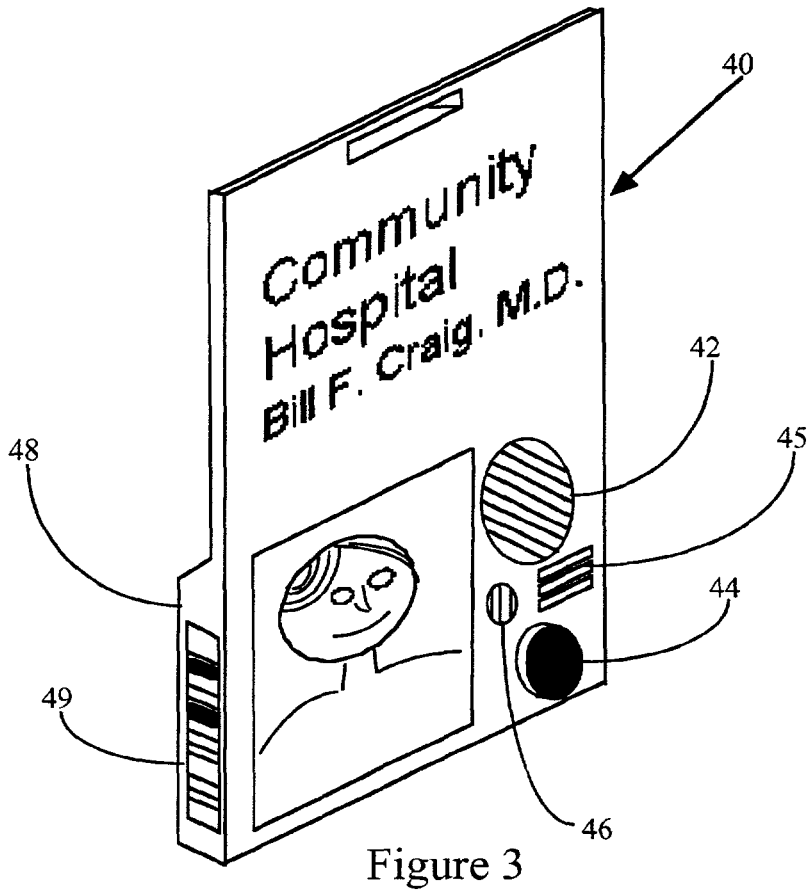

Figure 3

| 60 | Memory Contents -- Physician Identification Device 40 |
|---|---|
| 61 | Administering Physician Information |
| 62 | Responsibilities/Title |
| 63 | Identification Number |
| 64 | Name |
| 65 | List of Patients Under Care of Physician |
| 68 | Date & time received information from patient information device 10 |
|    | Information Received from Patient Identification Device 10 |
| 21 | Specific Patient Information |
| 69 | Date & time received information from memory device 201/bar code 203 |
| 220 | Information Received from Memory Device 201/Bar Code 203 |
| 222 | Target Patient Information |
| 226 | Predetermined Physician Information |
| 230 | Dispensed IV Medication Information |
| 250 | Medication Report Components |
| 251 | Date and time received pump identification number 130 |
| 130 | Pump identification number |

Figure 4

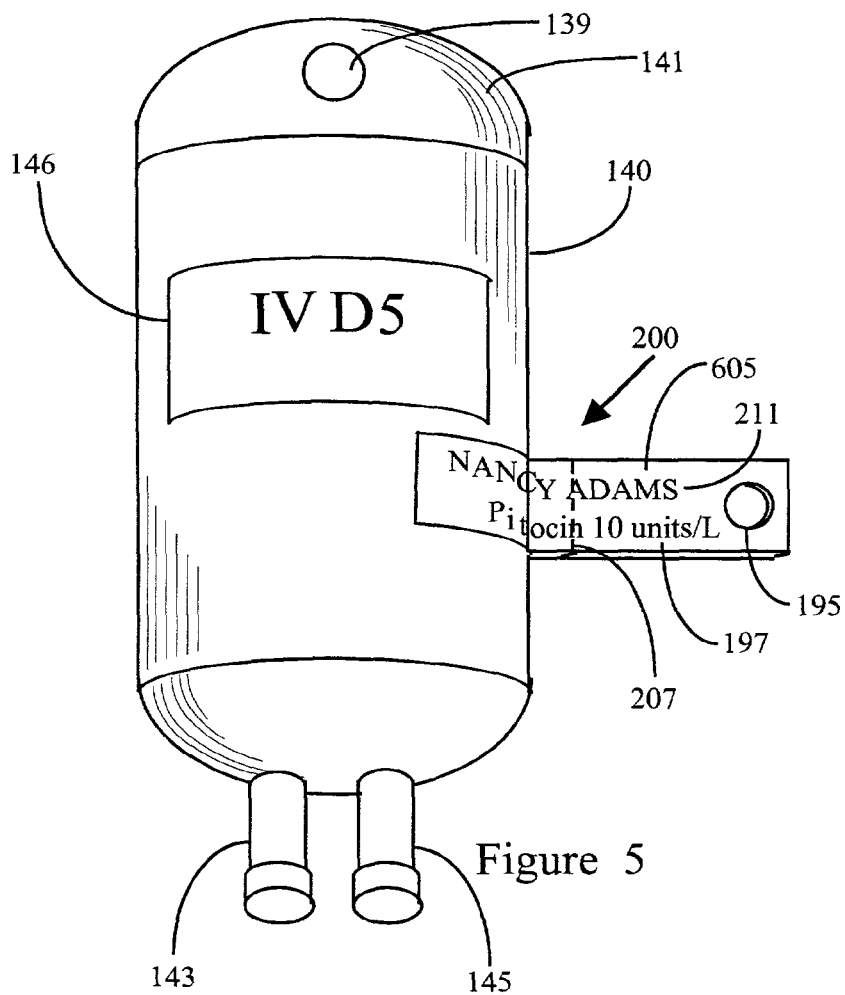
Figure 5
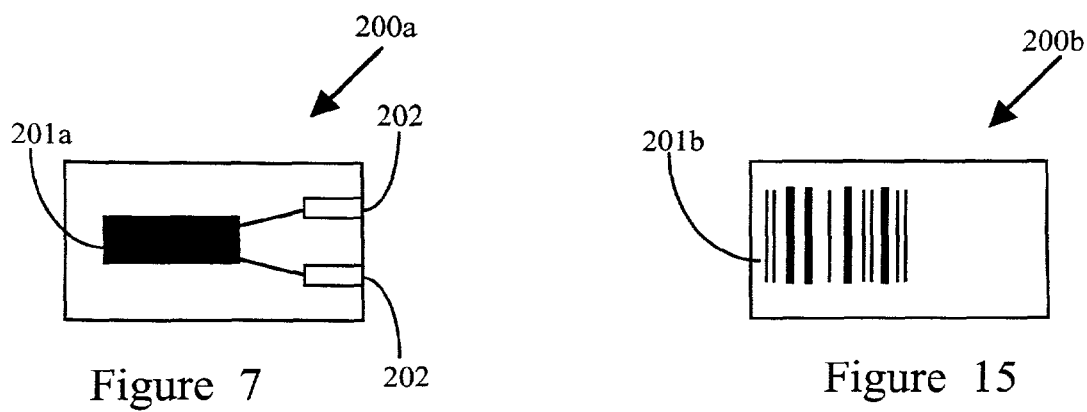
Figure 7
Figure 15

| | |
|---|---|
| 220 | Memory Contents -- Memory Device 201 |
| 222 | Target Patient Information |
| 223 |     Patient Identification Number |
| 224 |     Patient Name |
| 226 | Predetermined Physician Information |
| 227 |     Responsibilities/Title Of Physician Allowed to Give Medication |
| 228 |     Physician Identification Number(s) Allowed to Give Medication |
| 229 |     Physician Name(s) Allowed to Give Medication |
| 230 | Dispensed IV Medication Information |
| 232 |     Date and Time Medication Dispensed |
| 233 |     Identification of Physician who dispensed Medication |
| 234 |     Type and Quantity Actually Dispensed |
| 236 |     Medication name/number |
| 237 |     Prescribed Patient ID |
| 240 |     Prescribed dosage |
| 241 |         flow rate, |
| 242 |         duration, |
| 243 |         dose, e.g. mcg/kg/hr |
| 244 |         medication concentration |
| 245 |         titration standing order |
| 580 |         route |
| 246 |     Presciption order number |
| 247 |     Ordering physician |
| 248 |     Order verified and date |
| 249 |     Time to adminster medication |
| 250 | Medication Report Components |
| 252 |     Medication Report |
| 254 |     Universal Record Locator |

Figure 6

| | |
|---|---|
| 280 | Memory Contents -- Memory Device 105 |
| 130 | Pump identification number |
| 282 | Patient Information |
| 61 | Administering Physician Information |
| 284 | IV Medication Information |
| | Memory Contents relatred to Pump Unit |
| 61 | Administering Physician Information |
| 284 | IV medication Information |
| 290 | Order verified |
| 291<br>292<br>293<br>294<br>295<br>296 | Pump status<br>    flow rate<br>    duration<br>    dose, e.g. mcg/kg/hr<br>    volume to be infused<br>    volume infused |

Figure 18

METHOD AND APPARATUS FOR CONTROLLING AN INFUSION PUMP OR THE LIKE

CROSS-REFERENCE TO RELATED APPLICATIONS

This application is a continuation of Ser. No. 10/004,941 filed Dec. 3, 2001, which is a continuation-in-part of U.S. patent application Ser. No. 09/426,553 filed Oct. 22, 1999 which was entitled "Method And Apparatus For Verifying Information". In addition this is a continuation-in-part of U.S. patent application Ser. No. 09/832,770 filed Apr. 11, 2001 entitled "Interactive Medication Container". Moreover this is a continuation-in-part of U.S. patent application Ser. No. 09/833,258 filed Apr. 12, 2001 and entitled "Product Labeling Method And Apparatus". Each of the above patents is incorporated by reference in its entirety.

STATEMENT REGARDING FEDERALLY SPONSORED RESEARCH OR DEVELOPMENT

Not applicable.

BACKGROUND OF THE INVENTION

The field of the invention is medical information devices and more specifically the field of device enhanced IV bags, pumps and pump assemblies that cooperate to reduce the potential for mis-medication and that substantially reduce pump assembly clutter.

While the present invention is applicable to any of several different IV type systems including syringe, bag, cartridge, etc., in order to simplify this explanation prior art and the present invention will be discussed in the context of a bag type IV system. In addition, while any of several different hospital personnel may be able to administer services and medications to a patient within a hospital, to simplify this explanation the term "physician" will be used to indicate any person that renders services or medication within a facility unless indicated otherwise. Moreover, the term "medicant" will be used to refer generally to any type of liquid solution for delivering substance to a patient via an infusion pump. Furthermore, while the present invention may be used in conjunction with infusion systems including a single pump unit, the invention is particularly useful in cases where a system includes several pump units and therefore the invention will be described in that context unless indicated otherwise.

While there are several different ways to deliver drugs, nutrients, etc., to a patient, one of the most widely adopted delivery systems is the infusion pump system wherein drugs or nutrients to be delivered to a patient are dissolved in a liquid solution and stored in a container, typically a bag, that is linked through an infusion pump unit to the patient's blood stream via an intravenous (IV) tube and a needle. Infusion pump systems are advantageous because the amount of substance delivered to the patient over time can be regulated by setting the concentration of the solution and/or setting the pumping rate. To this end, typically an infusion pump unit is equipped with some type of pump controller that can be manually manipulated by a physician to modify substance delivery rate and liquid volume.

Often more than one medicant must be delivered to a patient at any given time. To accommodate simultaneous delivery of a plurality of medicants, most facilities simply provide a separate pump for each of the medicants. For instance, where ten medicants are to be simultaneously delivered to a single patient, ten separate pumps, IV lines and IV bags are provided. In effect, the separate pump unit systems are supplementable to accommodate whatever number of medicants need to be delivered to the patient. To organize several pump units and minimize the space required to accommodate the pump units, often a shelving assembly is provided that organizes the units in a vertical fashion (i.e., one unit above another).

In the past the task of managing medicant infusion processes was relatively simple as most patients were administered only one or a two medicants at any given time. Recently, however, medicant delivery management has been made more difficult due to the large number of different medicants now available. For instance, a patient with five symptoms may now be administered five separate medicants, one medicant to address each of the five separate symptoms. In addition, where five separate medicants are delivered, the medicant volumes may have to be balanced so that a total medicant volume does not exceed a maximum safe volume to be delivered to a particular patient. Also, prior to delivering specific medicants, special protocols have to be performed. For instance, an exemplary protocol may require that a patient's temperature be taken where the medicant can be delivered only if the temperature is within a specific range. As another example, some medicants should only be delivered on an empty stomach and a physician should determine, prior to delivery, the time since the patient's most recent meal.

Moreover, where the total safe volume corresponds to a patient's size (i.e., weight, height, muscle mass, etc.), the total safe volume may change over time so that the volumes of each of the medicants has to be adjusted over time. Furthermore, it may be that a particular patient is allergic to specific medicant "cocktails" (i.e., mixtures) such that medicant mixtures have to be modified over time. Thus, during the course of a patient's stay at a medical facility, it is often that case that the rate of medicant delivery and the medicants delivered must be altered several times as a function of patient conditions.

To facilitate infusion pump setting and real time medicant delivery rate and volume adjustments during a patient's stay at a facility, most infusion pump systems are provided with some type of manual interface device that facilitates simple infusion setting alterations. Because there are only a small number of infusion settings, the interfaces may be relatively minimal including a small display and a small number of input keys (i.e., volume increase and decrease buttons, etc.). Minimal interfaces are relatively inexpensive and therefore expandable systems (i.e., systems that accommodate additional medicants by adding additional pump units) often include a separate interface device attached to each one of the pump units. For instance, if a system includes ten pump units, the system would also include ten separate interface devices for setting infusion parameters.

While expandable systems like those described above have various advantages (e.g., system hardware can be expanded and eliminated as desired), such expandable systems also have several shortcomings. First, clearly, as with any system, as more components are added to the system, the physical components of the infusion pump system become more difficult to track and manage. For instance, distinguishing system lines is important as pump unit settings have to be adjusted as a function of the medicant linked to a particular pump. In this regard, every time another pump unit and corresponding medicant bag are added to a system, an additional IV line has to be added to the system to link the bag and the corresponding pump.

While an additional line may not seem to cause much confusion at first, as several lines are added to the system, the lines begin to resemble spaghetti (i.e., the lines all have a similar appearance) and it becomes difficult to distinguish one line from the others. The task of distinguishing lines is exacerbated as most IV pump systems are simply located in any available suitably sized space within a patient's room and often have to be moved to accommodate other medical equipment. Thus, IV systems are often provided on wheeled upright supports that can be moved about a patient within the patient's room. Such movement can cause a plurality of IV lines to become entangled.

Similarly, because expandable systems typically include a separate interface for each pump unit, the task of employing the interfaces can be tedious. For instance, where there are a large number of interfaces (e.g., 8-10) that are stacked on a unit shelf, the lower interfaces may be difficult to observe. In addition, because pump systems are often moved to accommodate other medical equipment, often the systems have to be manipulated into observable orientations prior to using the interfaces.

Second, in addition to problems associated with the physical components of expandable systems, such systems also can lead to inadvertent mis-medication problems. For instance, as indicated above, where several IV bags are linked to a patient via several pump units and IV lines are crossed one or more times, a physician could easily mistake one pump unit for another and adjust or set an infusion setting for one medicant meant for another.

Third, where several medicants are simultaneously delivered to a single patient even a simple process of modifying medicant delivery rates can be complex. For instance, assume that ten medicants are being delivered to a patient and that a physician wishes to increase one of the medicant delivery rates. In this case, to ensure that the total volume of medicant delivered does not exceed the maximum safe volume, the physician would have to manually examine each of the pump unit interfaces to identify each medicant volume, add up the volumes and then determine if the desired increase is acceptable. In the event that the desired increase would increase the total volume to a level above the maximum, if the physician still wants to facilitate the increase, the physician has to determine which of the other medicant delivery rates can be decreased. Clearly this decision making and adjusting process is arduous. A similar process would be required if an additional medicant were to be added to the medicants being administered to the patient.

Fourth, record keeping in the case of an expandable infusion system can be difficult. To this end, to facilitate billing, historical archiving and diagnostic and prescriptive needs, virtually every modification to medicant delivery should be recorded in detail including the rate change, the medicant for which the rate was changed, the time at which the rate was changed, etc. With conventional infusion systems all changes have to be manually recorded in a patient's bed side chart for later transcription into an electronic filing database. Just as simple modifications to delivery rates are tedious to facilitate, so to are the records that indicate the modifications. For instance, consider again the case where ten medicants are administered to a patient and a physician intends to increase one of the medicant delivery rates. If other medicant delivery rates have to be altered to accommodate the increase in the one medicant, the physician has to make the modifications to other rates and then record each of the modifications.

U.S. Pat. No. 5,980,501 (the "'501 patent") teaches one infusion system wherein an electronic memory is provided on a medication bag where medication information is stored on the memory and can be obtained from the memory when an information reader is placed adjacent the memory. The reader is linked to the bag adjacent the memory via a clip and is linked to a controlling pump unit via a data cord to provide medication information to the pump for regimen control purposes.

While the concepts in the '501 patent address various problems with prior art including pump programming problems that have lead to mis-medication in the past, the concepts in the '501 patent have several shortcomings. First, by requiring both a cord and an IV tube to be linked between each IV bag and a corresponding pump unit, the number of connections between IV bags and pump units is doubled. While additional connections may not be confusing in cases where only a single bag is linked to a patient, additional connections where more complex configurations are employed increase the likelihood of confusing which bags are linked to which pump units as IV lines and data cords often have similar appearances and may cross each other several times between corresponding bags and pump units.

For instance, assuming that four separate medicant bags are to be linked to a patient A. It is possible that a physician could link a single pump unit to a data cord corresponding to a first medicant and to an IV tube corresponding to a second medicant so that the information obtained from one of the information devices would be used to control administration of some other medicant and vice versa. Clearly such an inadvertent mix-up would cause mis-medication.

As another instance, again assume that four separate medicants are linked to a patient through a pump including seven inlet ports and a single outlet port that links to the patient and that a physician has manually adjusted settings for each of the separate medicants via a pump interface where the manual settings are different than the settings specified in the memory devices. Also assume that three of the four medicants have to be replaced. In this case, the physician has to trace the IV tubes from each of the medicants to be replaced to the corresponding pump units and disconnect the tubes from the corresponding pump unit inlet ports. After retrieving the replacement medicant bags, the physician has to make sure that the replacement bags are linked to the inlet ports from which the corresponding empty bags were removed. This can be accomplished by observing the pump interfaces to determine which units are associated with which medicants and then linking up the tubes to the pump units. These tracing and confirmation tasks are tedious at best and clearly could lead to configuration and medicant delivery errors.

Second, the simple task of determining which of several medicants is almost gone where several medicants are being delivered through a pump assembly to a single patient is also tedious. With the '501 patent system a physician has to either manually place the IV bag that is low on medicant within the physician's line of sight and read the information there from or has to trace the IV tube from the low medicant bag to the corresponding pump unit and obtain the medicant information there from. As known in the industry medicant bags are typically relatively flimsy and are often hung on IV stands such that medicant labels are not always easy to observe. As indicated above, tracing tubes to pumps is difficult.

Third, the '501 patent fails to facilitate record keeping tasks. To this end, while the '501 patent teaches a system for downloading prescription information into a pump unit and also teaches an interface for manually modifying infusion settings, the '501 patent fails to teach any way of tracking and recording manual delivery modifications.

Fourth, the '501 patent system does not overcome the problems discussed above with respect to multiple interfaces (i.e., a separate interface for each pump unit).

Fifth, while the '501 patent teaches that bag memories should be disabled after a single use, the '501 patent fails to recognize that the same information stored in a bag memory may be included in a pump unit memory and could be used to administer other medicants to a patient. For instance, assume that a medicant A bag is empty and is to be removed from a pump unit. After removing the empty bag, the pump unit settings remain set in the pump unit. If another bag were linked to the pump unit, the unit may use the current settings to deliver medicant to the patient.

Sixth, the '501 patent system fails to teach correlation of a medicant with a particular patient or prescription prior to delivery. For instance, when a bag is linked to the '501 patent pump, the pump simply obtains information from the bag and adjusts pump settings as a function of the obtained information. The '501 patent then begins medicant delivery according to the settings without regard for whether or not the patient linked to the pump is the patient for whom the medicant was released from the pharmacy.

Seventh, the '501 patent system can inadvertently carry out a stale medicant regimen either on the patient for which a medicant was dispensed or on another patient. For instance, a bag memory could be retrieved by the '501 patent system and stored in a system memory prior to linking the medicant to a patient A, the patient for whom the medicant was intended. Several minutes later patient A could be moved within the facility and a patient B could be placed in patient A's position. In this case, medicant A may be administered to patient B inadvertently. While the '501 reference teaches including an expiry date on each memory device, such an expiry date would not overcome mismedication like that described above.

Other prior art references have addressed some of the shortcomings of the '501 reference. For instance, with respect to reducing confusion among several pump units and corresponding IV lines, U.S. Pat. No. 5,713,856 (hereinafter "the '856 patent) teaches a system including a single patient interface unit and a plurality of linked functional units where each functional unit may be a separate infusion pump unit. A system operator uses the interface unit to set parameters for each of the functional units. The functional units are integrally mounted to the interface unit and receive instructions there from regarding infusion rate, volume, etc.

The '856 patent system is advantageous as it requires only one interface and a reduced number of IV lines and data cords. Nevertheless, the '856 system still has some of the shortcomings associated with the '501 patent and also has additional short comings such as requiring either manual entry of medicant information or a correlating process whereby medicant in a bag is correlated with medication/prescription information from a medication or patient record.

Other references teach systems where patient information can be read by bar code readers and the like so that systems can automatically determine if a medication is administrable to a particular patient (i.e., determine if the patient is allergic to a medication, determine patient blood type, etc.). These systems, however, typically operate on a pre-delivery basis (i.e., at a physician's office or at a facility pharmacy) and not as a function of patient conditions or circumstances at the time of medication delivery. For instance a patient may be allergic to a medicant combination including medicants A and B. The patient's allergy may not be noted in the patient's chart and therefore, even where the patient is currently being administered medicant B, a physician may prescribe and administer medicant A thereby causing an allergic reaction. Even where the patient's allergy is noted on the patient's chart, a physician may inadvertently fail to notice the allergy and prescribe medicant A despite current delivery of medicant B. Similarly, even where a physician recognizes the allergy, the physician may inadvertently or accidentally prescribe medicant A despite current delivery of medicant B. Thus, while existing systems can recognize various drug combinations that should be avoided, often those systems are not linked to an IV system and therefore cannot alert physicians of potential mis-medication at the time of delivery.

Thus, there is a need for an IV system that enables simpler interfacing and more specifically a system that facilitates accurate prescription entry, verification that prescriptions are suitable at the time of delivery, avoidance of delivery of stale prescriptions, accurate and automatic delivery record keeping, a simple IV linking and de-linking protocol and simpler interfacing for monitoring and system setting modifications.

BRIEF SUMMARY OF THE INVENTION

This invention uses a patient wristband that can be machine read (e.g. bar code or RFID tag) to identify patients, an information device that is attached or adhered to an IV bag (e.g. bar code or RFID tag) containing instructions regarding the administration of the bag contents, and one or more IV pumps with intelligent controllers. In some instances a physician data collector (e.g. electronic ID badge or PDA) can be used to read information about a patient, from the wristband, the IV bag, from the information device, and transfer it to the IV pump. In some instances the data collector also reads information (e.g. bar code or RFID tag) about the IV pump and transfers it with the other information about the patient and the IV bag to a centralized IV pump controller.

In one embodiment the IV pump is capable of reading the information form the patient wristband and IV bag. When the information from the IV bag includes a patient identifier for whom is to receive the medication in the IV bag, the pump compares this with the patient information from the wristband. If the medication is not for this patient the IV pump can present an alert or block operation. Preferably the time between when the pump reads the wristband and the IV bag information is limited to a short period of time (e.g. less that 3 minutes) to minimize the chance for errors. There are occasions when the IV bag information will not include a patient identifier (e.g. "floor stock"), in which case no comparison can be made.

The IV bag information that is read by the pump can also include prescribed dosing information (flow rate, duration, volume to be delivered) which may include multiple settings for use over a separate intervals of time. The pump uses the dosing information to automatically set its operation. The physician need only press a start button to activate the pump. When the dosing information only includes an acceptable range of operation, but not a specific dose, the physician can set the pump to operate at flow rate. The pump can compare the entered flow rate with the acceptable range. When the range is not within the acceptable range the pump can alert the physician to this error. This can also be done when there is a specific pump dose specified, but the physician is required to enter it manually.

In some cases a medication in an IV bag is to be administered based on the patient's weight. The pump can obtain the weight directly from the patient's wristband and use this to set the flow rate of the pump.

When a pump is capable of pumping from more than one IV bag or line at a time, each IV bag (when specifying a patient identifier) must be for the same patient.

When a medication is to be administered via an unusual route (e.g. not intravenously) the pump can provide a prompt to the physician asking them to confirm that the correct route has been used. This is especially useful to determine that a medication for epidural use is not given intravenously.

When a pump is started without reading a patient wristband and/or the IV bag information device the pump can present an alert of a possible error.

When the last line attached to a IV pump is removed from the pump, the pump can erase any information it has previously stored about the patient, making the pump available for use on a new patient.

When the IV pump is turned off any information about. The previous patient and setting are erased. When the pump is turned on again it can check to see if an IV line is already placed in it or attached to it. An alert can be presented to the physician immediately, indicating to him that the pump has not been properly set up for this IV bag.

In some cases it is preferable for the physician to use an electronic badge (or PDA) as a data collector to read the patient wristband and the information device on the IV bag. Now the badge can compare and determine if the IV bag was dispensed for this patient. The badge then transfers the collected information to the IV pump to set its operation. The badge also determine the collection of information and the transfer of it to the pump all occurs within a time limit (e.g. 3 minutes).

Another embodiment of the invention uses a centralized pump controller (e.g. a laptop or tablet computer) providing the physician with a larger display for user interaction than normally available on an IV pump. The controller is able to program and monitor the performance of several pumps, giving the worker a single tool to control and review the operation of all the pumps administering IV medication to a patient.

In one use of the controller, the badge records information from the wristband, the IV bag information device, and in some cases an identifier placed on the IV pump (or a pump module when the pump can be used with more than one line). All of this information is transferred to the controller (e.g. via wireless communication). The controller determines if the patient the IV bag is was dispensed for corresponds to the same patient that the controller was previously sent. IF there is a mismatch an error is indicated and the controller will not interact with the specified pump. When there is a match or the controller was not previously in communication with an IV pump, the controller establishes communication with the IV pump using the pump identifier, which can be an RF address or frequency. Once in communication with the pump the controller determines if it is already running (manually started) and if the flow rate corresponds to that specified by the information device on the IV bag. If not or not within an acceptable range the controller presents an error. When the pump is not operating the controller transfers to the pump the dosing information received from the information device on the IV bag.

Generally when the controller is used to address the pump based on a selection made by the physician, the controller instructs the pump to activate a visual indicator (e.g. LED or use the pump display to present an easily noticed message).

In this manner the physician can clearly see which pump he is interacting with via the controller. When the physician discontinues an IV medication bag, the pump can continue to activate the visual indicator until the IV line associated with that bag is removed for the pump. If the bag is not removed within a time limit an error is presented.

When an IV bag that has not been associated with a specific patient is used the controller can use a healthcare facility network to query a database to determine if the medication in the bag has been prescribed for the patient, if not an error is indicated.

The controller records every manual modification to the operation of a pump providing an automated charting program. When a change is detected the controller can be used to present an alert if the physician does not identify himself to the controller within a time limit (e.g. 4 minutes). This process ensures that each change is recorded and attributed to a specific physician.

It should be understood that many aspects of the invention can be applied to other healthcare devices that are use in providing therapy to a patient, such as a ventilator, anesthesia machine, or balloon pump.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE SEVERAL VIEWS OF THE DRAWINGS

FIG. 3 is a perspective view of physician identifying device;

FIG. 4 is a schematic diagram of an exemplary memory content of the device of FIG. 3;

FIG. 5 is a perspective view of a medicant bag including an information tag according to one aspect of the present invention;

FIG. 6 is a schematic view of an exemplary memory content of the tag of FIG. 5;

FIG. 7 is a schematic of one embodiment of the tag of FIG. 5;

FIG. 15 is a schematic plan view of yet another tag embodiment that may be used with the bag of FIG. 5;

FIG. 18 is an exemplary memory content of the memory of FIG. 17;

DETAILED DESCRIPTION OF THE INVENTION

Figures 1, 2:
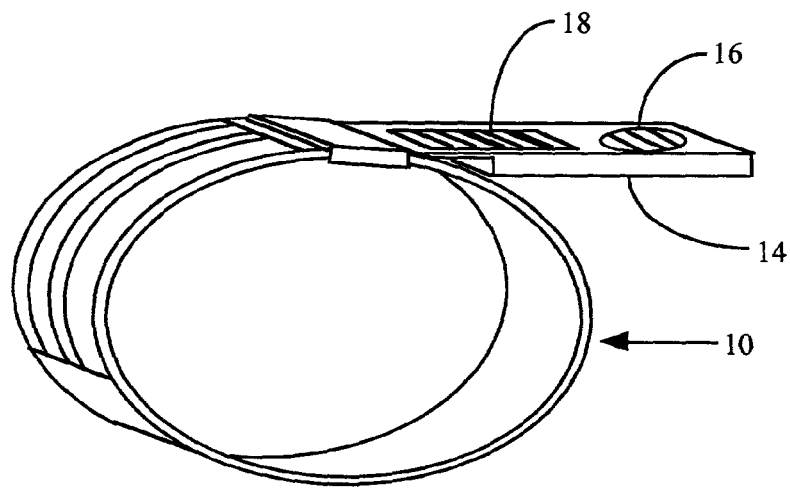
FIG. 1 is a perspective view of an identification device for a patient.
FIG. 2 is a schematic illustrating an exemplary memory contents of the device of FIG. 1.

Referring now to the drawings wherein like reference characters and symbols correspond to similar elements throughout the several views, the present invention will be described in the context of several exemplary systems for use in delivering medication to a patient 12 (see FIG. 26).

Generally, the systems used to describe the present invention are integrated systems wherein some type of controller is capable of obtaining information from several of the other system components and then using the information to provide valuable data to a system user and to enable unified control of medicant delivery to a patient. To this end, among other things, a controller may obtain medicant and prescription information from each of several different IV bags and use that information to automatically set pump operating parameters for specific pump units linked to the bags. In addition, a controller may collect information from a patient identification device and compare patient specific information with medicant information from bags to determine if mendicants in the bags are to be delivered to the patient. All of these processes are automated and require only minimal physician intervention and data processing so that most sources of human error are eliminated from the IV medicating and monitoring process. In addition, confirmation and communication protocols facilitate many of the inventive methods in a wireless or networked environment which reduces the number of hardware connections required to implement the inventions and thereby renders IV systems much more user friendly.

Hereinafter various electronic devices will be described separately and then various systems including the separate devices will be described and methods that are facilitated via the systems will be described. It should be appreciated that there are many different aspects described herein and that, unless clearly indicated as being necessary, none of the specific aspects are required but rather the various aspects may be combined in any of several different combinations to result in an inventive combination. It should also be noted that while devices are described as having certain components, many of the components and their functions may be provided via any of several commercially available processors programmed to perform the functions.

A. Patient Identification Device

Referring now to FIG. 1, a patient identification device 10 is illustrated. While device 10 is illustrated as being a patient ID device, the form of device 10 is not particularly important for the purposes of the present invention and therefore any type of patient mounted device 10 or device that can be uniquely associated with patient 12 is contemplated. Referring also to FIG. 26, device 10 is attached to a limb of patient 12 and therefore is physically associated with patient 12.

Device 10 includes a processor and memory that are disposed within a housing 14. For a better understanding of the components and construction of an exemplary device 10 see U.S. Pat. No. 5,883,576 which issued to De La Huerga on Mar. 16, 1999 and which is entitled Identification Bracelet With Electronic Information and which is incorporated herein by reference. Although not separately illustrated, because the processor and memory are located within housing 14 and are linked together, hereinafter the numeral 14 will be used to refer to the device 10 processor and memory combined. Device 10 also includes a communication device 16 and an interface device 18. Processor 14 is linked to each of the communication device 16, the memory and the interface device 18.

Referring also to FIG. 2, the device 10 memory includes a memory content 20 that includes a list of information 21 that is typically specific to the patient 12 that is wearing device 10. To this end, exemplary information includes a patient identification number 22, the patient's name 23, a list of medications to which patient 12 is allergic (or genomically incompatible with the patient) 24, identification of an admitting physician 25, the patients blood type 26, and the patient's height, weight and body surface area 27, 28 and 29, respectively. Other information (e.g., patient records, etc.) is contemplated but has not been included in FIG. 2 in the interest of simplifying this explanation.

In the illustrated embodiment, the memory is electronic and communication device 16 is an RFID tag that is capable of transmitting at least a subset of the information stored in the memory and, in at least some embodiments is capable of receiving information for storage in the device memory from other system devices or at least receiving an activation signal indicating that device 10 should transmit memory information.

Interface 18 is illustrated as being a small screen but could take any of several other forms including one or more LEDs to indicate device status visually, one or more buttons activatable to provide information to processor 14 and/or an audible indicator such as small speaker or beeper device. In other embodiments device 18 may simply provide information passively. For instance, static devices 18 may include a bar code or some other machine recognizable optical characters.

Hereinafter, in the interest of simplifying this explanation, while communication device 16 may take any of several different forms and may be powered in any of several different ways either internally or externally, it will be assumed that device 10 is an externally powered RFID device and, to that end, device 16 is an RFID antenna linked to the device processor. In this regard, device 16 receives power when placed in a magnetic field having a specific frequency and provides that power to the processor. Similarly, the excited processor provides signals to the device 10 which are transmitted to an external reading device as described in more detail below.

Nevertheless, it should be appreciated that device 10 may take any of several other forms including an internally powered RFID device that includes a battery, a passive bar code or dot matrix device, an optical device, an electronic device capable of infrared communication, etc. In any embodiment the memory component of the device 10 should be capable of storing information like the information in FIG. 2 in a machine/processor obtainable format.

B. Physician Identification

Referring now to FIGS. 3 and 4, to identify each physician working at a facility, each physician wears or carries a physician identification device 40 that stores information or memory contents 60 in a machine obtainable format. Illustrated device 40 is an identification badge including, among other things, a communication device 42, an activation button 44, an audible indicator (e.g., speaker) 45, a visual indicator (e.g., LED) 46 and processor and memory (not illustrated) that reside within a badge housing 48. Once again, the badge processor and memory are linked together and both reside within housing 48 and the processor and memory combined will be referred to herein by numeral 48. Also, while not illustrated, it is assumed that device 40, includes a battery.

Referring to FIG. 4, exemplary memory contents 60 includes a list of information corresponding to the physician wearing badge 40 and, in some embodiments, may temporarily include additional information related to medicant administration and a particular patient. The physician information includes administering physician information 61 such as physician responsibilities/title 62, identification number 62, name 64, and a list of patients under care of the physician 65. List 61 may include additional data elements or fewer than shown.

With respect to medicant administration and patient information, it is contemplated that device 40 may be used in several different ways. For instance, device 40 may simply be used to identify a wearing physician in which case medicant administration information would not be stored on device 40. As another example, in addition to being used to identify a physician, device 40 may also be used to transfer information (e.g., medicant administration information, patient information, etc.) among other system devices such as bracelet 10, IV bag tags described below, controllers and IV pumps. In this case, device 40 is programmed to obtain (e.g., read or receive) information from other devices, store the obtained information and transmit the information via communication device 42. As yet one other example, device 40 may also be able to perform various portions of inventive protocols such as comparing medicant and patient information to determine if a particular medicant should be delivered to the patient and then controlling operation or setting operating parameters of an IV pump as a function of the comparison. These and other functions of device 40 are explained in more detail below.

Referring still to FIGS. 3 and 4, exemplary medicant and patient information includes patient information 21 (see also 21 in FIG. 2), date and time (collectively referred to as a "time" in some parts of this specification) patient information is obtained 68, date and time information is obtained from an IV bag memory device 69, information received from an IV memory 220, target patient information 222 indicating a patient for which an IV bag has been provided, physician information 226 indicating at least one physician that is authorized to administer a medicant, dispensed IV medicant information 230, a medication report component 250, a date and time at which device 40 receives a pump identification number 251 and a pump identification number 130. Many of these information segments are described in more detail below.

Referring also to FIGS. 1 and 2, physician identification device 40 can use communication device 42 to obtain a portion or all of memory content 20 from device 10 and transfer the obtained information to memory 48 to be stored as part of memory content 60. Obtaining information from patient identification device 10 can be initiated by pressing button 44 on badge 40 at which point device 40 transmits a query signal to device 10 causing device 10 to transmit required information.

In some embodiments the date and time 68 (see contents 60) at which patient information is obtained may be provided by a real time clock (not separately illustrated) included within processor 48 and may be recorded in memory contents 60. To this end, when patient information 21 is obtained via device 42, the clock can indicate the date and time 68 to be stored with the received patient information 21.

As in the case of patient identification device 10, physician device 40 may take any of several different forms including the self powered RFID device 40 described above, an externally powered RFID device, a passive bar code or dot matrix, an optical device, an electronic device that communicates via IR, etc. Obviously, in the case of some passive devices (e.g., a bar code device), some of the functionality that is possible with an active processor based device cannot be facilitated.

C. IV Devices

Referring now to FIG. 5, an exemplary bag 140 for use with the present invention includes, among other things, a conventional information label 146, some type of information memory tag 200, an aperture 139 in an upward extension 141 for linking the bag 140 to a bag support and outlet ports 143 and 145 for linking the bag 140 to IV pump units for medicant delivery. Label 146 includes printed human readable indicia that can be used to identify the content of bag 140 in a conventional manner.

In one aspect the present invention contemplates some type of label or tag 200 that can be mounted to IV bag 140 and which can be used to obtain information about the medicant in the bag in an automated fashion. To this end, tag 200 may include a transmitter and a power source for transmitting information stored electronically in a memory. Transmitting labels may include RF devices, IR devices, etc. Another alternative is to provide a passive tag such as a bar code, dot matrix, optical or resistive indicator, etc. Exemplary label devices or tags are described in more detail below. Generally, by providing medicant prescription and infusion instruction (e.g., pump unit parameter settings) on a tag 200 and a system for automatically obtaining that information, verifying and setting infusion parameters, many typical infusion errors can be avoided.

Referring still to FIG. 5, tag 200 is a label device that is either formed within bag 140 (e.g., molded within the bag wall) or, as illustrated, is mounted via glue or in some other suitable fashion (e.g., band, etc.) to an external surface of bag 140. Tag 200 forms an external surface 211 on which medicant information specific to a particular prescription can be provided including one or more of an intended recipient's name, dose and volume specification, the prescribing physician, qualifications regarding physicians that may administer the medicant, instructions regarding delivery of the medicant, etc.

Tag 200 includes a memory device (generally 201 in the Figs.) from which information regarding the medicant within bag 140 can automatically be obtained. Referring now to FIG. 6, an exemplary memory contents 220 that may be stored in memory 201 is illustrated. While contents 220 includes several information types, it should be appreciated that a subset of contents 220 may be provided in memory 201 or other information in addition to contents 220 may be provided in memory 201 depending on how the tag information is employed.

Exemplary contents 220 includes selected patient information 222 including an identification number 223 and name 224 for a patient for which the medicant in the bag has been dispensed, predetermined physician information 226 including responsibilities or characteristics of a physician allowed to administer medicant 227, ID numbers of physicians allowed to administer medicant 228 and names of physicians allowed to administer medicant 229, dispensed IV medication information 230 including date of medicant delivery 232, identification of physician that dispensed the medicant 233, type and quantity of medicant delivered 234, medicant name/number 236, prescribed patient ID 237, prescribed dosage 240 including flow rate 241, duration 242, dose 243, medicant concentration 244 and titration standing order 245, prescription order number 246, ordering physician 247, order verified date 248 and time to administer medicant 249 and medication report components 250 including a medication report 252 and a universal record locator 254. The nature of almost all of these information types is obvious to one of ordinary skill in the art and therefore will not be explained here in detail. Regarding less obvious information types and segments, those types will be explained in more detail below as they relate to other system components that have yet to be described.

It is contemplated that tags 200 will be programmed by a pharmacist or other physician using a dispensing system or a computer terminal equipped with a device capable of writing memory contents (i.e., list 220) to tags 200. In some cases the writing process will include printing information on an external surface of a tag including either human readable indicia or, in some cases, a machine readable code such as a bar code or dot matrix.

Hereinafter several different tag types are described. Each different tag type is referenced by the numeral 200 followed by a small letter (e.g., "a", "b", etc.), the letter differentiating one tag from another. For instance, in FIG. 7 one tag type is referenced as 200a. Similarly, because each tag includes at least one memory device or component, each different memory device is referenced by the numeral 201 followed by a small letter, the letter again serving to differentiate one memory from another. For instance in FIG. 7 the memory device or memory is referenced as 201a. In cases where tags are referred to generally the numeral 200 will be used and where tag memory is referred to generally the numeral 201 will be used.

Referring now to FIGS. 5 and 7, in a first embodiment, tag 200a includes an electronic memory 201a linked to contacts 202 which can be used to obtain information from the memory 201a and, during programming, may be used to provide information to memory 201a. Contacts 202 in FIG. 7 are electrical and to write information to memory 201a, contacts of a writer (not illustrated) that are similar to contacts 202 have to physically touch contacts 202 to write information to memory 201a. Similarly, in this case, to read information from memory 201a, reader contacts have to physically touch contacts 202. Tag 200a may be attached to a bag 140 in any secure and suitable manner (e.g., glue on a flap as illustrated in FIG. 5, etc.).

Referring to FIG. 15, in a second embodiment, tag 200b includes a bar code 201b that may include any of the information described above and which may be accessed by a suitable bar code reading device to obtain the stored information. In this case, a printer (not illustrated) would provide the bar code 201b on the tag 200b and a bar code reader would be used to obtain information from the tag 200b. Tag 200b may be attached to a bag 140 in any secure and suitable manner.

In many of the embodiments described herein, some means for disabling a memory 201 after use is desirable. For instance, after the contents of an IV bag have been depleted, a tag mounted to the empty bag should not be useable with other bags to program an IV pump unit. Similarly, where an IV solution is to be discontinued for a particular patient prior to complete depletion, facility protocol is typically to discard the bag and the remaining contents to avoid use with another patient. In this case, once again, the tag 200 should be disabled to avoid using information therein to program a pump unit a second time.

Referring again to FIGS. 5 and 15, to facilitate disablement of bar code memory 201b, a perforated line 207 may be provided through bar code 201b. Here, after bag content is depleted or dispensation is discontinued, tag 200b may be torn along perforated line 207 so that only a subset of the code remains on a corresponding bag. In this manner tag 200b in FIG. 15 may be rendered unable to provide information for pump unit programming purposes.

In tag embodiments that include both a processor and memory, tag configuration is relatively expensive. To reduce overall system costs, processor/memory based tags may be configured so that one or both of the processor and memory and other components (e.g., antenna, power source, etc.) are recyclable.

Figure 10:
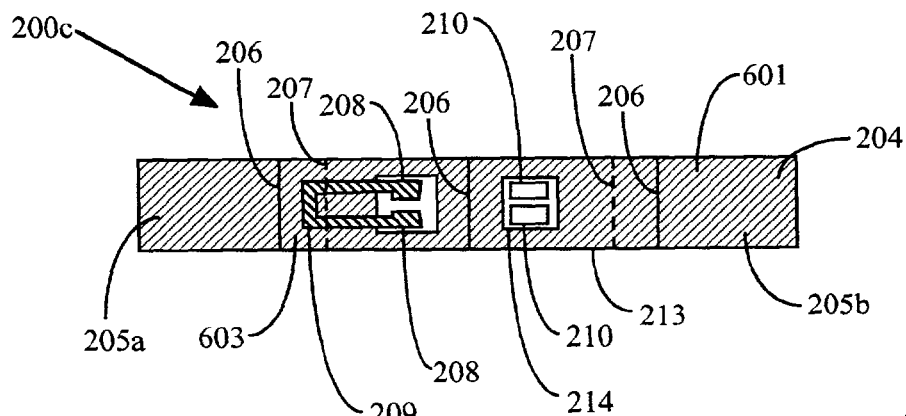
FIG. 10 is a plan view of yet another inventive tag embodiment.
Figure 11:
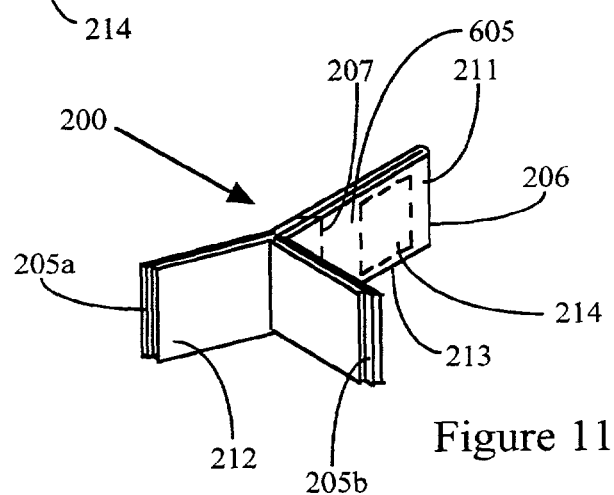
FIG. 11 is a perspective view of the tag of FIG. 10 folded into a useable configuration.
Figure 12:
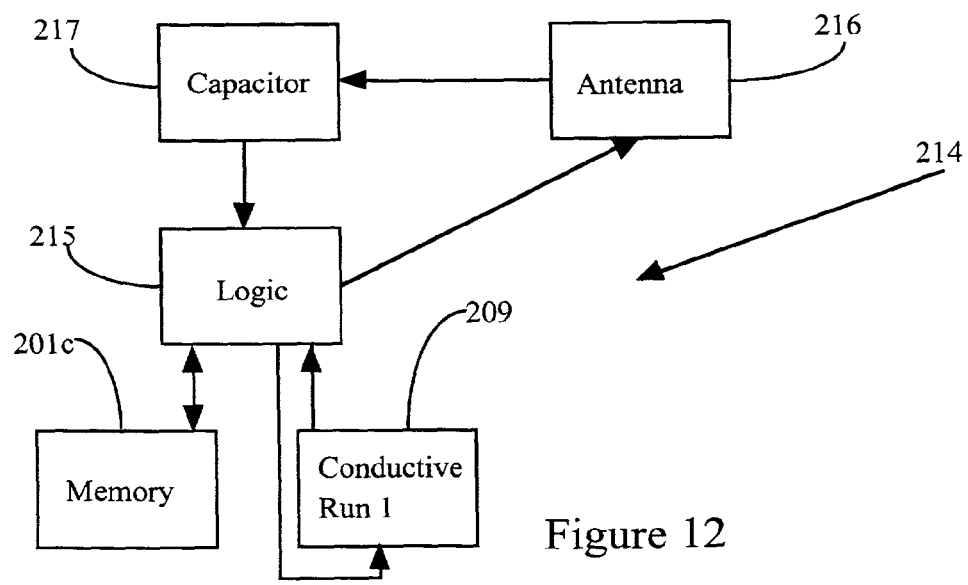
FIG. 12 is a schematic diagram of the circuit components of FIG. 10.

To this end, referring now to FIGS. 10, 11 and 12, in a third embodiment tag 200c includes an adhesive strip 204, contacts 208, a conductor 209 and an RFID memory circuit 214. Circuit 214 includes, among other components, separated first and second contacts 210.

Referring to FIGS. 10 and 11, strip 204 includes oppositely facing observable and hidden surfaces 211 and 601, respectively, where the observable surface 211 is observable after the tag 200 is mounted to a bag 140 for use and the hidden surface 601 is hidden from view after tag 200 is mounted to a bag 140. Strip 204 forms score lines 206 and perforated lines 207 that run perpendicular to a strip length (not separately indicated). The score lines 206 define four separate strip sections including end sections 205a and 205b at opposite end of the strip 204 and two mid-sections 603 and 213 that are separated by a central score line 206.

Memory circuit 214 is mounted to the adhesive hidden side 601 of strip 204 within mid-section 213 while contacts 208 and conductor 209 are mounted to hidden side 601 of strip 204 within midsection 603 with conductor 209 forming a loop between contacts 208. Conductor 209 and contacts 208 are arranged such that, when strip 204 is folded along the central score line 206 so that the hidden surfaces 601 of midsections 603 and 213 are adhered together, contacts 208 contact contacts 210 to form a closed circuit therewith. When so arranged, referring also to FIG. 5, midsections 603 and 213 together form a tab 605. Contacts 208 and conductor 209 can take several different forms and may include, among other components, a conductive adhesive applied to strip 204, glued metallic members or a conductive printed material.

Strip 204 forms two perforated lines 207, a separate line 207 in each of midsections 603 and 213, respectively. Line 207 in midsection 603 (i.e., the midsection including conductor 209) is positioned so that line 207 separates contacts 208. To this end, in the illustrated embodiment, line 207 passes through the loop formed by conductor 209 twice although other embodiments may include only a single pass. Referring also to FIG. 11, the perforated line 207 in midsection 213 is positioned such that, when strip 204 is folded around the central score line 206 and sections 213 and 603 are adhered together, the perforated lines 207 align.

Referring still to FIGS. 10 and 11, a release liner 212 is provided on the end sections 205a and 205b of hidden surface 601 (i.e., there are two separate release liners, one for each of sections 205a and 205b). Release liner 212 protects adhesive on sections 205a and 205b prior to attaching strip 204 to bag 140. When strip 204 is folded about central score line 206, end sections 205a and 205b can be folded in the opposite direction so that liners 212 face in a direction opposite tab 605. When so arranged, observable surface 211 can be used to print information related to the medicant within bag 140 (e.g., contents, patient ID, dosing information, etc.)

Referring to FIGS. 5 and 11, to adhere tag 200c to bag 140, release liners 212 can be removed from each of end sections 205a and 205b and the hidden surfaces of sections 205a and 205b can then be pressed against a surface of bag 140.

Referring also to FIGS. 10 and 12, when contacts 208 and 210 make contact (i.e., when strip 204 is folded about central line 206 such that corresponding sections of the hidden surface of strip 204 make contact) strip 204 forms the illustrated circuit 214. Memory circuit 214 includes control logic 215 that is in communication with an antenna 216, a power storage capacitor 217, memory 201c and conductor 209. Antenna 216 is a conventional RF antenna or magnetic field sensor for receiving power from an external device and for transmitting information to an external device via RF signals. When capacitor 217 is charged by antenna 216 and conductor 209 is intact, logic 215 accesses information within memory 201c and transmits the information via antenna 216.

To disable tag 200c from providing information after use, a physician tears strip 204 along perforated lines 207 which effectively severs conductor 209 causing an open circuit. Logic 215 detects the open circuit and halts transmission of information from memory 201c. Alternately, conductor 209 can be positioned between logic 215 and any of the other components in circuit 214 so when conductor 209 is severed memory circuit 214 is rendered incapable of providing information.

After a tag 200c is disabled, the torn off portion of the tag 200c can be returned to a facility pharmacy for recycling and inclusion in another tag device on another bag with new information corresponding to the new bag.

Referring again to FIG. 5, when text is printed on observable surface 211, the text can be centered so that the text also extends across perforated lines 207. In this manner, when distal tab 605 is torn away from other strip components, the text is also cut in a manner that prevents the text from being completely read, further preventing the tag information from being reused. Perforated lines 207 can be arranged as a diagonal line or as a chevron to further indicate when the distal tab 605 has been torn off.

Referring again to FIG. 12, capacitor 217 may be replaced with a battery for internally providing power to logic 215 and antenna 216. In this case, when conductor 209 is severed, logic 215 may set a bit in memory 201c indicating that the memory content should not be transmitted until the bit is reset at the facility pharmacy.

Figure 13:
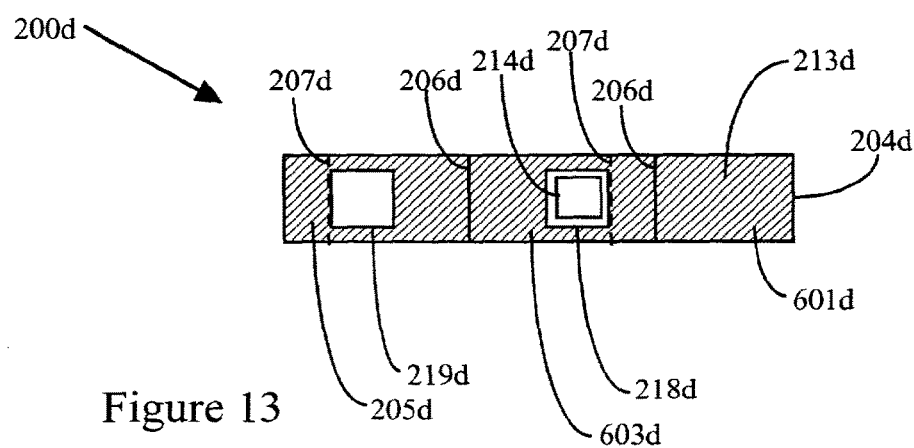
FIG. 13 is a plan view of another inventive tag embodiment.
Figure 14:
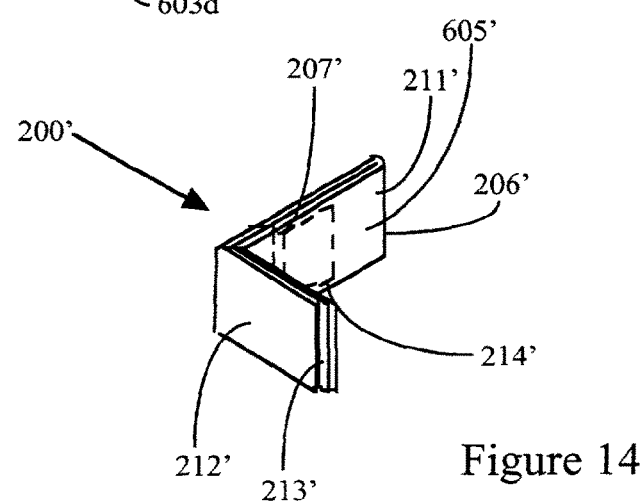
FIG. 14 is a perspective view of the tag of FIG. 13 folded into a useable configuration.

Referring now to FIGS. 13 and 14, a fourth embodiment of a tag 200d is similar to the tag 200c in FIGS. 10 through 12 with the exception that tag 200d does not include a conductor 209 and has a different alignment of score and perforated lines 206d and 207d, respectively. To this end, a strip 204d includes two score lines 206d that separate strip 204d into first and second end sections 205d and 213d and a midsection 603d. Strip 204d includes a hidden surface 601d illustrated in FIG. 13 and an observable surface 211d best seen in FIG. 14. On the hidden surface 601d, strip 204d includes an adhesive layer that is essentially evenly spread there across except for within circuit receiving spaces 219d and 218d on each of sections 205d and 603d, respectively. A memory circuit 214d is disposed within one of spaces 218d and 219d and, when sections 205d and 603d are folded with respect to score line 206d there between so that the hidden surfaces 603d thereof adhere together, spaces 219d and 218d form an envelop that houses circuit 214d. When so juxtaposed, as in the case of tag 200c in FIGS. 10-12, strip 204d forms a distal tab 605d.

Referring still to FIGS. 13 and 14, strip 204d also forms two perforated lines 207d one line 207d in each of sections 205d and 603d. The line 207d in section 603d is positioned on one side of space 218d. The line 207d in section 205d is positioned on one side of space 219d and such that, when sections 205d and 603d are adhered together as illustrated in FIG. 14, lines 207d are aligned. As in the case of strip 204, here a release liner 212d is provided on a hidden surface 601d of end section 213d to protect adhesive thereon until tag 200d is attached to an IV bag.

To attach tag 200d to a bag 140, sections 205d and 603d are bent about line 206d there between until the hidden surfaces 601d thereof adhere together to form an envelope with circuit 214d therein and so that sections 205d and 603d together form tab 605d. Next, end section 213d is bent in an opposite direction so that hidden surface 601d thereof faces in a direction opposite the direction in which tab 605d extends. When so configured, liner 212d is removed from section 213d and tag 200d is adhered to bag 140 (see again FIG. 5). Thus, in this embodiment strip 204d only has a single adhesive section 213d exposed, although other arrangements are envisioned.

When a bag 140 is to be discarded and tag 200d should be disabled, distal tab 605' is torn from other portions of strip 204d and circuit 214d can be easily removed from the envelope (i.e., the space defined by spaces 219d and 218d). It is believed that circuit 214 is not likely to be accidentally used when exposed and thus this embodiment also prevents memory contents 220 from being accidentally reused as part of a patient treatment. After being removed from strip 204d, memory circuit 214d can be returned to a facility pharmacy for erasing, insertion into a new strip 204, and reprogramming.

Referring once again to FIG. 5, according to the present invention, with tags 200 on each of several different bags 140, the information from each bag 140 may be obtained via a controller. To this end, while explained in more detail below, an exemplary controller includes some mechanism to obtain information from each of the tags 200. For instance, a controller may include an RFID transponder that can excite each of tags 200 and cause each tag 200 to send memory information to the controller. The controller may have to be placed proximate each tag 200 to excite the tag and obtain information there from or may be able to excite each tag 200 remotely (e.g., within 8 feet of the controller) to obtain information there from. In the alternative, where each tag 200 includes information in a bar code format, the controller may include a bar code reader that can read bar codes that are proximate the reader. In any event, it is contemplated that the controller can obtain information from each of tags 200.

Figure 9:
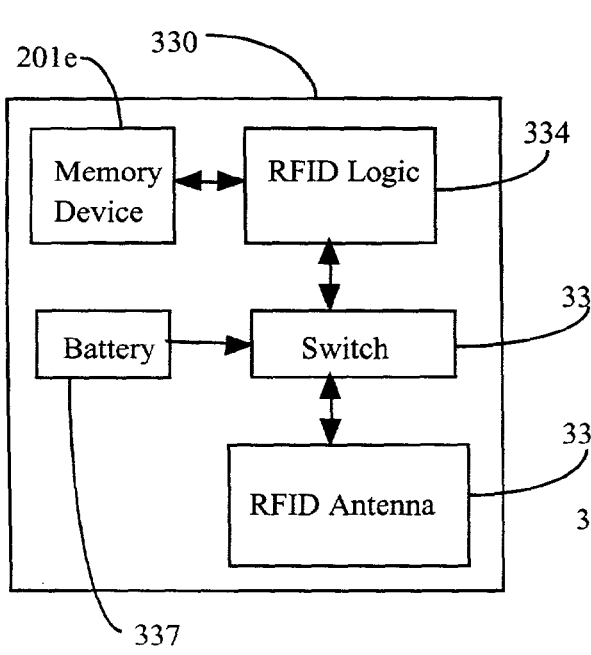
FIG. 9 is a schematic diagram illustrating various components of the device in FIG. 8.
Figure 8:
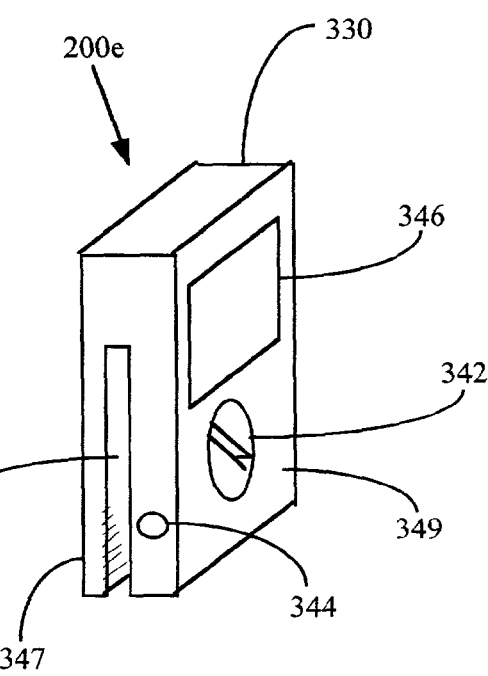
FIG. 8 is a perspective view of an electronic tag to be used with a bag like the bag in FIG. 5.

Referring now to FIG. 8, a fifth embodiment tag 200e is illustrated. Referring also to FIG. 5, it is contemplated that a "dumb" tab 605 is secured to a bag 140 and that the tab 605 does not have any memory. In addition, while illustrated as being removable via tearing along perforated lines 207, it is contemplated that, in this embodiment, tab 605 is not easily tearable along line 207 (i.e., perforated line 207 is not provided). Instead, referring also to FIG. 9, embodiment 200e includes a housing 330 that encloses a memory 201e, RFID logic 334, a switch 332, a battery 337 and an RFID antenna 336. In addition, tag 200e includes a reset button 344, a releasable connector 342 and an interface 346. Logic 334 is linked to memory 201e and is linked to antenna 336 via switch 332. Battery 337 is linked to other assembly devices to provide power thereto.

Housing 330 forms a slot 341 for receiving a dumb tab (see 197 in FIG. 5). When tab 605 is received within slot 341, connector 342 can be activated to lock tag 200e to the tab 605. In the illustrated embodiment, slot 341 is formed by facing leg members 347 and 349 where member 349 forms a threaded aperture (not illustrated). Connector 342 includes a screw received in the threaded aperture and having a distal end that extends toward leg member 347. Tag 200e is attachable to a tab 605 by tightening screw 342 (e.g., a quarter turn) within the aperture until the distal end of screw 342 pins the tab 605 against leg member 347. In the alternative, referring again to FIG. 5, tag 200 may form an aperture 195 through which the distal end of screw 342 passes or that receives some other mechanical clipping mechanism.

After tag 200e is secured to a bag via connector 342, information can be written to memory 201e via antenna 336 and a standard RF transfer protocol. Normally, when tag 200e is attached to a tab 605 via connector 342, the RFID tag can be activated to transmit information via antenna 336 to a controller 260 or some other receiving device. When tag 200e is removed from a tab 605, switch 332 is opened preventing memory 201e from being read and thereby effectively disabling tag 200e from transmitting memory information. In addition, logic 334 may be programmed so that when switch 332 is opened, logic 334 either sets a bit in memory 201e or otherwise indicates that tag 200e has been removed from IV bag 140.

In the alternative, another embodiment is contemplated that does not include a battery 337 and instead includes an externally powered RF assembly that has to be excited by an external source in order to send information to a controller or the like. In addition to sending information to a controller, information may also be obtainable from tag 200e by other system devices.

In this self powered embodiment, when an IV bag 140 is emptied or discontinued, tag 200e can be removed from the bag 140 by releasing connector 342 (e.g., counter turning connector 342) to open switch 332. It is anticipated that the memory 201e is erased or reprogrammed prior to tag 200e being attached to a new IV bag 140. To prevent tag 200e from being used to identify another bag prior to being reprogrammed, mechanical reset 344 may be used. To this end, in one embodiment, when connector 342 is released, tag 200e is disabled such that tag 200e will not provide information in memory 201e until connector reset 344 is reset using a special tool (not illustrated). By reserving use of the special tool to qualified individuals, proper memory 201e reprogramming can be ensured. The resetting tool can include a battery and contacts or an RFID programming circuit or some type of mechanical device. In some embodiments, when the resetting tool is used, memory 201e is also automatically erased. Other methods of isolating or disabling memory 201e between uses are contemplated.

Referring still to FIG. 8, assembly display 346 may be used to present portions of memory contents 220 or to indicate status of the device 200e (e.g., transmitting, receiving, etc.).

While the inventive system may employ any of several different types of communicating devices and protocols (including the devices and protocols described above) that enable system components to communicate and transfer information, in order to simplify this explanation, unless indicated otherwise, hereinafter, the invention will be described in the context of an RF based system where each device includes an RF communicating device to receive, transmit, or receive and transmit information from and to other system devices and also includes some type of antenna capable of receiving power from an external power source (e.g., a hand held device, a physician's badge, etc.)

D. IV Pump System

Figure 16:
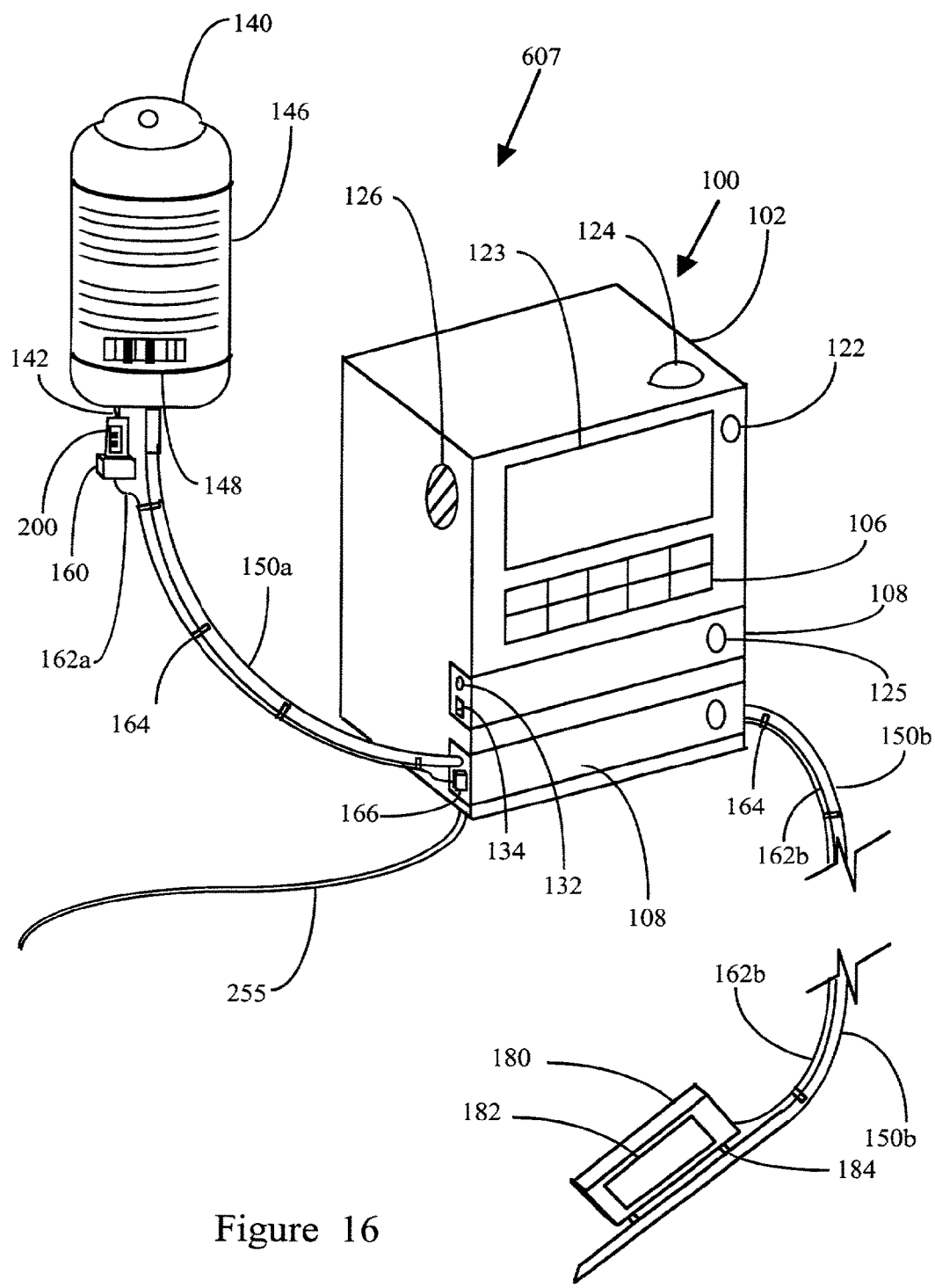
FIG. 16 is a perspective view of an IV pump assembly.

Referring now to FIG. 16, an exemplary infusion system 607 includes at least one IV bag 140 linked to an infusion pump 100 via a first line 150a where pump 100 is in turn linked to a patient (not illustrated in FIG. 16) via a second IV line 150b. Bag 140, includes an externally powered RFID tag 200 including information similar to contents 220 in FIG. 6.

Figure 17:
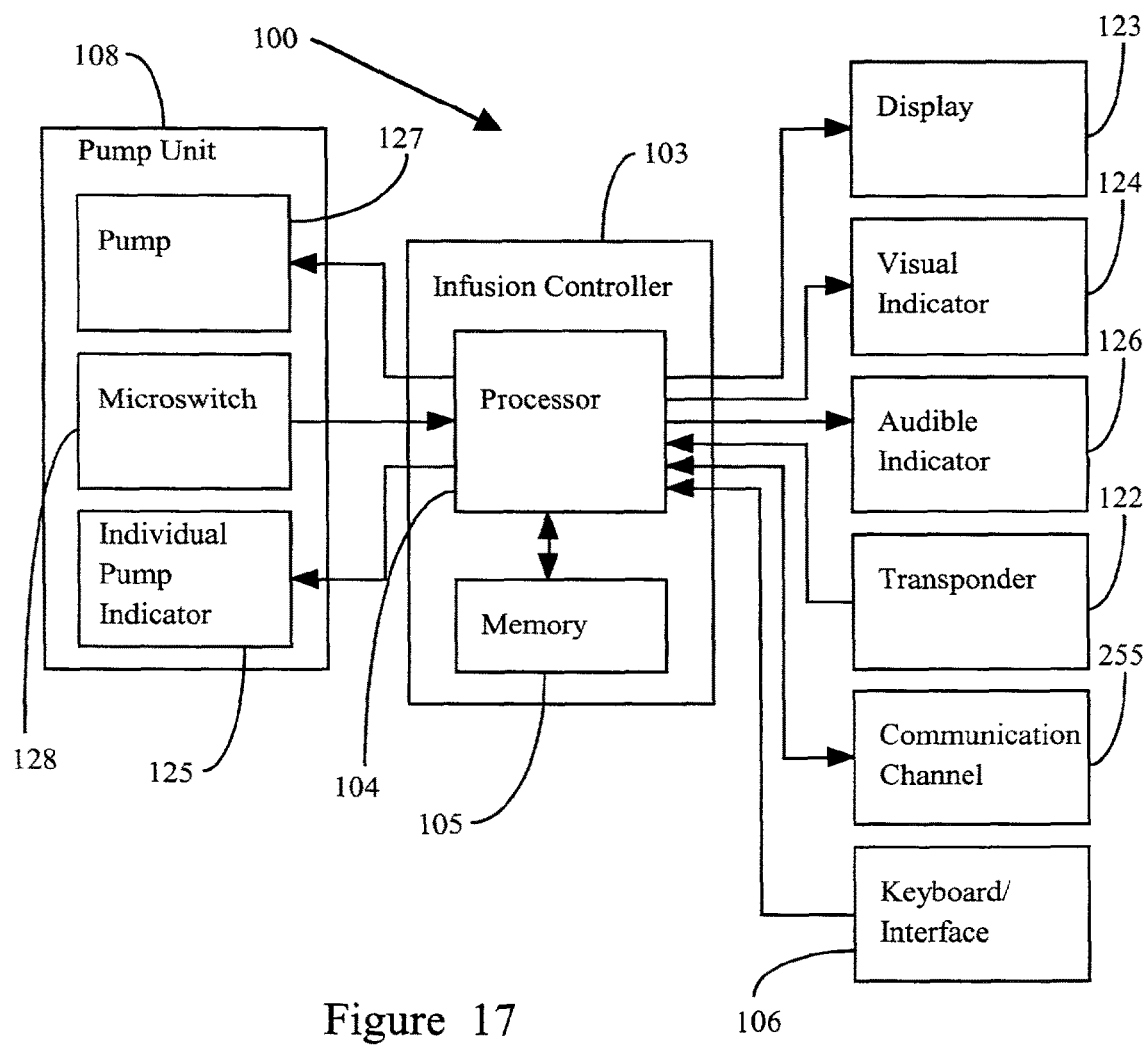
FIG. 17 is a schematic view of several of the components included in the pump of FIG. 16.

Referring also to FIG. 17, pump 100 includes a housing 102 that houses, among other things, one or more pump assemblies or units 108, an infusion controller 103, a display 123, a visual indicator 124, an audible indicator 126, a transponder 122 and an interface device, typically in the form of a keyboard 106 or mouse for controlling a display cursor, for manually providing information to a processor 104. Controller 103 includes processor 104 and a memory 105 that is accessible to processor 104 to read information from and write information to memory 105.

Each unit 108 includes a pump 127 (e.g., compression rollers, a pressure gradient suction valve, etc.), a micro switch 128, a pump specific indicator 125, a line inlet port 132 and a line outlet port (not visible in Figs. but including the port from which line 150*b* in FIG. 16 extends). In some embodiments, each unit 108 also include a data inlet port 134 and a data outlet port (again, not visible in Figs. but includes port from which data line 162*b* extends in FIG. 16). The data ports are described in more detail below. Lines 150*a* and 150*b* link corresponding unit inlet ports 132 and outlet ports (not illustrated) to IV bags 140 and a patient 12 in a conventional manner.

Referring still to FIG. 17, processor 104 is linked to each of the pump 127, switch 128 and indicator 125 for control thereof in a manner that will be described in more detail below. Switch 128 is configured and provided such that switch 128 can determine when an IV line 150*a* is connected to or removed from a corresponding pump unit 108. To this end, switch 128 may be mounted inside port 132 to mechanically sense connection and disconnection of a line 150*a*.

Display 123 is, in some embodiments, an LCD or other screen device that facilitates communication of human readable information such as text, graphics, etc., related to one or more IV processes. Visual indicator 124 is typically an LED or some other similar device which is easily viewable under all lighting conditions. Hereinafter, while other than an LED may be used as a visual indicator, unless indicated otherwise, it will be assumed that all visual indicators are LEDs. Audible indicator 126 is a speaker or beeper or some other device capable of generating sound. Transponder 122 is an RFID tag reader that can communicate with other system devices including the patient ID devices 10, physician ID devices 40, bag tags 200, etc. While transponder 122 is shown as a part of IV pump 100, transponder 122 may be connected to pump 100 via a tether.

Processor 104 is linked to each of display 123, indicators 124 and 126, transponder 122 and keyboard 106. In addition, as illustrated in FIG. 17, processor 103 is also linked to a communication channel 255 such as an intranet or the Internet for communication with other facility or remote computing and storage devices.

Infusion controller 103 controls each pump unit 108 to infuse intravenous fluids to a patient from IV bags 140. To this end, an IV bag 140 is connected to a patient via a fluid tubing line 150*a*, 150*b* that passes through one of pump units 108 to the patient.

Referring now to FIGS. 17 and 18, a "populated" (i.e., essentially completely specified) exemplary memory contents 280 of memory device 105 is illustrated. Contents 280 includes a pump identification number 130, patient information 282 and a separate memory content information segment for each pump unit 108 in pump 100. Patient information 282 may include minimal information such as a patient ID or name or may include virtually all information from a patient ID device 10 and or additional patient information obtained via communication channel 255 and a remote facility server/database. In any event, patient information 282 must be useable to uniquely identify a single patient so that pump 100 can be uniquely associated with a single patient 12.

Referring still to FIG. 18, exemplary memory content for one unit 108 includes physician information 61, IV medicant information 284, order verification information 290 and pump status information 291 (i.e., flow rate 292, duration 293, dose 294, volume to be infused 295 and volume infused 296). Memory contents 280 and how the contents are used will be explained in greater detail below.

Referring now to FIGS. 5 and 16, when an IV bag 140 is brought to a patient for infusion, the bag 140 is positioned with respect to transponder 122 and transponder 122 is activated to obtain (e.g., read) at least a subset of memory contents 220 from the tag 200 on the IV bag 140 and store a portion of the obtained memory content in controller memory 105. For instance, in the present example, as memory 201 is an RFID tag, transponder 122 is designed to read only RFID tags proximate (e.g., within 10 cm) the transponder 122. The range of sensing is limited to prevent transponder 122 from obtaining information from an RDIF tag associated with another more distal IV bag 140. In the present case range is limited by restricting the power of transponder 122 so that only RFID tags (e.g., 200) proximate the transponder are powered thereby. Consistent with the medication information 230 obtained from contents 220, pump 100 sets operating parameters for a particular pump unit 108 so that the unit 108 operates at the prescribed dosage rate and time. In effect, the processor 104 associates the pump unit with the particular infusion process prescribed by the bag tag 200.

Referring also to FIGS. 1 and 2, when medicant dosing is dependent on a patient's weight, in some embodiments pump 100 uses transponder 122 or some other sensor device to obtain (e.g., read) a portion memory contents 20 of patient identifier 10 to determine the patient's current weight 28. This reading process, like the process of reading tag memory 201 will, it is contemplated, require placement of a patient identifying device 10 proximate transponder 122 to facilitate device 10 activation and transfer via RF communication. Infusion controller processor 104 then computes the correct infusion rate based on weight 28. The patient's weight can also be obtained from the physician entering it using keyboard 106 or the weight can be obtained via communication with a hospital network by transmitting (e.g., via 802.11 wireless communication) selected patient ID information 222 to a remote facility server via network 255 where the server which correlates patient identification with most recently recorded patient conditions including weight. Upon receiving the patient identification, the server identifies the patient's weight and transmits the weight back to the controller processor 104 for use by processor 104 in determining infusion rate.

Referring still to FIGS. 2 and 16, when infusion rate or other characteristics are based on a patient's body surface area, the patient's body surface area 29 or height 27 and weight 28 which can be used to compute body surface area can be provided to processor 104 in any of the manners described above (e.g., via device 10, remote server or physician entry via board 106).

In addition to obtaining a patient's weight and other physical characteristics from a patient identification device 10, pump 100 can also use transponder 122 to obtain other specific patient information 21 including the patient identification number 22 or some other information that uniquely identifies the patient. For the purposes of this explanation it will be assumed that processor 104 obtains and stores the patient identification number 22 (see FIG. 2) from a device 10. After obtaining the patient identification number 22, processor 104 may be programmed to associate the pump 100 with the patient ID by storing the patient identification number 22 in memory 105 as number 130 (see FIG. 18).

After a pump 100 is associated with a specific patient (e.g., via number 130 stored in controller memory 105), upon obtaining information from an IV bag 140 including the patient identification number 223 that indicates the patient for which a medicant in corresponding bag was dispensed, processor 104 can compare the patient number 130 stored in memory 105 with the number 223 obtained from the bag 140 to determine if the medicant in the IV bag 140 was dispensed for delivery to the patient 12 associated with the pump 100 (i.e., the patient whose ID device 10 was most recently used to associate the pump). If the number 130 stored in pump memory 105 and the number 223 obtained from the IV bag do not match, processor 104 can alert an attending physician of the mismatch via display 123 or some other suitable device. If the compared numbers are identical, processor 104 may proceed to facilitate medicant delivery to the patient (i.e., may enable a pump unit corresponding to the medicant, unlock a compartment (not illustrated) on an infusion pump unit 108 to allow the IV bag 140 to be mounted thereon, and/or provide an audible or visual indication to the attending physician).

Other comparisons are contemplated for the purpose of facilitating other health safety functions. For instance, referring again to FIGS. 2, 6 and 16, processor 104 may obtain allergy information 24 (i.e., an indication of medicants that the patient is allergic to) from a patient's ID device 10 (see also FIG. 1) and may also obtain the medicant name and number 236 from an IV bag memory 201. In this case, prior to enabling delivery of medicant in a bag 140 to a patient, processor 104 may compare the list of medicants 24 to which the patient 12 is allergic with medication 236. Here, assuming the pump has already been associated with a patient (e.g., in the case of a multiple line pump), patient information from the patient identification device 10 need not be obtained a second time to perform this comparison. If the patient 12 is allergic to the medicant, processor 104 may alert an attending physician. If the patient is not allergic to the medicant, the processor may facilitate medicant delivery to the patient. In a particularly advantageous system, where the patient is not allergic to the medicant, the processor 104 affirmatively indicates that no allergies were identified thereby giving the patient and the attending physician some peace of mind regarding potential allergy problems.

As another comparison instance, processor 104 may be programmed to compare a total volume of medicant to be delivered during a period to a patient to a maximum allowable or safe volume over that period and, where the total intended to be delivered exceeds the allowable volume, may activate an alert and/or disable the units until a physician affirmatively bypasses the safety mechanism. To this end, where total allowable volume is dependent on patient weight or other characteristics, processor 104 may obtain the relevant characteristics from device 10, determine the allowable volume to determine how to proceed. In the alternative, after obtaining patient ID information from device 10 processor 104 may access other relevant information via channel 255.

Prior to authorizing or facilitating medicant dispensation to a patient, pump 100 may also require that a physician having specific training or responsibilities be present to administer the medicant. To this end, referring again to FIGS. 3, 4, 16, 17 and 18, pump 100 may determine that an appropriately credentialed physician is in attendance prior to commencing medicant delivery by requiring that physician information 61 be obtained by processor 104 from a physician's identification device 40 and compared to physician information in memory 105 or which is remotely accessible via channel 255 and which indicates required credentials. Here, it is contemplated that, just as transponder 122 can obtain information from patient identification device 10, so to can transponder 122 obtain information from a physician's identification device 40 either via RF or some other communication protocol.

Once physician information 61 is obtained from a device 40, information 61 can be compared with the required credentials information already stored in memory 105 to determine if the physician is authorized to dispense the medicant to the patient. Where the physician is appropriately credentialed, again processor 104 can facilitate delivery to the patient. Where the physician is not properly credentialed, processor 104 can indicate so. Physician credentials may be a function of any of several different factors including the patient identification (i.e., for a specific patient perhaps only one physician is authorized to administer medicant), medicant type (i.e., for a specific medicant, perhaps only two physicians at a facility are authorized to administer), etc.

While infusion control information is described above as being stored on separate bag tags 200, in at least some embodiments infusion control information may be stored on the patient identification device 10. In this case, upon obtaining information from a device 10, processor 104 may store the obtained information including the control information. Thereafter, when a bag is brought to the patient for administration, processor 104 may obtain only medicant identifying information form the bag and then determine, based on a comparison of the information from the device 10, whether or not the medicant should be delivered to the patient and if so, may use information from device 10 to set delivery parameters.

In all cases where communication is established between two components in an infusion system or where information is transferred form one system device to another, it is contemplated that system devices involved in the communication or transfer may be programmed to indicate, either visually or audibly, that the device is involved in the communication or transmission. This feature is contemplated as a way to ensure that during communications and transfers, a physician does not inadvertently and mistakenly communicate with an unintended device in proximity of a patient 12. For instance, in the present case where system devices communicate via RF communication, assume that, to initiate a data transfer, a physician depresses one of the keys on keyboard 106. In this case, where the physician wishes to transfer information form a patient device 10 to a pump memory 105 to associate the pump with the patient and for comparison and/or control purposes, the physician first positions the device 10 and transponder 122 in relative positions that should enable information transfer. Thereafter, the physician presses the data transfer initiation key on board 106 causing transponder 122 to request information from device 10. When the request is received by device 10, device 10 activates interface 18 to visually indicate that device 10 received the request. The physician visually confirms that device 10 that the physician intended to obtain information from is the device that generates the visual indication. This confirmation process avoids the possibility that information could be obtained form some other patient identification device 10 in the viscidity of transponder 122. Thereafter device 10 transmits information to transponder 122 via RF communication.

When information is received by transponder 122, processor 104 may cause display 123 or speaker 126 to indicate that information is being received. For instance, all received information may be displayed on screen 123 so that the physician can visually confirm basic information (e.g., patient name, general physical characteristics, etc.) Confirmation information (e.g., an acceptance of transmitted information by a physician) may be recorded in pump memory 105 for later transmission to a database.

As another example, referring again to FIGS. 8 and 16, when a tag 200e receives an information request, tag 200e may indicate reception by indicating via display 346 or some other indicator (e.g., an LED).

Instead of using patient device 10 information to associate a pump 100 with a specific patient 12, information from a bag tag 200 may be employed. To this end, assuming that a pump 100 is initially not associated with a particular patient, when a first bag tag 200 is interrogated by transponder 122, processor 104 may obtain patient identification information from the first bag and store that identification information in memory 105 to establish association. Thereafter, until the association is discontinued, whenever subsequent bags 140 are brought to the patient 12 for medicant delivery, information is obtained from the tags 200 on the subsequent bags 140 and is compared to the information in memory 105 that identifies the associated patient. The interrogation process is similar to the process described above (e.g., may include allergy comparison, physician identification comparison, etc.) prior to facilitating medicant delivery. In this manner, the first IV bag 140 attached to an infusion pump 100 effectively assigns the pump 100 for use with a single patient 12 and no other patient until the association is terminated, thereby assuring that the patient 12 receives only medicants dispensed for that patient 12.

Typically an IV pump 100 will not be turned off until the medicant being delivered by the pump 100 is to be discontinued. To avoid using information in a pump memory 105 to deliver medicant inadvertently as a function of stale information in memory 105, in at least some embodiments of the invention, when IV pump 100 is turned off, patient information 130, 282 (see FIG. 18) is erased from memory 105. After memory 105 has been cleared in this manner, if a physician desires to begin delivery of the medicant to the patient again, the pump can again be turned on and the association process and comparison processes described above can be repeated. If the pump 100 is to be used with a second patient, another association and interrogation process involving the second patient and other medicant bags 140 must be performed. It is also contemplated that some key on board 106 may facilitate manual erasing of memory 105.

Referring again to FIG. 16, system 607 includes line sensors 128 for sensing when an IV bag is linked to a specific pump unit 108. In these cases, processor 104 can receive an indication from a sensor 128 that a line has been linked to or removed from a pump unit 108 and then can perform some function based on the status of liked lines. In some embodiments, when a line is removed from a unit 108, the information stored in memory 105 corresponding to the specific unit 108 is erased so that the information is not inadvertently used to control delivery of a medicant in a subsequent IV bag 140.

Thus, when another bag is brought to the patient for delivery, an association and programming process is repeated to set parameters for delivery of the medicant in the new bag. Similarly, when a final IV line 150a is detached from a pump 100, the pump 100 should be disassociated from the previously associated patient 12 so that the pump 100 can be used with another patient. To this end, in at least some embodiments, when a final line is detached from pump 100, processor 104 may be programmed to erase or clear the memory 105 to effectively disassociate the patient 12 and the pump 100.

Similarly, when a line 150a is initially plugged into a unit inlet 132 and is sensed by a switch 128, processor 104 determines if the pump 100 has been associated with a specific patient. Where pump 100 has not been associated with a specific patient 12, processor 104 can instruct an attending physician to use transponder 122 to obtain patient information from some other device. For instance, transponder 122 may be used to obtain patient information form a patient device 10. In the alternative, transponder 122 may be used to obtain patient information from the bag tag 200. After processor 104 obtains the patient information, processor 104 stores the information in memory 105 (see also FIG. 17) to establish an association between pump 100 and the patient 12. In addition, after associating the pump 100 with a patient, processor 104 automatically obtains medicant and prescription information (hereinafter "unit control information") from tag 200 and store that information in memory 105 to control the specific unit 108 linked via line 150a.

In embodiments that do not include sensors 128, a pump unit start key (e.g., one of the keys on board 106) may be pressed to indicate that a new line is being linked to a pump unit 108 and the process described above may be repeated to determine if the pump is associated with a patient and to obtain unit control information and associate a pump unit with a specific medicant bag and the control information.

In some embodiments, when an initial IV bag 140 is detached from a pump unit 108, even when the initial bag 140 comprises the last bag 140 attached to pump 100, there can be circumstances wherein preserving memory contents 280 is desirable. For example, when an initial bag 140 is to be detached form a unit 108 and replaced with a replacement bag 140 and the replacement bag either includes the same medicant as the initial bag or was issued under the same order as the initial bag 140, it may be advantageous to maintain existing infusion process parameters (i.e., parameters corresponding to the initial bag) when the replacement bag is linked to the unit 108. This parameter maintenance feature is especially useful when medicant delivery parameters have been titrated or modified in response to the patient's condition.

To facilitate this feature, when a line is detached from a unit 108, processor 104 may be programmed to maintain the parameter settings for the specific unit until information can be obtained from the replacement bag and compared to the information corresponding to the initial bag 140. Where the replacement bag medicant or unit control information is unrelated to similar information corresponding to the initial bag, processor 104 can then erase information related to the initial bag from memory 105 and replace that information with the unit control information obtained from the replacement bag 140 thereby associating the pump unit 108 with the new bag and corresponding control regimen. However, where the replacement bag unit control information and medicant are related to or are an extension of similar information corresponding to the initial bag, processor 104 can maintain the control parameters to control delivery of the medicant in the replacement bag. In the alternative, after processor 104 has identified a relationship between the initial and replacement bags, processor 104 may prompt an attending physician to affirm that the physician would like to continue with the previous flow rate 292, duration 293, dose 294, etc. To this end, processor 104 may indicate the previous parameter settings via display 123 and provide icons via display 123 to accept, reject or adjust the settings.

While, in most cases, it is desirable to request bag tag 200 contents 220 and specific patient information 21 to ensure that a medicant is supposed to be delivered to a patient 12 prior to delivery, there are circumstances in which the delay required to obtain this type of information is particularly undesirable (e.g. a STAT or emergency condition) and in which pump 100 should be allowed to operate without requiring this information. To this end, another feature of the inventive system is that one of the keys or a specific key code on board 106 may be selectable to avoid having to perform the protocol described above in emergency situations.

Referring to FIGS. 16 and 17, in single pump systems, processor 104 can determine that a bag 140 includes medicant for a particular patient 12 using several different protocols. According to one method described above, transponder 122 can be used to obtain patient identification information from device 10 and patient identification information from tag 200 memory content 220 and then determine if there is a match between the two patient identification sets.

Figure 19:
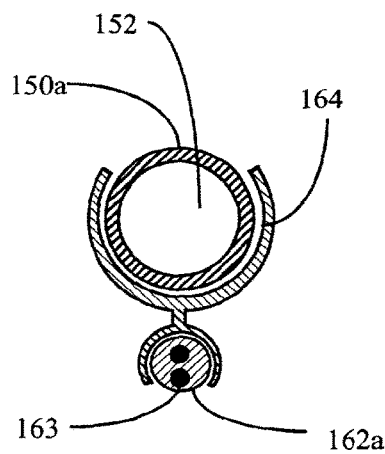
FIG. 19 is a cross-sectional view of one of the lines and data buses of FIG. 16.
Figure 20:
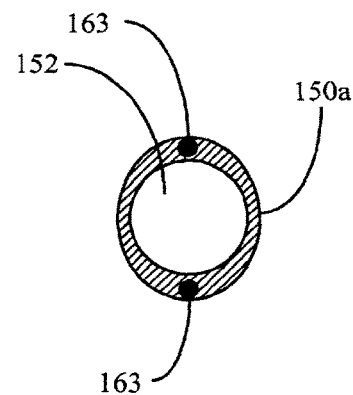
FIG. 20 is a cross-sectional view of another embodiment of a combined IV line and data bus assembly.

In another embodiment, referring still to FIGS. 16 and 17, a tag reader 160 may be provided that is linked via a data bus 162 to a connector 166 that is received within data port 134 of a unit 108. In the illustrated embodiment bus 162*a* is connected to line 150*a* via clips 164 (e.g., pressure fit or glued) that are essentially equispaced along line 150*a*. Referring also to FIG. 19, bus 162*a* is composed of wires 163 surrounded in a conventional manner with an electrical insulator. Using this arrangement bus 162*a* is easily associated with a specific IV bag 140.

In the present example, reader 160 is an RF reader capable of reading or receiving information from tag 200. Information obtained by reader 160 is provided to processor 104 (see also FIG. 18) via bus 162*a* and port 134 and can be used in the manner described above to compare and set parameters.

Figure 21:
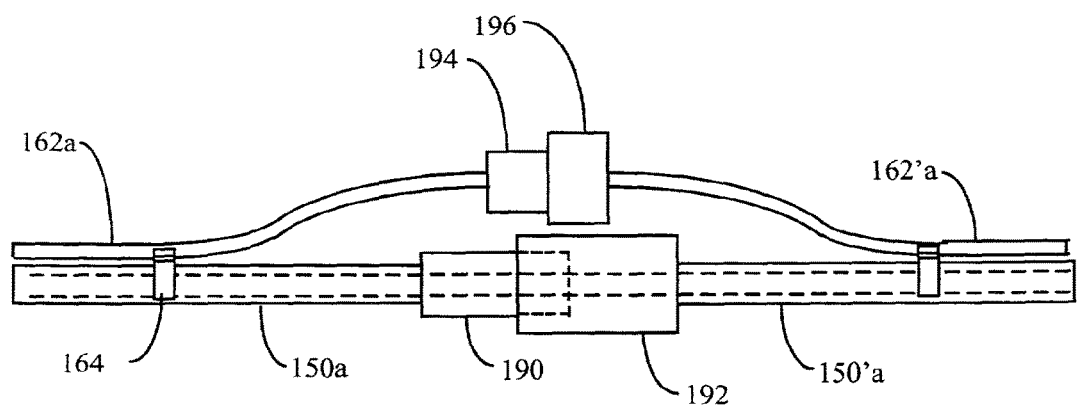
FIG. 21 is a plan view of a connector configuration used to connect two lines that are similar to the line illustrated in FIG. 19.
Figure 22:
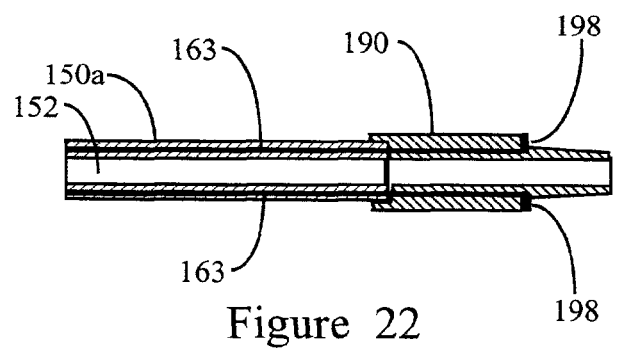
FIG. 22 is a cross-sectional view of another line embodiment.
Figure 23:
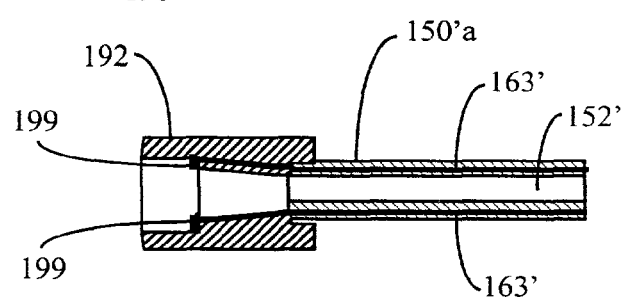
FIG. 23 is a cross-sectional view of another line embodiment.
Figure 24:
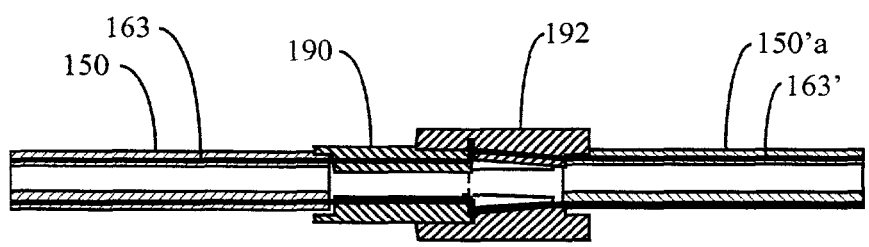
FIG. 24 is a cross-sectional view of a connector configuration used with the line similar to the line illustrated in FIG. 23.
Figure 25:
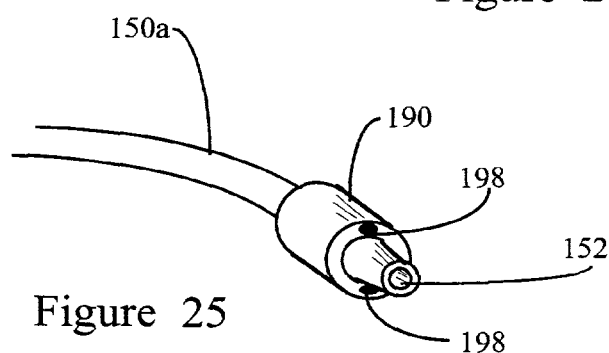
FIG. 25 is a perspective view of an end of the line illustrated in FIG. 24.

In the illustrated embodiment bus 162 can only be separated from line 150*a* a short distance so that reader 160 and connector 166 can only be connected to the same bag 140 and the same pump unit 108 as line 150*a*, respectively. Similarly, referring also to FIG. 21, bus 162*a* may be mated to a second bus 162*a*' associated with another line 150*a*' via electrical connectors 194 and 196 that mechanically limit the ways in which the two buses 162*a* and 162*a*' can be linked. In FIG. 21, mechanical limitation is facilitated by way of limiting the portion of slack bus lines 162*a* and 162*a*' to small distances to render incorrect cross connections essentially impossible. Because bus 162*a* is not physically part of line 150*a*, bus 162*a* can be detached from line 150*a* and reused.

Referring still to FIG. 16, a second data bus 162*b* is linked to a portion of the IV line 150*b* that extends form pump 100 to the patient 12. Bus 162*b* has a construction similar to the construction of bus 162*a* and operates in a similar manner to facilitate transfer of information from pump 100 to a line identification device 180 that is clipped to line 150*b* via clips 184. Device 180 includes a display 182 so that device 180 can display any information in memory 105 including medication name or other information for a corresponding line 150*b* at a point nearer to the patient 12 than pump 100. Device 180 is especially useful when multiple IV bags and lines are used on one patient. Devices 180 can be used by a physician to easily and accurately determine which of several lines linked to a patient should be removed when one or more lines are to be detached from the patient. To this end, a physician may use pump 100 to indicate one medicant to be discontinued. The pump processor 104, tracking which units correspond to which medicants, can send a signal to a device 180 corresponding to the medicant to be discontinued thereby causing the device 180 to indicate (e.g., the beeping LED) the specific line to be detached from the patient 12.

Referring now to FIGS. 20, 22, 23, 24, and 25, a second embodiment of a combined line and bus is illustrated. In this embodiment, wires 163 are embedded within the walls that form the lumen 152 of line 150*a*. Line 150 is matable to a second line 150' via a conventional Luer Lok fluid connection composed of a female portion 190 and a male portion 192. Female portion 190 includes electrical contacts 198 and male portion 192 includes electrical contacts 199 arranged so that when the female 190 and male 192 portions are connected there is electrical contact between contacts 198 and 199 creating a link between wires 163 and 163'. Where wires 163 are embedded within line 150*a*, sensor 160 may be detachable from line 150*a* to facilitate reuse.

Referring again to FIGS. 1-4 and 16-18, in yet another embodiment physician identification device 40 may be used to obtain memory content 20 from a patient device 10 and to also obtain tag information from tag 200 on a bag 140. The information from device 10 and tag 200 can then be transferred to pump 100 and processor 104 via transponder 122 and processor 104 can perform the comparison, associating and parameter setting protocols described above when appropriate. Here, as above, virtually any of the transfers of information or communications may be indicated by one or both devices involved indicating the occurrence via an audible or a visual indication.

In one other embodiment where a physician uses device 40 to obtain information from memory content 20 of device 10 and from content 220 of a tag 200, device 40 may be programmed to determine if there is match between the patient information 21 from device 10 and the patient information 222 from tag 200. Where the compared information matches, device 40 may transfer at least a subset of the information to pump 100 to establish association between the pump 100 and the patient 12 and also to set unit 108 operating parameters as described above.

In the case of standard IV medications that are stored as floor stock (i.e., medicants that needn't be released by a pharmacist), memory content 220 typically will not include patient information 222 (see FIG. 18) and therefore no comparison between patient information will be possible. In these cases, when tag information is obtained, processor 104 should be able to recognize the medicant identified by the tag information as floor stock and facilitate delivery without a match of patient identification information.

Referring still to FIG. 16, each pump unit 108 includes its own indicator 125, which may be in the form of a light or LED, visible on the exterior of housing 102. Referring also to FIG. 17, in some embodiments processor 104 is programmed to indicate specific units 108 via indicators 125 under certain circumstances. For example, instead of indicating a line 162*b* via interface 180, when keyboard 106 is used to identify one of several medicants linked to pump 100 and a patient 12, processor 104 may be programmed to illuminate an indicator 125 associated with the unit 108 linked to the particular medicant. Similarly, assuming no lines are initially linked to pump 100, when tag 200 information is obtained, processor 104 may illuminate a unit 108 to which the corresponding bag is to be linked to ensure that unit control information is used to control delivery of a medicant in an associated bag.

Figure 30:
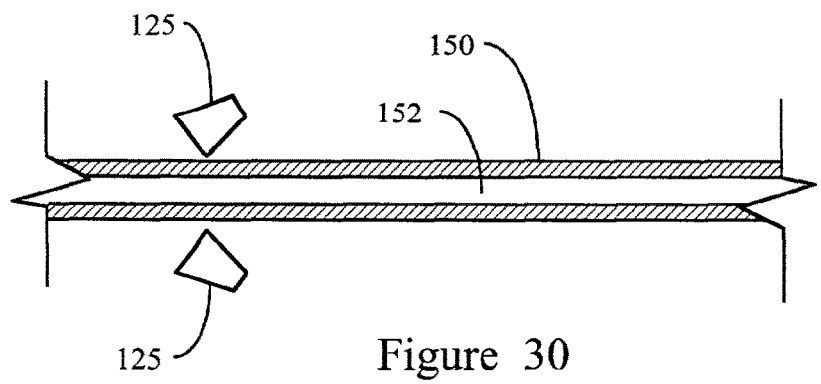
FIG. 30 is a cross-sectional schematic view of a line according to another aspect of the present invention.

Referring also to FIG. 30, in other embodiments, indicator 125 may be positioned within a line receiving port 132 and configured as one or more lights that shine on one or both of lines 150*a* or 150*b*. In this case, as in the case of a light pipe, indicator 125 light is transmitted from unit 108 toward either a linked bag 140 or a patient (not illustrated) and can be used to distinguish one line from another. Here, in at least one embodiment, different colors of light may be provided to lines linked to separate units 108. For instance, lines linked to a first unit 108 may be illuminated with a white light while lines linked to a second unit 108 may be illuminated with a blue light. In the alternative, light may be blinked on and off among separate units in a sequence to allow all line linkages to be identified in a short light cycle. For instance, for a pump including four separate units 108, during a first second of a four second cycle, indicators 125 may illuminate lines linked to a first unit 108. During a second of the cycle indicators may illuminate lines linked to a second unit 108 with all other indicators off. During the third and fourth seconds only indicators corresponding to the third and fourth units 108, respectively, may be illuminated. This cycle may be repeated several times to help a physician distinguish lines. The cycles may be initiated via a command entered via board 106 or in some other manner (e.g., using a physician badge 40 to request line identification).

E. Multiple IV Pump Configurations

Figure 26:
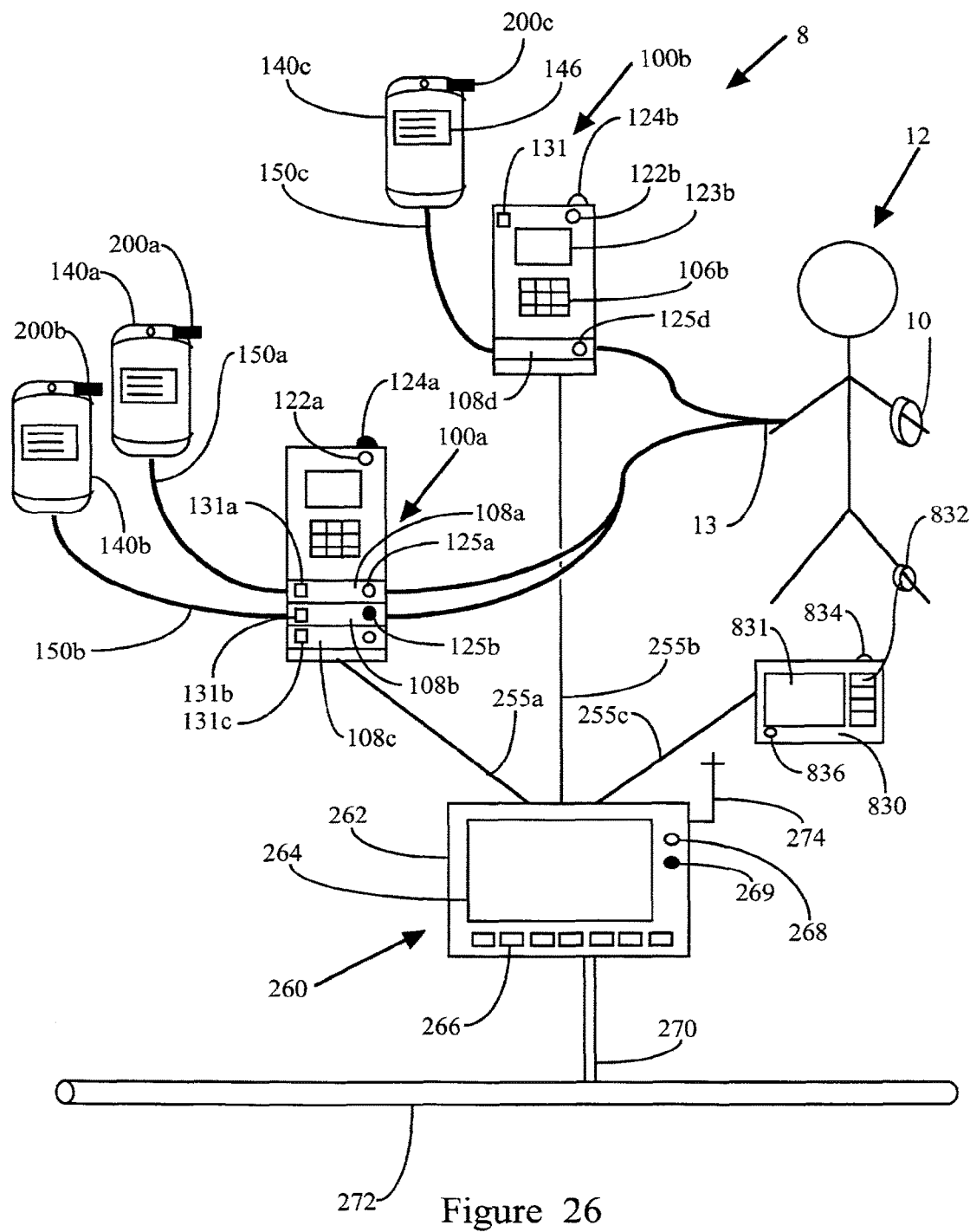
FIG. 26 is a schematic view of an IV system according to one embodiment of the present invention.

Referring now to FIG. 26, an IV system 8 including several IV pumps 100a and 100b, a centralized IV pump controller 260 and both physician and patient identifying devices 40 and 10, respectively, is illustrated. Each of pumps 100a and 100b is similar to pump 100 described with reference to FIGS. 16, 17 and 18 above and therefore, only distinctions between pumps 100a and 100b and pump 100 will be described here in detail. In addition, unless indicated otherwise, because pumps 100a and 100b are similar, only pump 100a and its operation will be described unless indicated otherwise. The main difference between pumps 100a and 100b is that pump 100a is a multi-unit pump whereas pump 100b is a single unit pump. Because pump 100b is a single unit pump, a single machine readable indicia 131 identifies the pump 100b as a whole whereas similar indicia 131c, 131b, etc. on pump 100a are associated with and identify separate pump units 108a, 108b, etc.

With respect to construction and capabilities, it should suffice to say that, in this embodiment, pump 100a includes several pump units 108a and 108b, 108c, each unit linkable to a separate IV bag (e.g., 140a) and to a patient 12 to deliver medicant from a bag 140a to the patient 12 in a regulated manner. To regulate units 108a, etc., pump 100a includes the components illustrated in FIG. 17.

Each pump unit (e.g., 108a, etc.) includes among other things, a separate unit indicator, a line inlet and a corresponding line outlet. For instance, unit 108a includes indicator 125a, an unnumbered inlet and an unnumbered outlet. In addition, although not illustrated in FIG. 26, referring again to FIG. 16, each unit 108a, 108b, etc., may also include a data inlet 134 for receiving data from a bag tag sensor 160.

In addition to the components above, each pump 100a and 100b further includes a pump transponder 122a, 122b and a pump specific indicator 124a and 125b (note displays 123 could also be used as pump specific indicators), respectively, that operate in the manner described above.

Referring still to FIG. 26, devices 40 and 10 are similar to the devices described above with respect to FIGS. 1 through 4 and therefore will not be explained again here in detail. To the extent that devices 10 and 40 operate differently than described above, the other operations will be described below.

Figure 26A:
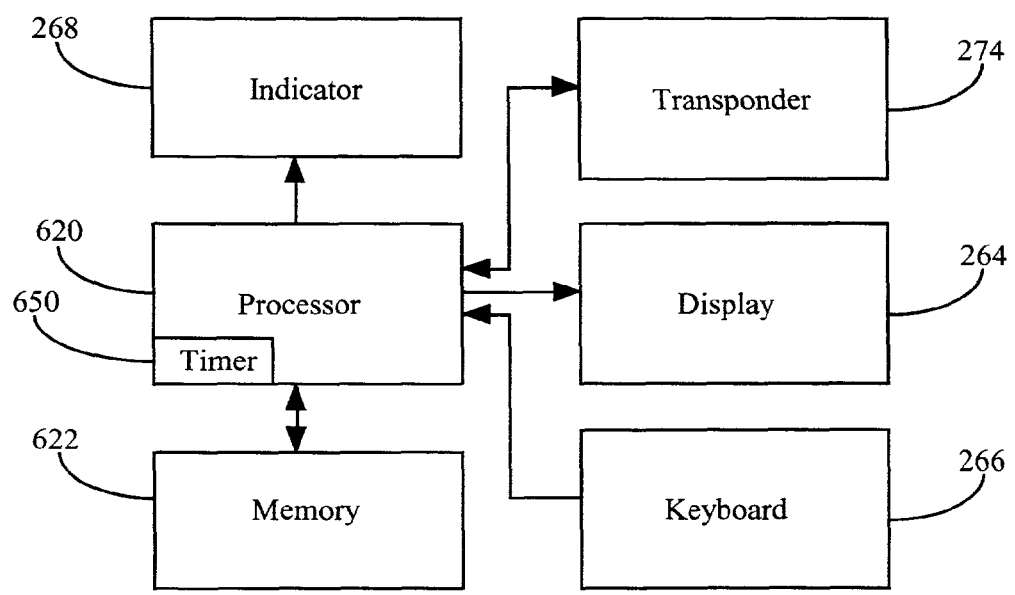
FIG. 26A is a schematic diagram of the components of the controller in FIG. 26.

Referring now to FIG. 26 and also to FIG. 26A, controller 260 includes a housing 262 that houses a processor 620, a memory 622, a transponder 274, a display 264, a keyboard 266, and an indicator 268. Processor 620 is linked to each of memory 622 and transponder 274 for two-way communication, is linked to display 264 and indicator 268 to provide output and is linked to board 266 to receive input from a controller user (e.g., a physician).

Display 264 is a textual and graphics display which can be used to examine information provided by processor 620. Indicator 268 is some type of light emitter (e.g., an LED) that is easily observable to a controller 260 user. Board 266 includes keys necessary to facilitate the functions described herein. While separate keys are illustrated, in at least one embodiment, the keys may take the form of touch screen keys or screen icons selectable via a joystick controlled cursor or the like.

Transponder 274 is a wireless transmitter/receiver for communicating via RF communication in the present example although other communication protocols are contemplated (e.g., an IRDA protocol, a Bluetooth protocol, etc.). Transponder 274 communicates via wireless communication with each of network 272, pumps 100a and 100b, physician device 40, patient device 10 and tags 200a, 200b, etc.

While a preferred embodiment of controller 260 communicates via wireless communication, it should be appreciated that in some embodiments, controller 260 may be linked via communication channels such as wire cables or the like to each of pumps 100a and 100b and to network 272. Exemplary channels are identified by channels 255a and 255b and link 270. Nevertheless, hereinafter, to simplify this explanation, controller 260 and other components will be described as being equipped to communicate via wireless communication unless indicated otherwise.

Generally, it has been recognized that by tying all system 8 components together for control by a single controller 260, a coherent and easy to administer IV delivery protocol can be facilitated where the likelihood of inadvertent or malicious mismedication can be appreciably reduced. To this end, as in the single pump case of the systems described above, an important aspect of system 8 is the concept of associating various system components together and with a particular patient 12. In system 8, this means that system devices identify each other as related to a particular patient and store system identifications (e.g., ID numbers or addresses) for subsequent communication. Examples of how system 8 devices can be used together to facilitate the inventive functions are instructive.

In a first example, assume that each of pumps 100a and 100b have already been associated with patient 12 via one of the processes indicated above (e.g., reading and storing patient information from device 10) and that bags 140a and 140c are linked to patient 12 so that units 108d and 108e are delivering medicants to patient 12. Also assume controller 260 is a mobile controller which may be either a personal computer, a personal digital assistant (PDA) or some other hand held device (HHD).

When a physician enters patient 12's room with controller 260, assume the physician wants to quickly determine the status (i.e., delivery parameters) of medicants being delivered to patient 12. Furthermore, assume a second patient (not illustrated) is also located within patient 12's room and that the second patient is also-linked to two separate IV pumps (also not illustrated) referred to hereinafter as the "other pumps." Moreover, assume that initially each pump providing medicant to the patient 12 has already been associated with the patient via storage of a patient ID 22 from device 10 or in some other fashion so that patient information is stored in the pump memory (e.g., 105 in FIG. 17). The other patient in patient 12's room will be referred to hereinafter as the "other patient."

Figure 35:
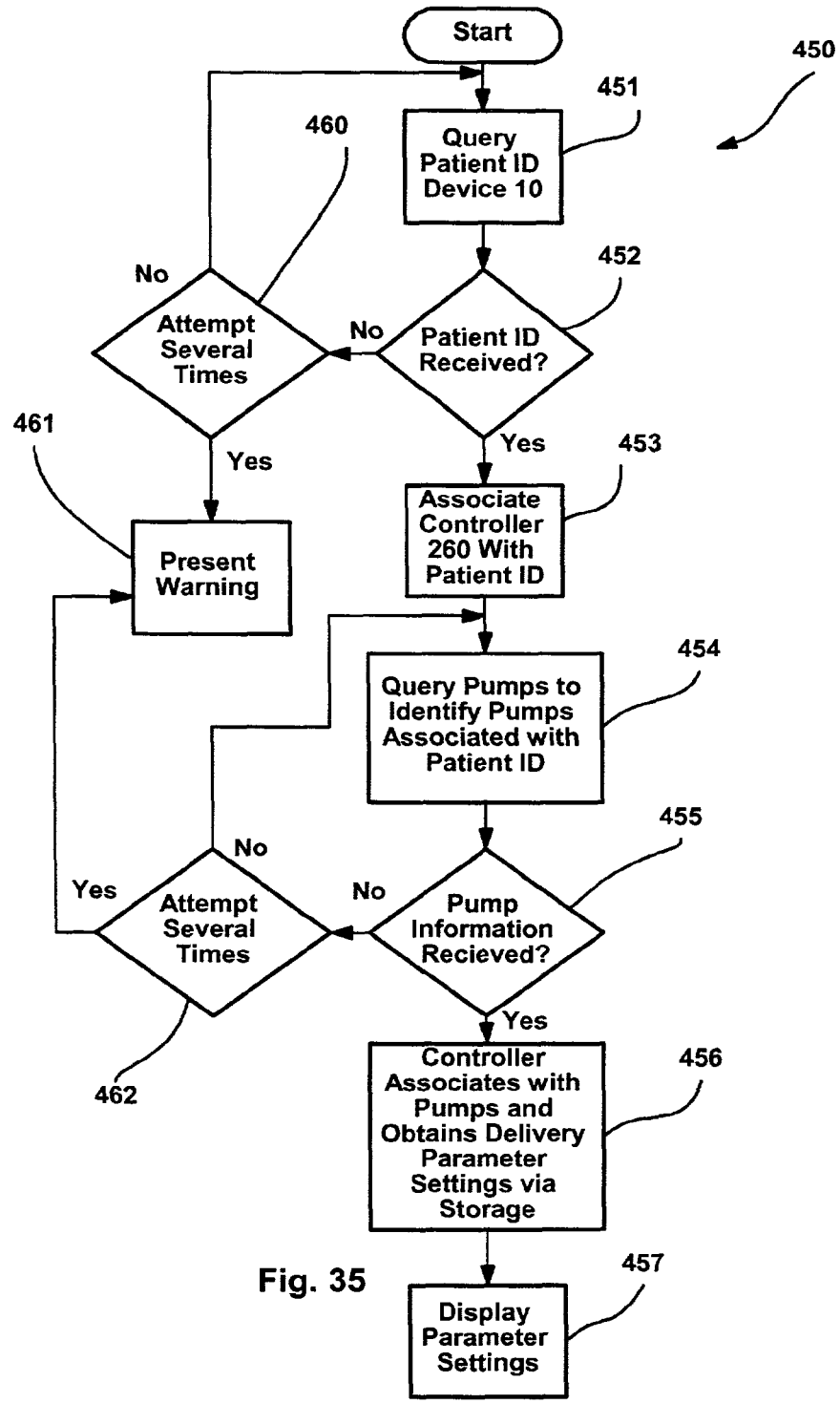
FIG. 35 is a flow chart illustrating one inventive method.
Figure 36:
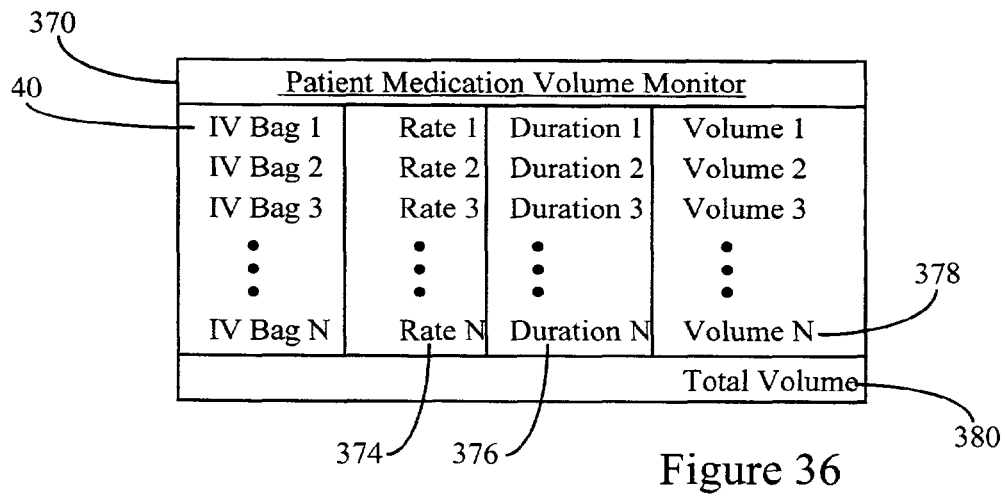
FIG. 36 is a schematic diagram illustrating data stored in a controller memory.

An exemplary method 450 of obtaining and reviewing infusion delivery parameters is illustrated in FIG. 35. In this case, when the physician enters patient 12's room, at process block 451, the physician first uses controller 260 to identify patient 12 and associate controller 260 temporarily with patient 12. To this end, the physician places controller 260 proximate patient device 10 and obtains patient identifying information (e.g., see patient ID number 22 in FIG. 2) therefrom. The step of obtaining information may take any of several different forms (e.g., receiving a periodic "heart beat" identification signal from device 10, reading information from device 10, etc.) but preferably includes the physician activating a button on keyboard 266 to excite device 10, device 10 responding by transmitting the patient ID 22 and perhaps other information to transponder 274 and controller processor 620 receiving and storing the ID 22 in memory 622.

To minimize the possibility of the physician obtaining the other patient's ID, signal transmission power for each of controller 260, device 10 and other system 8 devices can be limited so that communication is only possible over short distances. In addition, as described above, all communications may be confirmed via indicators such as LEDs or other visual or audible indications. At block 452, where no ID is received, controller 260 continues to query for the ID from a proximate device 10. After several unsuccessful attempts to obtain information from a device 10, controller 260 causes a warning (e.g., activates an LED) indicating that information cannot be obtained at block 461. Where a patient ID 22 is received, at block 453 controller 260 stored the ID in memory 622 and is thereby temporarily associated with patient 12.

Next to complete the process of determining the status of medicants being delivered to patient 12, the physician uses board 266 to instruct controller 260 to identify all pumps (e.g., 100a) that are associated with patient 12 and to obtain current pump unit status information therefrom. When so instructed, at block 454 controller 260 transmits via transponder 274 a query to all pumps within the patient's room where the query identifies patient 12 (e.g., via ID 22) and requests pump unit information. In addition to including the patient ID and the type of information required, the query also indicates the specific controller 260 via a unique controller ID. The controller ID may be a system 8 address.

Upon receiving the query from controller 260, each pump 100a, 100b and the other pumps within the patient 12's room, compares the patient ID 22 in the query to the patient ID stored in the pump memory 105 to determine if there is a match. Where a pump 100a, etc., is associated with patient 12, the pump accesses the requested information (e.g., current unit 108a status), formulates a response targeting the controller 260 by controller ID where the response includes the required information and also a separate system address (e.g., an ID number) corresponding to each pump unit (e.g., 108a) associated with patient 12 and transmits the response to controller 260. In addition, each pump 100a, 100b, etc. that is associated with patient 12 may also store the controller ID address in memory 105 to facilitate subsequent communications with controller 260.

At block 455, where no response to the query is received, control passes to block 462 were controller 260 queries several more times attempting to identify any pumps associated with patient 12. Where no response results, at block 461, controller 200 generates a warning indicating that the information sought is not obtainable. Upon receiving a response at block 455, controller 260 separates the responses according to pump units (e.g., 108a) and stores the received information along with pump unit identification information at block 456. Thus, at this point, controller 260 is associated with specific pump units and patient 12. The process of polling pumps to identify pump units associated with patient 12 may be repeated periodically (e.g., every five minutes) to reconfirm association and also to identify additional units that have been associated with the patient in the interim. Thus, if an additional medicant is linked to patient 12, when the polling process is next repeated, controller 260 identifies the additional medicant and associates with the corresponding pump unit.

It should be appreciated that the process of associating various devices with a particular patient obviates the need to store device addresses for subsequent communication. For instance, upon receiving a query from controller 260 regarding patient 12, if each pump associated with patient 12 generates a response indicating patient 12, controller 260 may be programmed to receive and store only responses associated with patient 12. As another instance, pumps may be programmed so that only pumps associated with the patient identified in a query respond and in this case the responses may not identify either the patient ID or the intended receiving controller. In this case controller 260 would be programmed to assume that all responding pumps are associated with the patient 12, while certainly a less secure obtaining protocol, this protocol is nevertheless contemplated by the present invention. Control protocols are described in more detail below.

Figure 27:
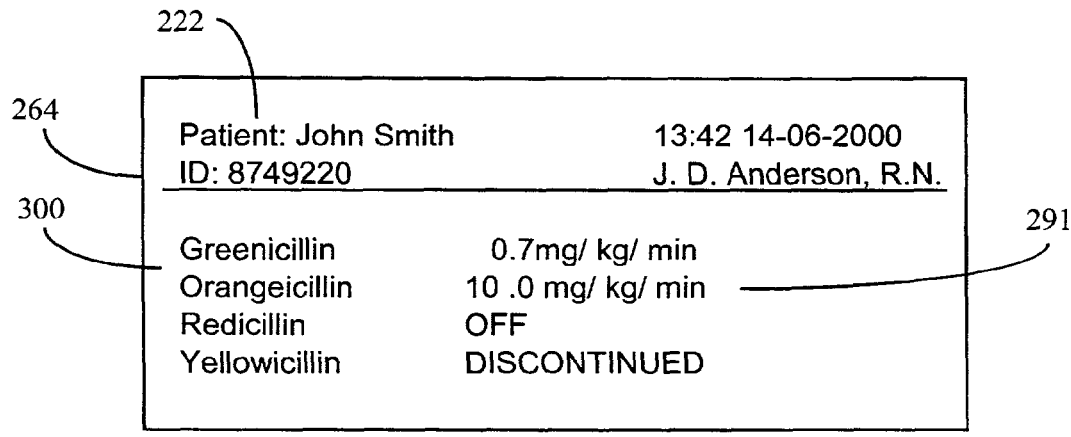
FIG. 27 is an exemplary screen shot that may be provided via the display in FIG. 26.

In addition, in several embodiments, controller 260 organizes all received responses into formats that are easy for the physician to read and provides the information at block 457. For instance, referring to FIG. 27, an exemplary screen shot of information that may be provided to a physician via screen 264 is provided. In FIG. 27, specific patient identification information 222 identifying patient 12 is provided at the top of the shot along with a current time. In addition, medicant information identifying current medicant delivery status is provided. The medicant information identifies each medicant 300 currently linked to patient 12 along with pump unit status 291 indicating current delivery rate. For instance, medicant Greenicillin is currently being delivered to John Smith at a rate of 0.7 mg./kg./min. while Redicillin is currently turned off. Also shown on FIG. 27 is a physician indicator (under the date/time, i.e., in this case, "J. D. Anderson, R.N.") indicating a physician currently using controller 260.

Referring still to FIGS. 26 and 27, providing a single display 264 via a single controller 260 expedites the process of determining medicant delivery status and minimizes status confusion. Without a centralized controller, the physician would have, at a minimum, had to confirm which pumps were linked to patient 12 and determined the status of each separate pump unit (e.g., 108a, 108b, etc.) by examining each of several different pump displays (e.g., display 123b).

It is also contemplated that controller 260 may be used to drill down further into information associated with each pump unit (e.g., 108a) to identify additional delivery protocol parameters. To this end, referring to FIGS. 26 through 28, a physician may use board 266 to select one of listed medicants 300 thereby causing additional medicant information related to the selected medicant to be provided via display 264. The additional information may have been previously received by controller 260 (e.g., during the initial query) or may be obtained via another query to pumps 100a, 100b, etc. In any event exemplary additional information 304 provides instructions regarding how to administer medicant Greenicillin. In this example, the instructions indicate how rate of delivery should be altered based on blood pressure BP and indicate that the prescription was ordered by Dr. Craig.

Figure 28:
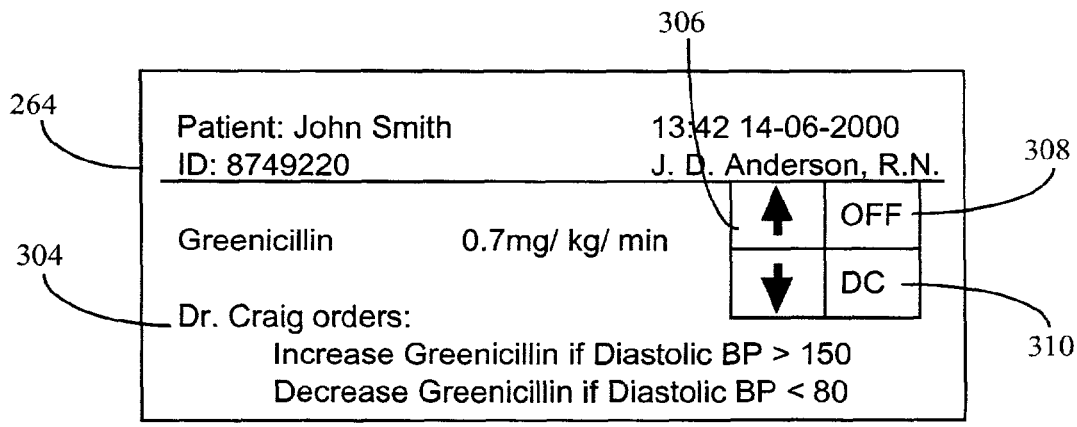
FIG. 28 is similar to FIG. 27, albeit of a second screen shot.

It is further contemplated that controller 260 may be employed to control pump units for modifying medicant delivery. To this end, either board 266 or screen selectable icons may be employed. In FIG. 28 exemplary control icons include screen selectable icons or "soft keys" 306, 308 and 310. Icon 306 include up and down arrows which are separately selectable to increase and decrease delivery of the medicant currently displayed via screen 264, respectively. Icon 308 is an "OFF" icon useable to temporarily turn off a corresponding pump unit to halt medicant delivery. Icon 310 is a "DC" icon where DC stands for discontinue. When icon 310 is selected, the physician is indicating that corresponding medicant delivery should be discontinued. Although not illustrated other keys for altering the duration of medicant delivery are contemplated.

Figure 29:
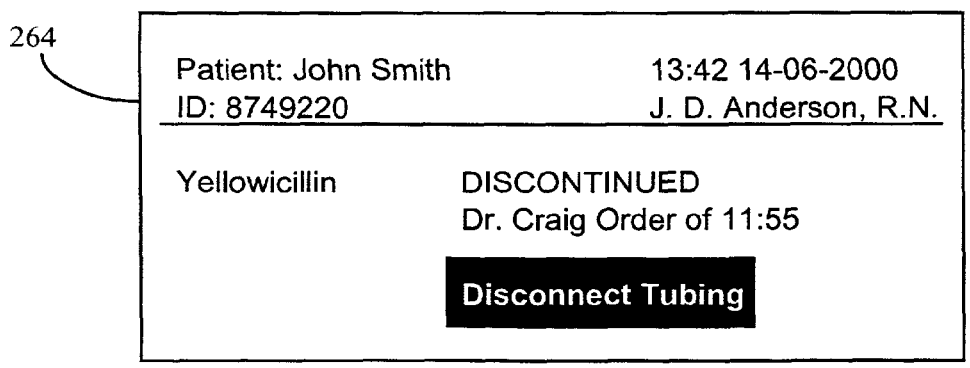
FIG. 29 is similar to FIG. 27, albeit of a third screen shot.

Other control icons and buttons are contemplated for reporting other information. For instance, in addition to providing protocol instructions, a log of pump unit delivery parameter adjustments may also be provided and observed. For instance, referring to FIGS. 26, 27 and 29, using board 266, a physician may select Yellowicillin from the screen shot in FIG. 27 to determine when Yellowicillin was discontinued and who ordered the discontinuance. Upon selecting Yellowicillin, the screen shot in FIG. 29 may be provided indicating that Dr. Craig discontinued Yellowicillin at 11:55. In addition, a command requesting that tubing be disconnected is also provided. Here it is assumed that the pump unit linked to the Yellowicillin bag includes a tube sensing switch 128 (see also FIG. 17) or that system 8 requires a physician to manually indicate that a tube is disconnected.

Figure 37:
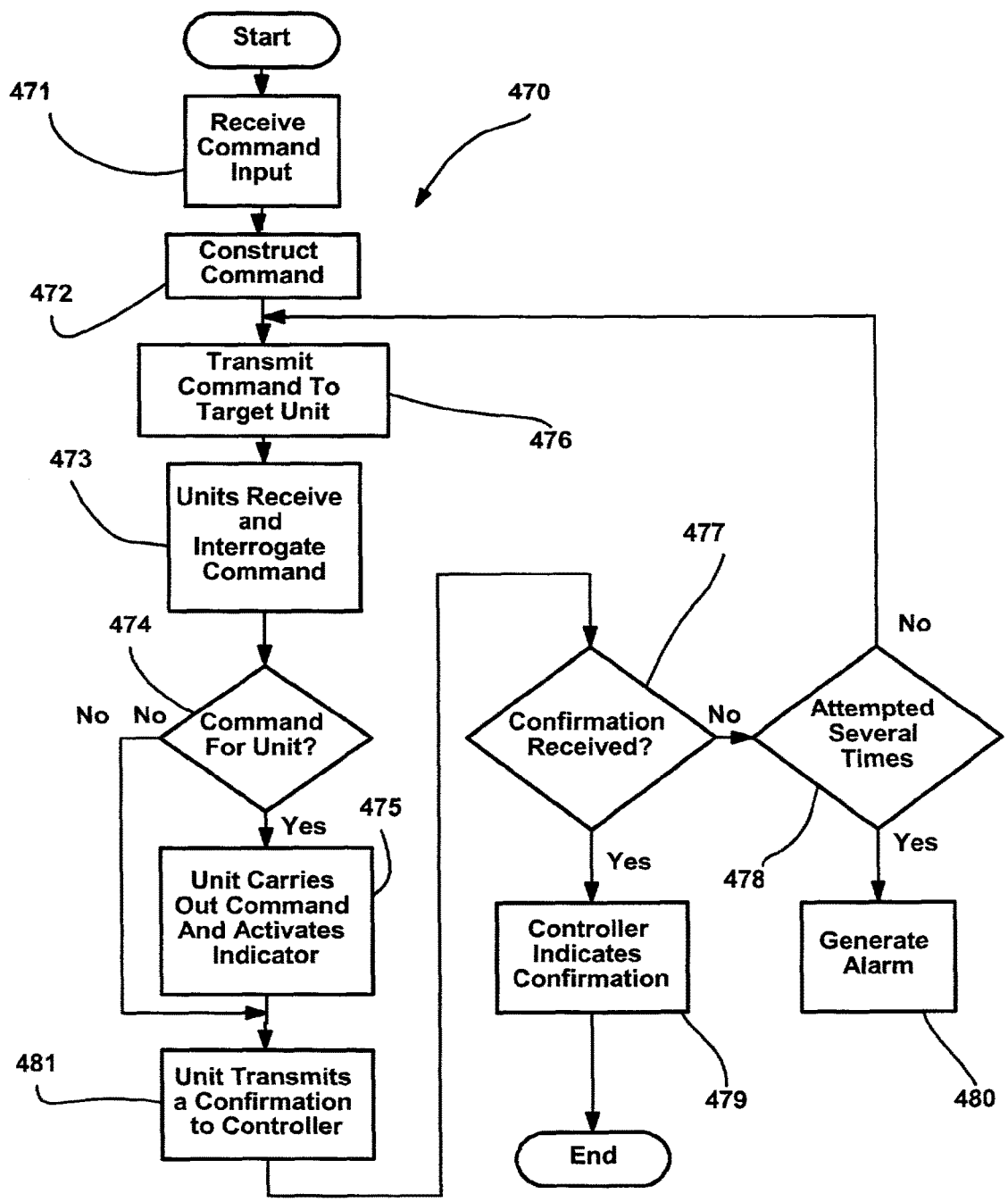
FIGS. 37-43 are additional flow charts according to the present invention.

Referring to FIGS. 26, 26A and 37, an exemplary system control sequence 470 is illustrated. When a control icon is selected at block 471, controller 260 formulates a control transmission at block 472 indicating the control command and the unit (e.g., identification number or system address for a unit 108a) for which the command is intended. Thereafter, the transmission is transmitted at block 476 via transponder 274 to the pumps. Each pump receives the transmission and determines if the transmission is intended for a unit controlled by the pump at blocks 473 and 474. This determination is made by comparing the unit address included in the transmission with the address of each pump unit controlled by the pump. The pump that controls the unit for which the transmission is intended thereafter uses the command information to alter the delivery parameters for the corresponding unit at block 475.

To help guide a physician to perform various manual tasks such as linking and de-linking medicant bags 104 from pump units 108, controller transmissions may include instructions for pumps to indicate a communication or pumps themselves may be programmed to indicate specific information when a controller communication is received as indicated at block 475. For example, referring again to FIG. 29, when a medicant is to be discontinued, to guide a physician to disconnect the IV line 150 linked to the medicant to be discontinued, controller 260 may transmit a message to the pump including the unit currently linked to the line to be disconnected instructing the pump to cause an indicator (e.g., 124, 125, 123, 126, 182, etc.) on the unit to blink, light up, etc., to indicate the time to disconnect. This unit specific indication along with a display message (see again FIG. 29) to "Disconnect Tubing" clearly aids a physician in disconnecting the appropriate line.

Referring still to FIG. 37, in at least one embodiment pumps are programmed to confirm reception of commands. To this end, at lock 481 the pump unit that carries out a command generates and transmits a confirmation message to controller 260. controller 260 monitors for the confirmation signal at block 477. Where no confirmation signal is received, at block 478 controller 260 control skips back to block 476 and transmits the control signal several more times. After transmitting the control signal several times and not receiving a response, controller 260 generates an alarm (e.g., audible or visual) at block 480 indicating a failure to effect the command.

Referring again to block 477, when a confirmation signal is received control passes to block 479 where controller 260 indicates a complete control command via display 264 or some other confirming indicator.

In a similar fashion, controller 260 and associated pumps may guide a physician in other manual processes. For instance, referring to FIGS. 26 and 26A, assume two bags 140a and 140c are linked to patient 12 and that a physician wishes to link third bag 140b to patient 12. In this case transponder 122b on pump 100b may be used to read tag information from tag 200b on bag 140b. A pump processor may determine that bag 140b medicant is intended for patient 12, but may also determine that all pump units (e.g., unit 108d) controlled by pump 100b are already being used. At this point it is contemplated that pump 100b formulates a message to controller 260 indicating that the bag 140b medicant is to be provided to patient 12 but that pump 100b is currently unable to accommodate the other medicant.

Upon receiving the message, controller 260 determines if other system pumps associated with patient 12 have excess capacity (e.g., have a currently unused unit 108). This may be accomplished by either checking a controller database (assuming previously stored information includes a listing of all associated units) or querying associated pumps to identify currently unused units. In any event, assuming controller 260 identifies unit 108b as unused, controller 260, in at least one embodiment, transfers tag information to pump 100a for use in programming unit 108b. In addition, controller 200 causes unit indicator 125b to light up thereby indicating to the physician that bag 140b should be linked to unit 108b. In some embodiments, each unit specific indication (e.g., illumination of an indicator 125) is accompanied by a message via display 264 so that the action expected of the physician is clearly indicated. For instance, where indicator 125b is lit up in the previous example, the message "Connect bag to lit up unit" may be displayed via screen 264.

Referring still to FIGS. 26 and 26A, in yet other embodiments the components described above may be used to facilitate other inventive methods. For instance, controller 260 may be associated with a specific physician so that monitoring and control security functions can be facilitated. Thus, each physician may have his/her own PDA controller 260 or, in the alternative, may be temporarily associated with a controller 260 during a shift. One way of temporarily associating a physician with a controller 260, referring also to FIGS. 3 and 4, is to have each physician check out a controller 260 upon making rounds to visit patients. In this regard, upon checking out a controller, physician information would be transferred from a device 40 to the controller 260 for storage therein. By way of the transferred information various levels of monitoring and control authorization could be supported.

For instance, assume again that a physician wishes to monitor medicants currently being delivered to a patient and also assume that only physicians that work within a specific wing of a medical facility are allowed to monitor patient medicants. In this case, referring again to FIG. 26, after the physician associates controller 260 with patient 12, when the physician requests information from pumps 100 associated with patient 12, the request may include physician identification information. Upon receiving such a request, each pump processor (e.g., 104 in FIG. 17) may compare the physician identifying information with information corresponding to physicians that have monitoring authority. In the present case physicians with monitoring authority include all physicians routinely working within the specific wing of the medical facility.

Where the requesting physician has authority to monitor medicant delivery, receiving pumps provide the requested information so that a display screen shot similar to the screen shot illustrated in FIG. 27 can be generated. However, if the requesting physician does not have monitoring authority, either the pumps 100 would not respond or the pumps would respond by indicating that the physician lacks monitoring authority, a suitable rejection message being displayed via display 264 or via a pump display (e.g., 123b).

In a similar fashion, system 8 may allow a physician to monitor medicant delivery without modifying delivery parameters. For instance, assume only one particular physician working each shift has authority to alter infusion parameters. Also assume that each pump 100a, 100b, etc., stores an indication, along with other information, identifying the physician that has authority to alter delivery parameters. Then, each time any physician attempts to alter delivery parameters for a medicant, the message transmitted by controller 260 would include a physician identification. The receiving pump processors in this case compare the received physician identification with the physician identification that indicates the physician authorized to alter parameters and only changes parameters if the identifications match. Again, when identifications do not match the pumps may send suitable messages back to controller 260 for display to the physician.

In addition to controller 260 querying pumps 100a, 100b, etc. for information regarding corresponding units, it is contemplated that pumps 100a, etc., may automatically provide information related to pump unit conditions and manual pump setting modifications. For instance, referring again to FIG. 26, if a new medicant is to be linked for delivery to unit 108c, upon obtaining medicant information from a bag tag 200 via either transponder 122 or sensor 160 and associating the medicant with unit 108c, pump 100a may transmit a message to controller 260 indicating that a medicant is to be added to the regimen for patient 12. It is contemplated that controller 260 uses the information in the received message to associate controller 260 with pump unit 108c and facilitate functions as described above.

The associating process may include a safety function wherein, when a change in infusion regimen is initiated at a pump unit (e.g., unit 108c), controller 260 requires confirmation that the change is requested by an authorized system user (e.g., a credentialed system operator). To this end, when such information is received by controller 260, controller 260 may provide a prompt requiring the user who initiated the change to identify herself. The prompt may include a blinking message via display 264 instructing the user to perform various authentication steps (e.g., instructions to place the physician's badge (see FIG. 3) proximate an RF field generated by controller 260 so that identifying information can be obtained). In addition, controller 260 may start a timer to time out a period during which authentication must be completed for controller 260 to authorize operation of the unit according to the changed protocol. Where authentication is not successfully completed within the time out period, it is contemplated that controller 260 would not allow the changed protocol to begin, may provide another message via display 266 indicating that the change would not occur and may also log the change attempt in a remote database for future consideration.

Similarly, assuming an entirely new pump is delivered to patient 12's bedside to accommodate delivery of another medicant, when tag information including a target patient ID is obtained from a medicant bag tag by the new pump, the target patient ID information therefrom may be transmitted as part of a query to determine if a central controller 260 has already been associated with patient 12. Upon receiving the transmitted message, controller 260 may then associate with the new pump and establish communications for monitoring and control purposes. Again, here, controller 260 may perform some type of authentication procedure to make sure that the user attempting to add the pump and corresponding medicant to the regimen is authorized to do so.

Figure 38:
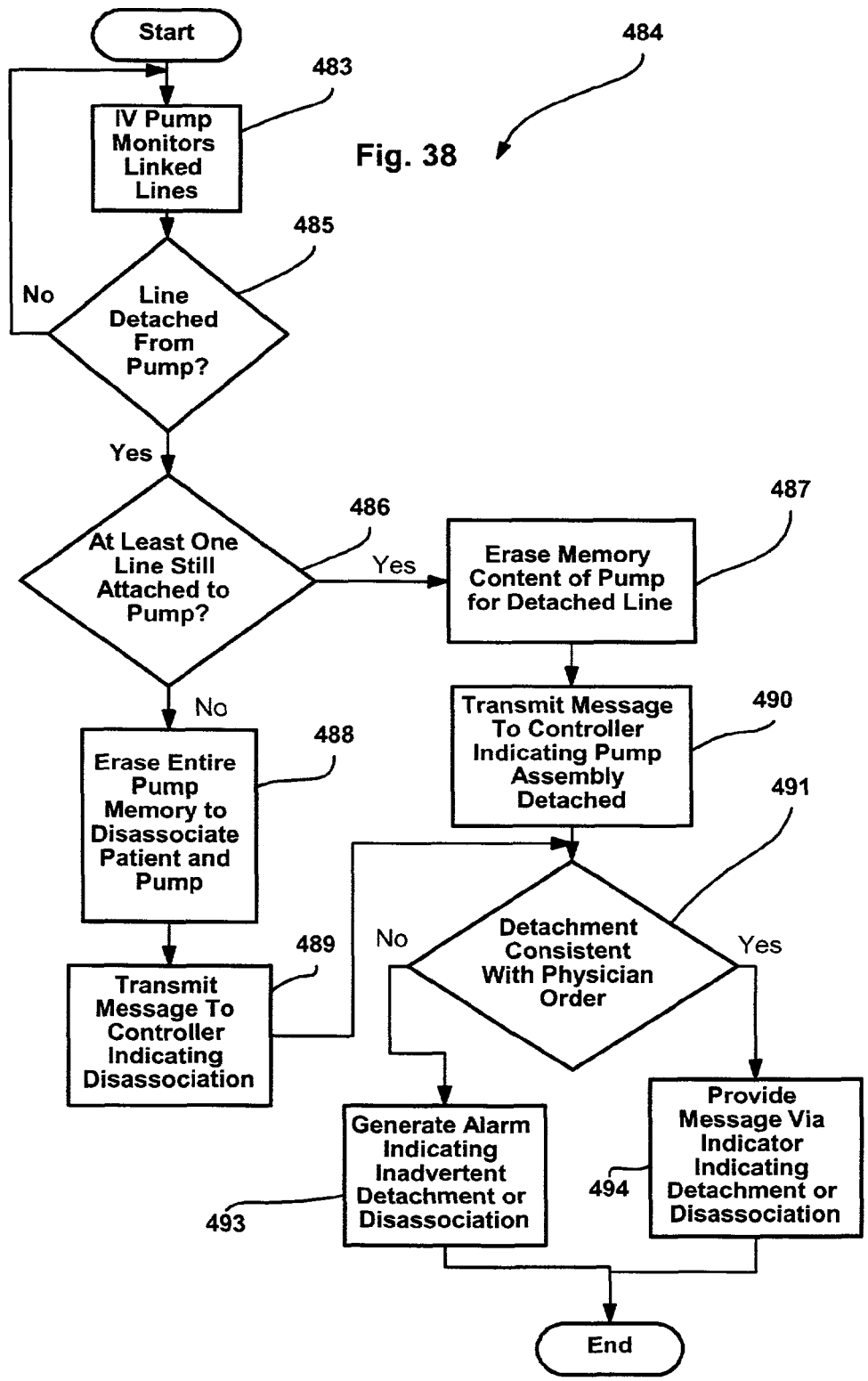

Moreover, referring again to FIGS. 17, 26 and 27, where pump unit 108a includes a line sensing switch 128, when a line is de-linked from the unit 108a, pump 100a may be programmed to transmit a message to controller 260 indicating that the de-linking event has occurred. An exemplary pump monitoring and control process is illustrated in FIG. 38 where, at blocks 483 and 485 an IV pump (e.g., 100a) monitors linked IV lines. At block 485, when any unit IV line is detached, pump 100 control jumps to block 486 where the pump determines if at least one line is still linked to the pump 100. Where no lines are linked it is contemplated that the pump may be programmed to disassociate with the patient so that parameter settings for delivering medicant to the patient are not mistakenly used to deliver medicant to another patient. Thus, where no lines are linked to the pump 100 at block 486, control passes to block 488 where the pump erases its entire memory to disassociate the patient 12 and the pump. Continuing at block 489 pump 100 generates and transmits a message to controller 260 indicating disassociation control then passes to block 401.

Referring again to block 486, where at least one line is still linked to a pump 100 unit but at least one line has been detached, pump 100 erases the memory content from the pump memory that corresponds to the detached line at block 487. This process ensures that the information corresponding to the detached line is not inadvertently used to control delivery of some other medicant to the patient. Next, at block 490 the pump transmits a message to controller 260 indicating which of the lines has been detached. At block 491 controller 260 determines if the sensed line detachment is consistent with any previous orders or change orders that required discontinuance of the medicant that had been being delivered by the detached line. This step may be performed in any of several different ways including accessing a remote server via network 272, comparison to a controller memory, etc. Where the detachment is consistent with a previous order control jumps to block 494 and controller 260 displays a message indicating that the line has been detached and also, perhaps indicating that a portion or all of the memory content of the pump has been erased. At block 491, where the detachment is not consistent with a previous order, controller 260 generates an alarm and may provide a message via display 264 indicating inadvertent disconnection. To reconnect a detached line an association process like those described above would have to again be performed.

Referring still to FIGS. 26 and 26A, controller 260 may be programmed to require specific timing between information transfer events to ensure that stale and therefore potentially inaccurate information is not used to program medicant delivery parameters. To this end processor 620 may include a timer 650 that generates a time stamp, referred to generally hereinafter as a time, for each of several time significant events with processor 620 comparing event times to identify periods between events and affect control as a function thereof. This timing and control feature is provided to avoid various potentially harmful medicating scenarios.

For instance, assume that prior to delivering medicant to a first patient 12, patient 12's device 10 is used to associate controller 260 with patient 12. Also assume that prior to linking pump units to patient 12, patient 12 is removed from the room for some other medical procedure. Moreover, assume that another patient is placed in patient 12's initial location and medicant earmarked for patient 12 is delivered to the bedside of the other patient. In this case, when controller 260 attempts to determine if the medicant is meant for the other patient, controller 260 erroneously determines that the medicant should be delivered to the patient proximate to the medicant (i.e., the other patient). Controller 260 then authorizes delivery of the medicant to the other patient thereby causing a mismedication to occur.

As another instance, a medicant A may be prescribed for a patient and associated with the patient at a first time but not delivered (i.e., infused) to the patient at the first time. Thereafter, prior to a second time a physician may decide not to deliver medicant A to the patient. Nevertheless, because of the previous association at the first time the medicant may be delivered at the second time despite the decision to forego delivery. Other similarly potentially catastrophic or at least troublesome scenarios abound and likely will occur routinely as people come to rely more heavily on automated systems to reduce human errors.

Figure 39:
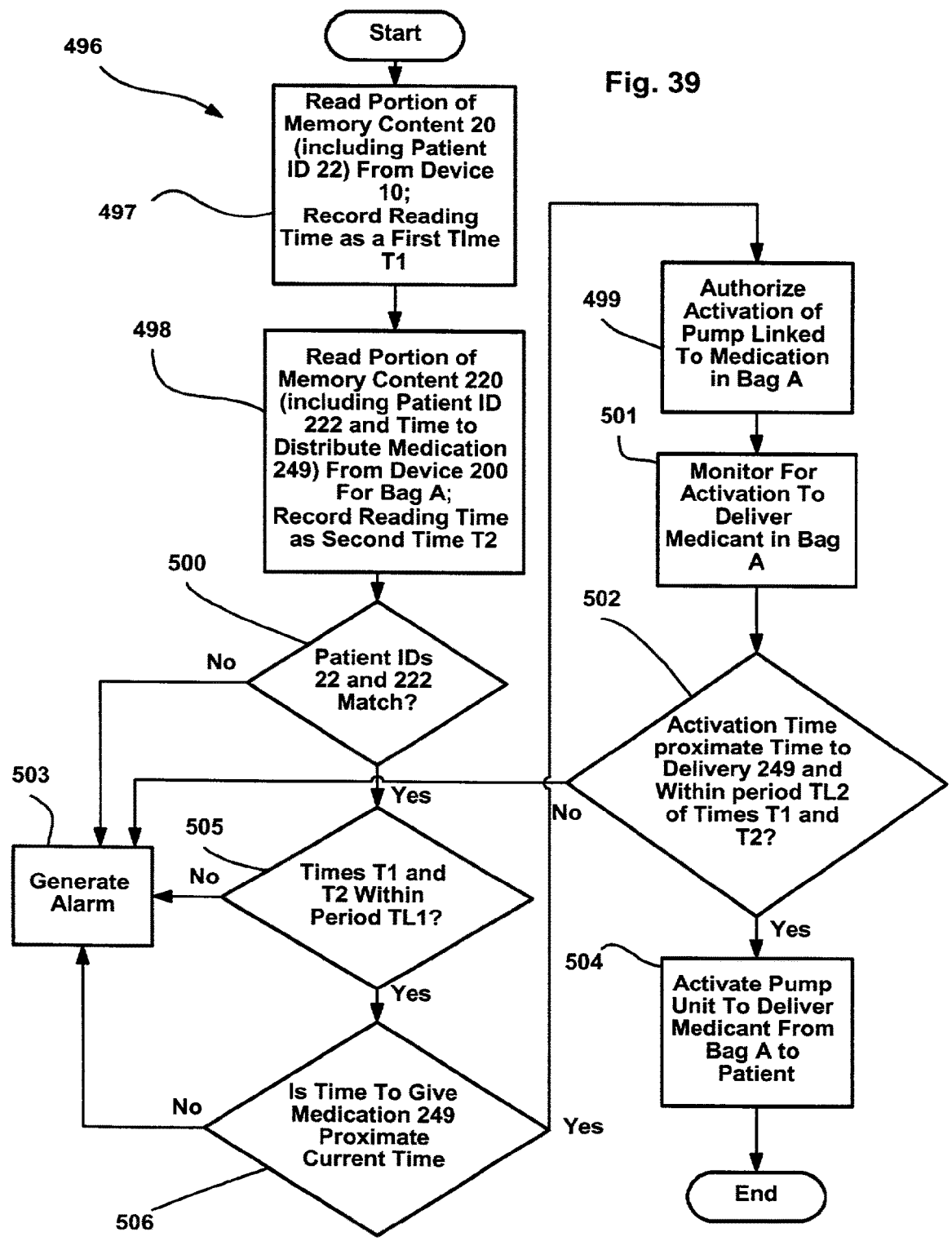

To minimize the likelihood of errors of the previously described type, controller 260, in at least one embodiment, is programmed to require that prior to facilitating delivery of a medicant to a patient 12, both patient 12 presence and medicant information be confirmed within a short time period of each other. In addition, controller 260 may be programmed to confirm that a delivery time and a prescribed time are proximate and that the delivery time and the times at which the patient and medicant information are obtained are proximate (i.e., within a threshold period). Referring to FIG. 39, an exemplary timing method 496 is illustrated. Referring also to FIGS. 26 and 26A, at block 497, controller 260 is used to obtain information including a patient ID 22 from a patient mounted identification device 10 on patient 12. When the information is obtained, controller 260 identifies the time and stores the time as a first time T1.

Next, at block 498, controller 260 is used to obtain information including both patient ID 222 (i.e., indicating the patient for whom the medicant has been provided) and the time to distribute the medicant 249 (see also FIG. 6) from a bag tag (e.g., 200a). Also, at block 498, controller 260 identifies the time at which the medicant information is obtained from the tag 200a and records that time as a second time T2.

At block 500, controller 260 compares the patient IDs 22 and 222 to determine if the IDs are identical. Where the IDs are different, control passes to block 503 and controller 260 generates an alarm indicating that the IDs are different and that the medicant should not be delivered to patient 12. Where the IDs 22 and 222 are identical control passes to block 505 and the timing method begins.

At block 505, controller 260 compares times T1 and T2 (i.e., the times at which IDs 22 and 222 were obtained from devices 10 and 200a, respectively) and where the times are separated by more than a first threshold period TL1, control passes again to block 503 where an alarm is generated. Time TL1 is a period that corresponds to a likely safe duration between collection of IDs 21 and 222. For instance, an exemplary safe period TL1 may be 3 minutes. The alarm at block 503 in this case may indicate that period TL1 has been exceeded and may request that the physician reobtain the packet IDs 22 and 222 from devices 10 and 200a, respectively.

Continuing, at block 503, when the time between collecting IDs 22 and 222 is within period TL1, control passes to block 506 where controller 506 determines if the time to give medication 249 is proximate the current time. Where the time to give medication 249 is not proximate (e.g., 20 minute difference) the current time, control passes to block 503 and controller 260 generates another alarm indicating the time to deliver 249 and requesting that the physician either override the time to deliver 249 or recollect the patient IDs 22 and 222 at a time closer to the time to deliver 249. Where the time to deliver 249 is proximate the current time control passes to block 499 where controller 499 authorizes activation of the pump unit (e.g., 108a) linked to the medicant in bag A.

At block 501, controller 260 monitors for activation of the pump unit linked to bag A. Here it is assumed that even after authorization at block 499, pump 100a requires a physician to activate pump 100a to begin delivery. For example, activation may entail selecting an icon on controller screen 264 or a button on board 266. Upon activation at block 502, controller 260 compares the activation time to delivery time 249 and times T1 (i.e., the time at which ID 21 was obtained from device 10) and T2 (i.e., the time at which ID 222 was obtained from device 10). Where the activation time is more than a second threshold period TL2 away from any of the times 249, T1 or T2, control passes again to block 503 where controller 260 generates a warning that the above sequence should be repeated. Where the activation time is within period TL2 of times 249, T1 and T2, controller 260 activates the pump unit 108a to deliver bag A medicant to patient 12 at block 504.

Other ways, in addition to timing, are contemplated to make sure that confirmation data corresponding to a procedure is collected in a temporally proximate fashion and therefore to reduce the likelihood of mismedication. To this end, where controller 260 is used to collect data from various devices to initiate an infusion process, controller 260 may require that all or a subset of data corresponding to the process be collected during a single button activation cycle. For instance, where selection of button 266 (see FIG. 26) causes controller 26 to commence an authentication process, data collection from a patient wrist device 10 and a tag 200 on a bag may have to be performed while button 266 remains activated. Generally, the period over which a physician will be able to comfortably activate a button 266 (i.e., continually press a button 266) will only be a few seconds (e.g., 30-60 seconds) and therefore temporal proximity of data collection from relevant devices will be likely. In these cases, processor 260 may provide a sequence of instructions to a physician regarding collection sequence and, in the event that all expected data is not collected during a single button activation cycle, controller 260 may provide an alarm indication, (e.g., perhaps data collection instructions along with an audible tone).

Any of the data collection limitations described herein with respect to the controller 260 are also applicable to other data collecting devices such as a physician's badge. To this end, referring again to FIG. 3, a badge 40 may be programmed to enforce data collection timing rules where data must be collected within a specific period or to enforce rules requiring data to be collected during a single button action period or any other similar rule type.

While unlikely, it is possible that IV lines could be de-linked from one patient recipient and linked to another during medicant delivery. To avoid this problem, controller 260, in one embodiment, is programmed to obtain a confirming signal from device 10 periodically (e.g., every minute or two). The confirmation signal may be obtainable via either a query and a response or simply by monitoring for a "heart beat" signal that is periodically (e.g., every minute) generated by device 10.

While not illustrated, controller 260 may also be in communication with a patient monitor or may be incorporated in a patient monitor so that current vital signs can be displayed and used to alter infusion delivery parameters. To reduce distracting information, controller 260 may be programmed to provide only vital signs related a physician's standing orders (e.g., blood pressure but not heart rate). Similarly, lab results may be obtained via network 272 and presented were appropriate.

Referring to FIGS. 26 and 26A, when a physician's order requires a large volume of medicant to be delivered to a patient often two or more medicant bags have to be used in series to deliver the volume. Thus, a first bag may be used to deliver a first half of a prescribed volume and a second bag may be subsequently be used to deliver a second half of the prescribed volume. In this case, it is contemplated that tags 200 on each of the first and second bags would include similar medicant delivery information, at least with respect to medicant type and/or parameter settings (e.g., rate of delivery, etc.) and/or medication order numbers.

During medicant delivery, attending physicians often alter delivery parameters as a function of how a patient is responding to a medicant. Thus, it is often the case that when a first bag in a multibag delivery is depleted and a second bag is to be linked to the patient for delivery, the most recent parameter settings corresponding to the first bag will be different than the settings prescribed on the tag 200 on the second bag. It is also often the case that, based on how the patient responded to the medicant in the first bag, the best delivery parameters for the patient remain the parameter settings most recently set for the depleted first bag.

Figure 40:
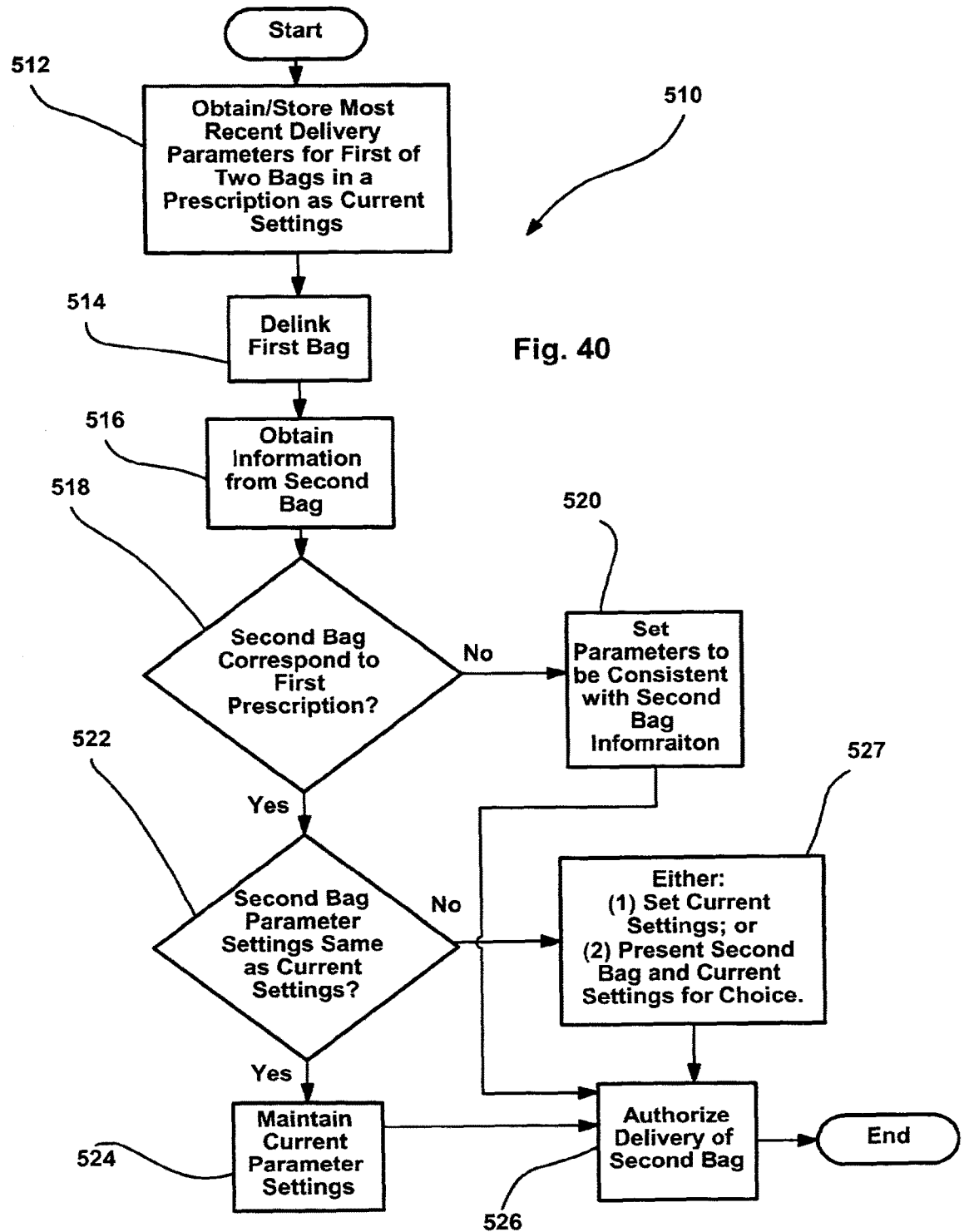

An exemplary method 510 for dealing with delivery of multibag volumes is illustrated in FIG. 40. Referring to FIGS. 26, 26A and 40, at block 512 controller 260 obtains and stores the most recent parameter settings for a first of two bags that together compromise a prescription as "current settings." For instance, if a delivery rate on a first bag tag prescribed 10 ml./hr. and during delivery, the rate was cut back to 0.05 ml./hr., the most recent or current setting would be 0.05 ml/hr. At block 514 the first bag is delinked from the pump and the second of the two bags is presented for infusion. At block 516 controller 260 obtains the information from the second bag tag including delivery rate. At block 518 controller 260 uses the information received from the second bag to determine if the second bag corresponds to the same prescription as the detached first bag. Where the second bag is associated with a different prescription than the first bag control passes to block 520 where controller 260 sets the delivery parameters to be consistent with the second bag information. Then, at block 526 controller 260 authorizes delivery. Delivery authorization may entail writing the settings to a corresponding pump unit or simply sending an authorization signal.

If the second bag is associated with the same prescription as the first bag, control passes to block 522 where controller 260 compares the second bag information (e.g., rate of delivery) to the current settings. In this case, because the initial delivery rate for the first bag was 0.10 ml/hr. and the two bags are part of one prescription, it is likely the second bag rate also is 0.10 ml/hr. Thus, in the present case, at block 522 control passes to block 527 where controller 260 either (1) sets the current settings (i.e., the last recent settings for the first bag) or (2) provides the second bag and current settings via screen 264 for selection. After the current settings are affirmed or after the selected settings are affirmed at block 527 control passes to block 526 where delivery of the second bag medicant is authorized.

Referring again to block 522, where the second bag parameter settings are the same as the current settings control passes to block 524 where the current settings are maintained and then to block 526 where controller 260 authorizes delivery of the second bag medicant.

Referring to FIGS. 6, 26 and 26A, where controller 260 is linked to pumps 100a, 100b, etc., via a hardwire cable or the like 255 and is also linked via network 272 to a server that archives all standing infusion orders, it is contemplated that patient identification information 222 may not be included in bag tag memory content 220. Instead, upon associating with a patient 12 via device 10 or in some other manner, controller 260 may obtain medicant delivery information from each of linked pump units 108a, 108b, etc. and send the patient ID information from device 10 and the delivery information to the server for comparison to standing infusion orders. Upon receiving the information from controller 260, the server can then either confirm delivery of the medicants or, in the event that the delivery information is inconsistent with standing orders, may activate one or more indicators on controller 260, pumps 100a, 100b or pump units to alert the physician of the error.

Figure 41:
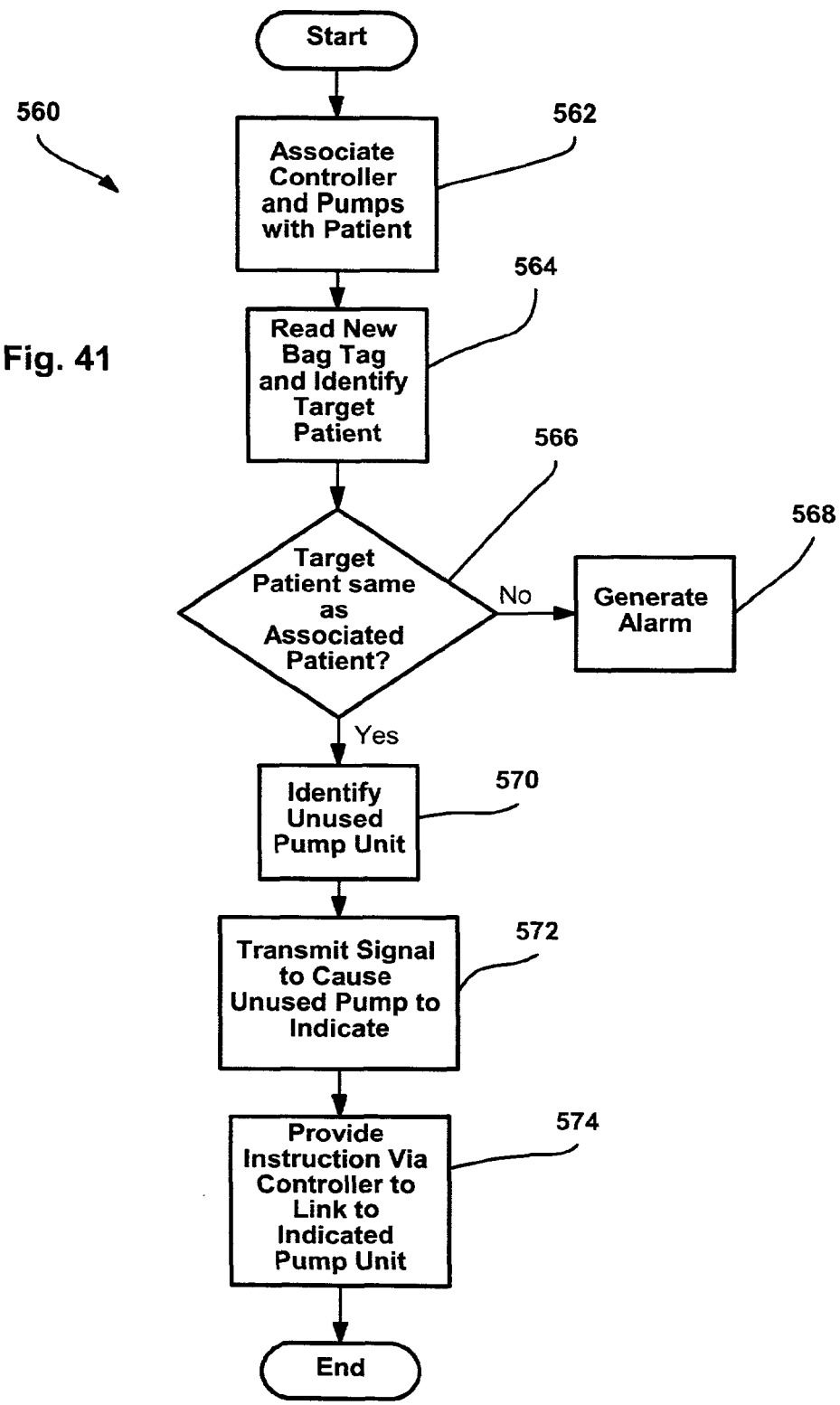

Referring again to FIG. 26, where tags 200a, 200b, etc. are suitably configured, controller transponder 274 may be used to obtain information directly from tags 200a, 200b, when new bags are to be linked to patient 12. In this case, controller 260 may also be able to identify an available unit for use with a new bag. An exemplary method for identifying an unused unit is illustrated in FIG. 41. At block 562, pumps 100a and 100b and controller 260 are associated with patient 12. Assume that unit 108c is currently unused and that a new bag is provided for delivery to patient 12. When the new bag is delivered to patient 12's room, controller 260 is used to obtain information from the new bag tag (e.g., 200) at block 564. At block 566 controller 260 determines if the target patient (i.e., the patient specified for delivery by the read tag) is the same as the patient associated with the controller 260. If the target and associated patients are different control passes to block 568 where controller 260 generates an alarm. Where the target and associated patients are identical control passes to block 570.

At block 570 controller 260 identifies units (i.e., at least one unit) including unit 108c, that are not currently being used. Next, at block 572 controller 260 transmits a signal to the pumps to cause at least one of the unused units (e.g., 108c) to indicate availability (e.g., unit 108c activates an LED 125 or the like). In addition, at block 574 controller 260 may provide instructions to the physician to link the bag to the indicated unit for delivery. Thereafter the physician links the bag.

In some embodiments controller 260, while moveable, may not be easily positioned proximate other system devices to facilitate proximal communication. For instance, in some embodiments controller 260 is in the form of a PC positioned on a cart that can be transported to a patient's room. In other embodiments pumps 100a, 100b may not include sensors 122a, 122b, etc., for reading tag 200 information and may not store extensive obtainable medicant delivery information. In this case physician's badge 40 may be used to collect information from other system devices for use by controller 260. For example, referring again to FIGS. 3, 4, 2, 26 and 26A, to associate patient 12 and pumps 100a and 100b with controller 260, a physician may use device 40 to obtain patient ID information from device 10 and also to obtain medicant information from each of pumps 100a and 100b where the medicant information includes patient ID information indicating the patient for whom medicants linked to pump units (e.g., 108a, etc.) has been dispensed. In addition, device 40 would also obtain pump address or ID information from each of several pumps. After collecting the aforesaid information it is contemplated that the physician places device 40 proximate transponder 274 and transfers the information to controller 260. Thereafter, controller 260 uses the received information to associate with patient 12 and pumps 100a and 100b and establish control and/or monitoring.

In other embodiments pumps 100a and 100b, etc., may not be capable of reading tag 200 information (i.e., may lack sensors 122a, 160, etc). Nevertheless, it would be desirable, even in these cases, to be able to determine if patient information on bag tags matches a patient 12 to which the medicant in the bag is to be delivered. To this end, a four step process or method referred to as the "A, B, C, D" method is contemplated by the present invention. "A" is the step of collecting patient information using a physician mounted device 40 (see also FIG. 3), "B" is the step of collecting IV bag information using a device 40, "C" is the step of collecting pump identification information via device 40, and "D" is the step of transferring the collected information to controller 260 along with, in at least some embodiments, the identity of the physician. By repeating these steps (the order of "A", "B", and "C" can be intermixed) a physician has a repeatable process that can be executed to collect data necessary to ensure that patients receive correct medicants in the correct doses and at the correct times.

Figure 42:
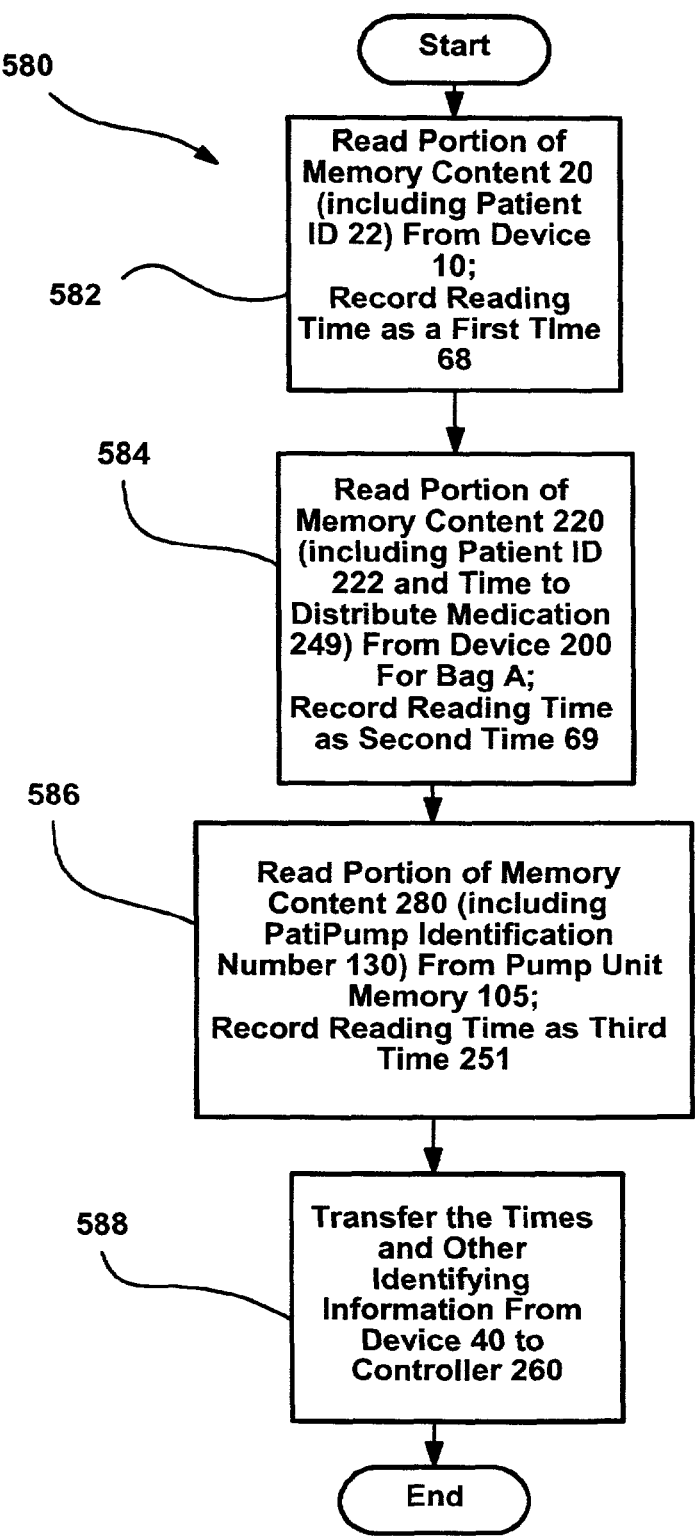

Referring to FIG. 42, a flow chart 580 consistent with the ABCD method is illustrated. At process block 582 physician identification device 40 is used to read at least a portion of memory contents 20 from a patient identification device 10 (Step A) and stores the information including patient ID 22. In addition, optionally, device 40 also determines the time at which the ID 22 is obtained from device 10 and store that time as first time 68 (see also FIG. 4).

Next, at block 584 device 40 is used to collect (Step B) tag information including target patient ID 222 and time 249 to distribute the medicant in a bag 200, determines the time 69 of obtaining this information and then stores this information. At block 586 device 40 is used to collect (step C) pump information including a pump identification number 130 and perhaps currently set operating parameters from memory 105 and, optionally, identifies the time 251 at which the pump identification number is received and stores that information in contents 60 (see FIG. 4).

After completing each of steps A, B and C, the physician then positions badge device 40 proximate controller 260 and transfers (step D) the collected data thereto after which controller may perform any of the several different functions described above.

It should be appreciated that where controller 260 is hardwired to other system devices via an intranet or some other similar network, device 40 may be used to remotely facilitate monitoring and/or control of medicant delivery to a patient. For instance, referring still to FIG. 26, assume controller 260 is located at a nurses station and that a physician wants to monitor medicant delivery to a particular patient 12 at the nurses station via controller 260 after the physician has completed his rounds. Upon visiting patient 12, the physician may collect information from each of device 10 and pumps 100a and 100b for associating purposes. Upon returning to the nurses station the physician can cause the collected information to be transferred to controller 260 thereby causing controller 260 to establish communication with hardwired pumps 100a and 100b via their network addresses. Versions of this feature are also contemplated in a wireless environment.

Referring yet again to FIGS. 26 and 26A, where controller 260 is linked or linkable to a network 272, in addition to facilitating remote monitoring, controller 260 may also facilitate remote control of units 108a, 108b, etc. For instance, a physician at a remote station may be able to link to controller 260 to obtain all of the information described above. In this case, whenever a remote controller is used to monitor/control, any changes to parameter settings may be conveyed to the remote controller via network 272. In addition, remotely modified parameter settings may cause any of the associated pump and unit indicators (e.g., 125a) to indicate a modification.

E. Verifying Medication Order

Sometimes, between the time a medicant is dispensed by a pharmacist for delivery to a patient and the time the medicant is actually delivered, a physician may cancel or modify the corresponding prescription. This is particularly true in cases where the time between dispensation and delivery is a relatively long period for some reason. In these cases, to avoid delivery of medicant pursuant to a stale order, the present invention contemplates a method and system for verifying that information on a bag tag (e.g., 200a) used to program a pump unit is current.

Figure 31:
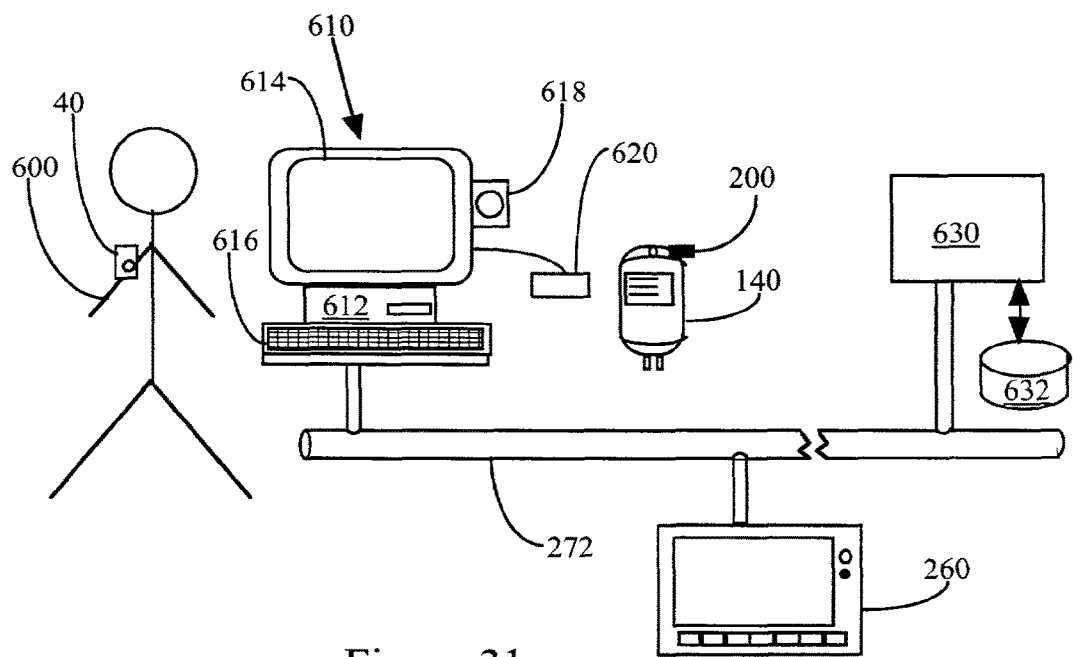
FIG. 31 is a schematic view of an order verification system according to the present invention.

To this end, referring to FIG. 31, an exemplary system includes a physician ID badge 40 worn by a physician 600, a conventional computer terminal 610, a medicant bag 200 with a tag 140, a remote server 630, a database 632 and a controller 260. Many of the components in FIG. 31 are similar in construction to those described above and therefore will not be described again here in detail.

Computer terminal 610, controller 260 and server 630, as illustrated, are all linked via network 272. Computer terminal 610 includes, among other things, a screen 614, a processor 612, a data entry device 616 (e.g., keyboard, mouse, etc.), and communication devices 618 and 620. Device 618 is used to communicate with physician identification device 40 and device 620 is used to communicate with tag 200. In some embodiments devices 618 and 620 may comprise a single device (e.g., a transponder of some type). In FIG. 31 is it assumed that current prescriptions for facility patients are stored on database 632 and are accessible by server 630.

Figure 43:
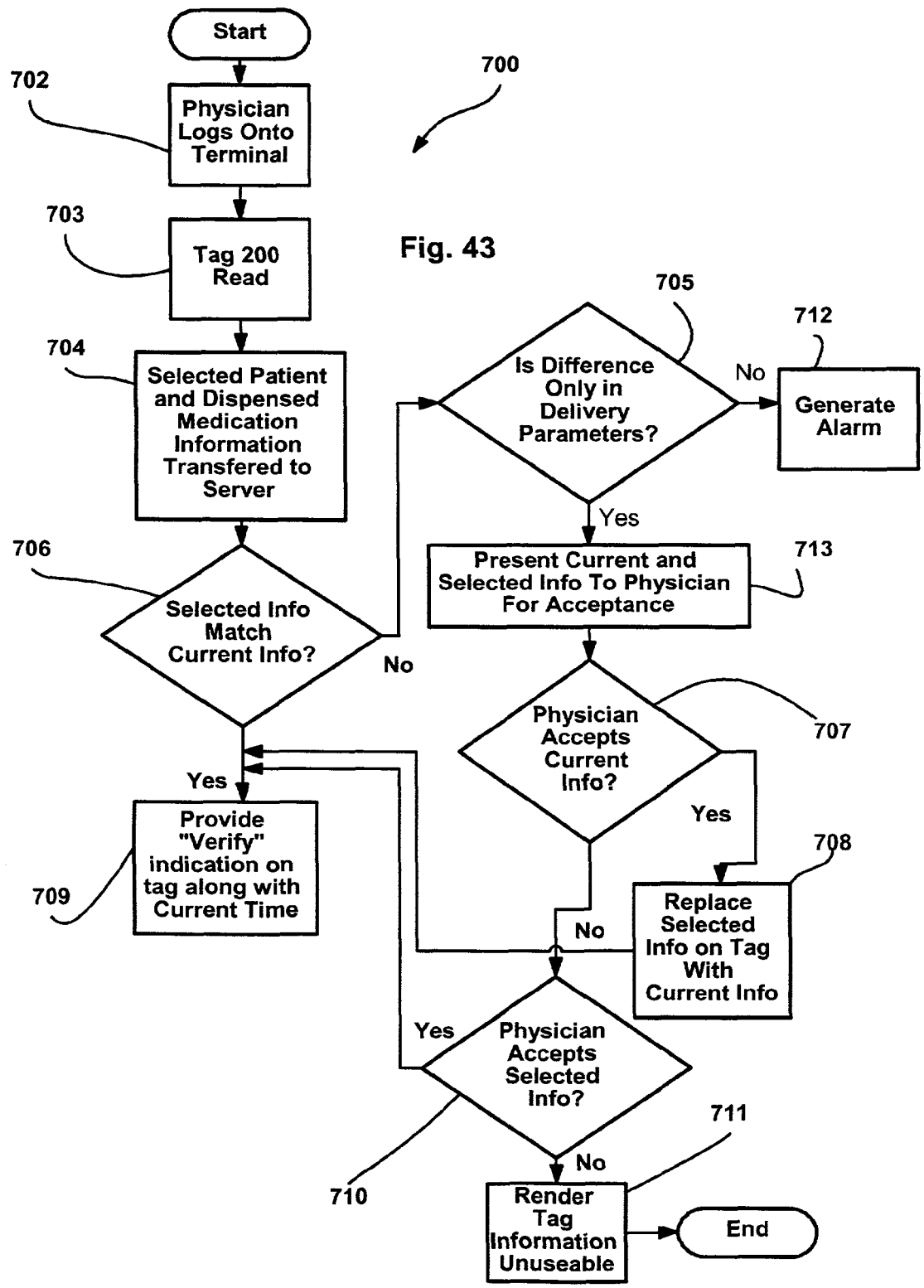

Referring also to FIG. 43, an exemplary verification method 700 is illustrated. At block 702 a physician 600 logs onto the hospital network via terminal 610 by entering a password or by activating physician identification device 40 to transmit a wireless password (encrypted or not) to device 618. At block 703 tag 200 is read by terminal 610 via communication device 620. Referring also to FIG. 6, patient information 222 and dispensed medication delivery information 230 is transferred to server 630 at block 704. Server 630 compares a current prescription list for the target patient to the dispensed delivery information to determine if the medication in the IV bag is to be given to the target patient at block 706.

If the medication is to be given to the target patient, terminal 610 sets an order verified flag 248 in tag 200 along with the current time at block 709. Where tag 200 does not include an electronic memory but instead includes printed indicia, a printer (not illustrated) may be provided to record the order verified flag and time on a label that is attached to IV bag 140.

Referring still to FIG. 43, at block 706, where the dispensed delivery information (i.e., the information read from bag 140) is not identical to at least one current prescription for the target patient, control passes to block 705 where server 630 determines if the difference between the dispensed delivery information and at least one of the currently prescribed medicants is only with respect to delivery parameters. For example, a tag may indicate Yellowicillin@0.10 ml/hr. and one of the current prescriptions for the target patient may be Yellowicillin@0.15 ml/hr. Where there is not at least a medicant match, control shifts to block 712 where server 630 generates an alarm (e.g., visual indication on screen 614) indicating the mismatch. In addition, it is contemplated that, at least in some embodiments, a prescription archive to identify if a prescription corresponding to the dispensed delivery information from tag 200 has been recently canceled and can then indicate cancellation information including physician ID, date, time, etc., via display 614.

Where the only difference between the dispensed delivery information and at least one prescription for the target patient is in parameters (i.e., there is a medicant match), at block 713 server 630 provides the dispensed delivery information and the similar prescription information via screen 614 for the physician to select. At block 707, where the physician accepts the prescription information, terminal 610 replaces the dispensed delivery information on the tag with the prescription information. Next control passes to block where a verify flag or indication is set on the tag 200 along with the current time.

Referring again to block 707 and also to block 710, where the physician does not accept the prescription information but does accept the dispensed delivery information, control passes to block 709 where, again, a verify flag indication is set on tag 200 along with the current time.

Referring yet again to block 710, if the physician elects not to accept either the current or selected information, control passes to block 711 where terminal 614 renders the tag information useless. In the case of an electronic tag, this rendering may include erasing the tag 200 memory. In the case of a printed tag, this rendering may include printing a "VOID" label to be placed over the tag indicia and instructing the physician to place the label over the indicia via display 614.

Although not illustrated in FIG. 43, a physician may decide that a medicant in bag 200 is to be given to the patient but that the physician wants to prescribe delivery parameters that are different than either of the dispensed delivery information or similar prescription parameters. Here it is contemplated that, after block 710, in at least one embodiment, the physician is able to use terminal 610 to modify delivery parameters, cause the modification to be made on tag 200 and also set a verify flag identifying the verify time on tag 200.

Figure 48:
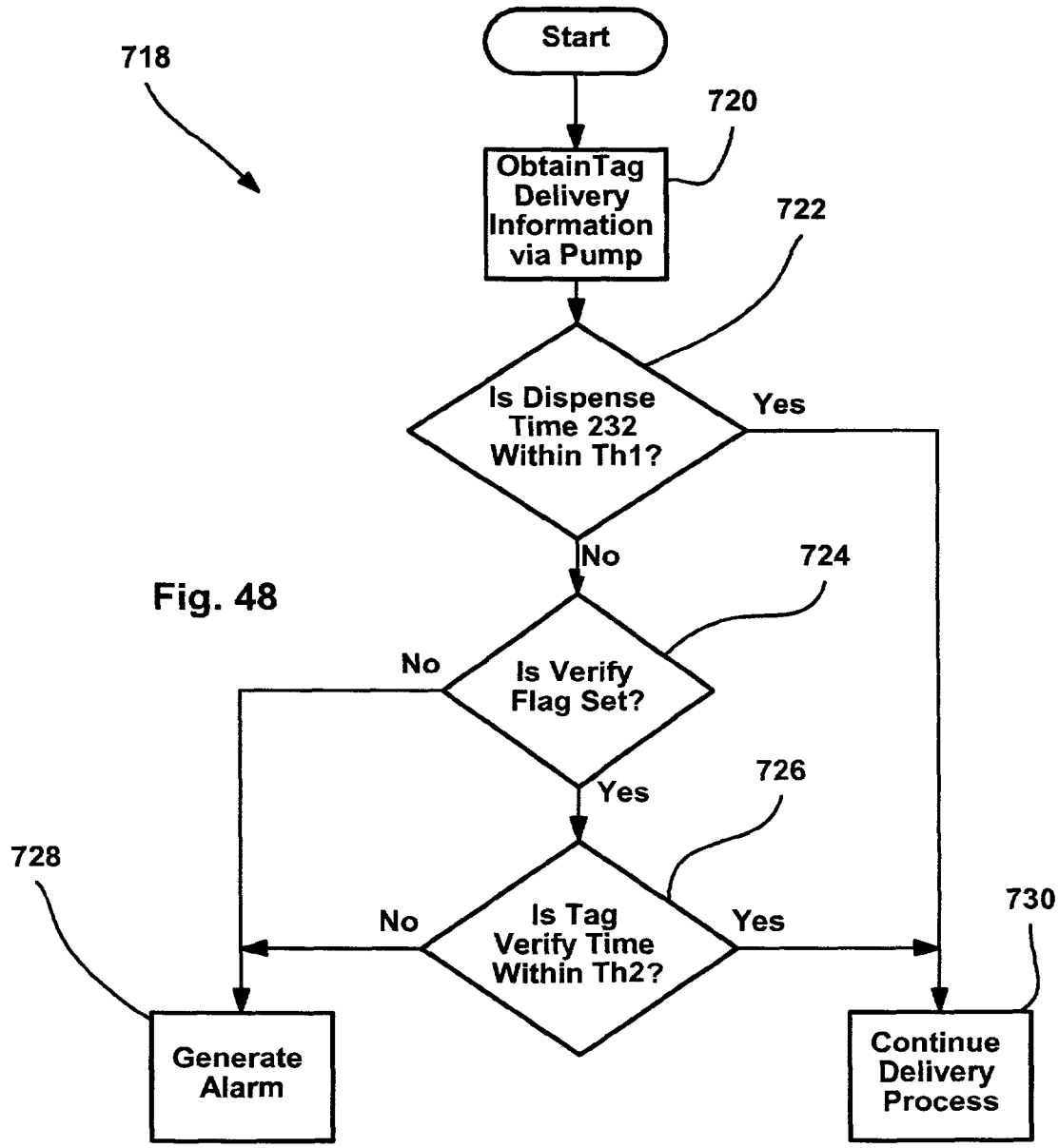
FIG. 48 is yet one more flow chart consistent with the present invention.

Referring now to FIG. 48 an exemplary method 718 for employing verification flags to avoid stale delivery parameters is illustrated. Referring also to FIGS. 26 and 26A, at block 720 a bag 200a arrives at patient 12's room for delivery and, prior thereto, a physician causes pump 100a to obtain the dispensed delivery information from tag 200a including the verification flag and corresponding time 248 and the time 232 at which the medicant in bag 200a was dispensed.

At block 722 pump processor 104 determines if the dispensed time is within a threshold time period Th1 (e.g., 30 minutes) of the current time. Where the dispensed time 232 is within the preceding period Th1, control passes to block 730 where pump 100a continues the delivery process as described above. Where the dispensed time 232 is prior to the preceding Th1, control passes to block 724 where processor 104 determines if the verify flag has been set. Where the verify flag has not been set control passes to block 728 where pump 100a generates an alarm and may indicate that the physician should take steps (e.g., perform process 700 in FIG. 43) to verify that the tag information is still accurate.

Where the verify flag has been set at block 724, control passes to block 726 where processor 104 determines if the tag verify time is within threshold period Th2 of the current time. Again, where the tag verify time precedes Th2 of the current time control passes to block 728 where processor 104 generates an alarm requesting verification. Where the tag verify time is within Th2 of the current time control passes to block 730 and the delivery process continues.

According to another version of the verification process described above with respect to FIGS. 43 and 48, instead of setting both a verification flag and a separate time indication on a tag, the flag may take the form of a verification time to be used subsequently. In addition, it should be appreciated that where period Th1 is set to a small period the system can be used to ensure that a verification process be performed every time an infusion process is to be initiated.

While the verification processes (see FIGS. 48 and 43) are described above as being performed by server 630 and pump and pump 100a, the processes may be performed in whole or in part by either a physician's identification device 40 or controller 260. With respect to embodiments where physician's device 40 performs verification, dispensed delivery information may be obtained by device 40 from tag 200 and tag 40 may communicate with database 632 to determine if tag information is accurate. Where accurate information is confirmed, device 40 may then subsequently be used to authorize medicant delivery via a transmission to pump 100a.

In the alternative, referring still to FIG. 31, server 630 may verify tag information but may then set a verify flag on physician device 40 which is subsequently used at delivery time by device 40 to perform a verification process akin to the process in FIG. 48.

Referring yet again to FIG. 31, where controller 260 performs the verification processes, the processes are very similar to these illustrated in FIGS. 48 and 43 except that the physician logs onto controller 260 at step 702 instead on terminal 614 and controller 260 needn't obtain tag delivery information a second time at block 720 because controller 260 already presumably has that information stored. In addition, in this case, controller 260 may set an internal verification flag for a particular bag and therefore would not have to set the verify flag or alter other information on the tag 200.

Moreover, where controller 260 performs verification, independent of any other verification processes performed by either controller 260 or other system devices prior to the time of delivery, controller 260 may perform a final verification process by transmitting delivery parameters for corresponding medicants to be delivered to a server 630 causing the server to either authorize delivery or generate an alarm as a function of comparing the delivery parameters to current prescriptions for the patient. In this manner any change to a standing order, even if the change occurred a few seconds prior to an attempt to deliver a medicant, would be identified and considered by the physician.

F. Wireless Communication and Limitations on Controller 260 Functionality

While some limitations and features have been described above that help to ensure that controller 260 and other system devices are communicating with other intended devices (e.g., LED activation, minimal wireless communication power so that communications are only between proximate devices, etc.) and ensure that delivery changes are affected for the appropriate patient, additional limitations and features are contemplated. For instance in some cases where controller 260 is portable, e.g. on a push cart, carried, or on a trolley, and where controller 260 is able to receive and review information on several patients, a split communication channel 255 protocol may be used. For example when controller 260 is only receiving and displaying information from an IV pump 140 attached to a patient, channel 255 may be adjusted to use a relatively high power or may be networked via a 802.11, Bluetooth or other network. However, for controller 260 to be able to adjust the flow rate 292, duration 293, dose 294, etc. communication channel 255 may be set to operate at a low power setting only or may operate on a different local channel, e.g. infrared (IR) or acoustic transmissions) thereby ensuring that controller 260 is only in communication with proximal IV pumps 100.

Another limitation that can be placed on controller 260 is that prior to changing any pump delivery parameter, a portion of memory contents 20 from patient identification device 10 (see FIGS. 1 and 2) be obtained via transponder 122. Alternately, a portion of memory contents 20 may be obtained or required to be obtained episodically, (e.g. every 2 hours since the last time controller 260 was in communication with an IV pump).

Similarly, prior to using a portable controller 260 or a conventional PDA (e.g., 40) to read a portion of memory contents 280 from a pump 100, it may be required that the device (i.e., 260, 40) be used to obtain a portion of contents 20 from a patient device 10 so that the contents can be compared to similar information stored in pump to ensure that the pump information displayed corresponds to the specific patient to read a portion of memory contents 20.

G. Alternate Pump Configuration

Referring now to FIG. 26, it should be appreciated that controller 260 may be used to control virtually all aspects of pump operation and to monitor virtually all aspects of pump operation. For this reason, pumps 100*a*, 100*b*, etc. do not necessarily require their own screens (e.g., 123*a*) or complex keypads (e.g., 106*a*) for data input and parameter adjustment.

Figure 32:
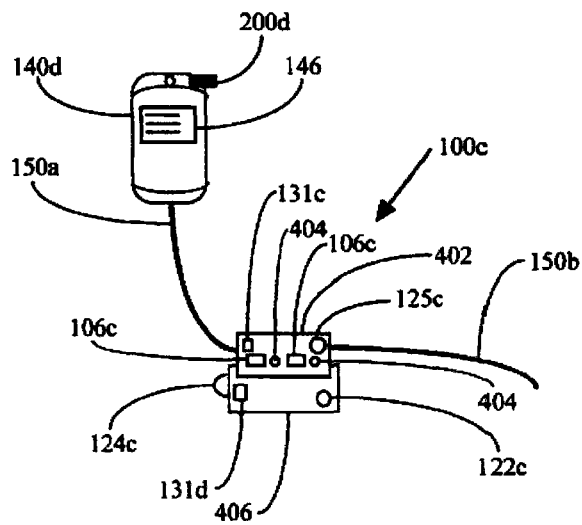
FIG. 32 is a schematic view of another pump embodiment according to the present invention.
Figure 34:
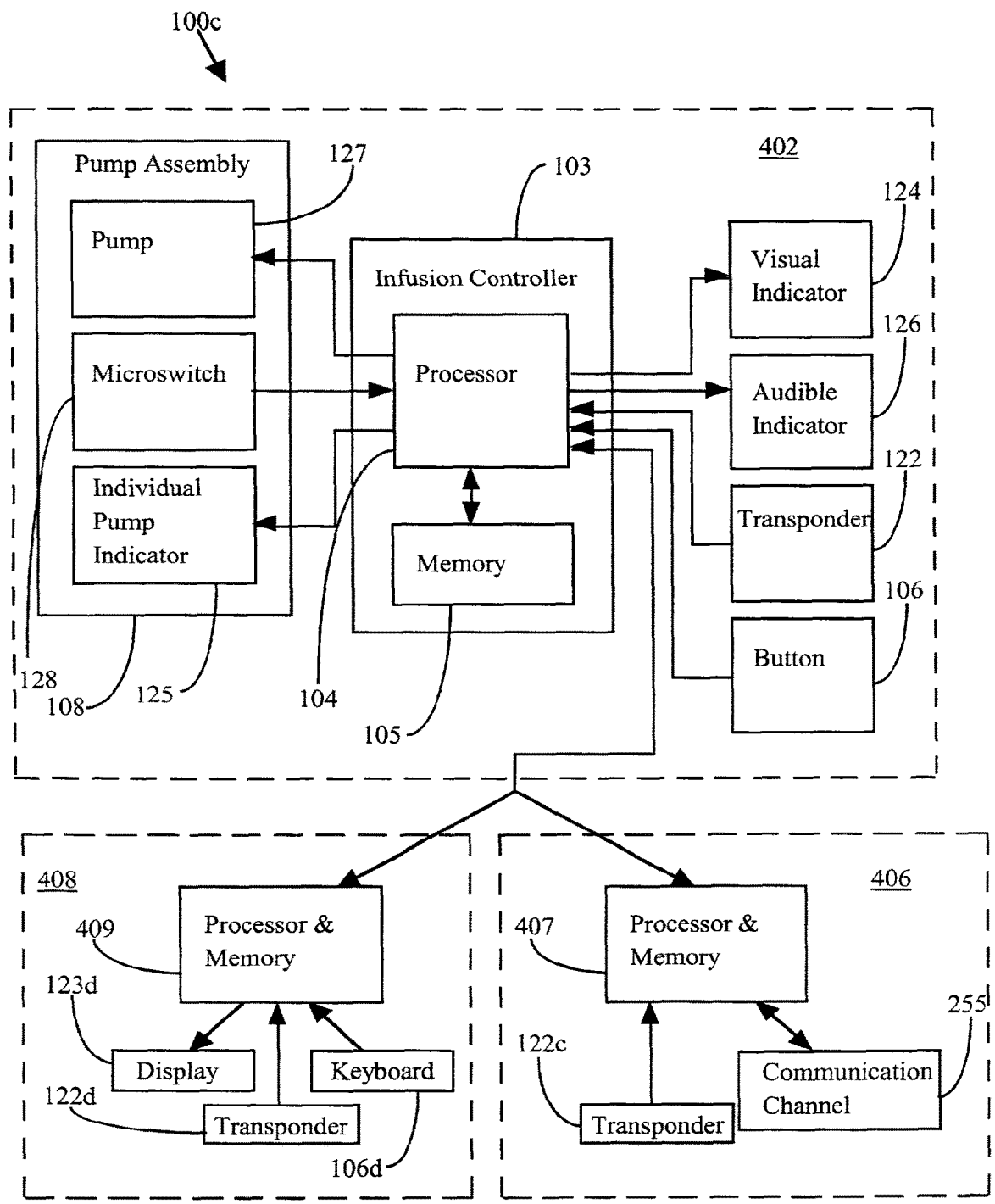
FIG. 34 is a schematic view of various components of the pump assembly of FIG. 33.

Referring also to FIG. 32, a simplified pump assembly 100*c* is illustrated which includes a pump model 402 and a communications module 406 attached thereto. Referring also to FIGS. 17 and 34, modules 402 and 406 include many of the components that were included in pump 100, similar components identified by similar numbers. Most of the components of FIG. 34 are similar to the components of FIG. 17 and therefore will not be explained again here in detail.

One distinction is that combined modules 402 and 406 include only a single pump assembly 108. Another distinction is that modules 402 and 406 do not include a display and also have an abbreviated physician input device comprising one or a small number of buttons 106. This limited user interface prevents a physician from using pump 100 to alter and monitor delivery parameters with the exception of emergency function (e.g., stop and start) that may be facilitated via buttons 106. In this case controller 260 is used to monitor and control via channel 255 and/or transponder 122*c*. In one embodiment module 406 is an integral part of module 402.

It has been recognized that there may be instances wherein a patient linked to a pump 100*c* may have to be transported within a facility and therefore may not always be proximate a controller 260. In these cases it would be disadvantageous if there were no way to monitor and control IV pumps 100*c* linked to the patient during transport.

Figure 33:
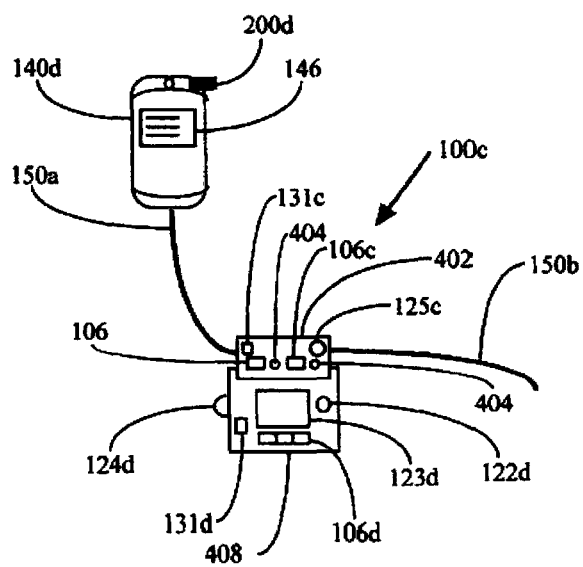
FIG. 33 is a schematic view of yet another pump embodiment according to the present invention.

To facilitate monitoring and control during transport it is contemplated that, at least in one embodiment, communication module 406 may be detachable from pump module 402 and a transport controller module 408 may be attachable in its stead. To this end, communication module 406 includes a communication processor 407, a channel 255 and a transponder 122*c* that are separable from pump module 402. Referring still to FIG. 34 and also to FIG. 33, a transponder control module 408 includes a control processor 409, a display 123*d*, a control keyboard 106*d* and a control transponder 122*d*. It is contemplated that module 408 may be programmed to support virtually any of the functionality described above with respect to controller 260. It is also contemplated after transport, modules 408 would again be replaced by modules 406 and a controller 260 could then again be used to control and monitor.

Referring again to FIG. 34, in yet one other embodiment processor and memory 407 may be folded into processor 104 and memory 105 so module 406 only includes transponder 122*c* and/or channel 255. In addition, where module 406 is integral with module 402, an attachable control module 408 may simply include a display 123*d* and enhanced control keyboard 106*d* to facilitate control and monitoring.

H. Physician Alerts and Charting with Staged Medication Dosing

Referring again to FIG. 26, a medication 236 in an IV bag (e.g., 140*a*) can have an initial dose to be delivered to patient 12 and one or more additional staged doses, e.g. start at 30 mL/hr and increase the rate by 30 mL/hr every hour up to a maximum amount of 150 mL/hr. When pump 100*a* is programmed with a multi-step prescribed dosage 240 (see FIG. 6), it is common practice for pump 100*a* to present an audible alert prior to the time when a change is to occur. This alert is referred to as a "nurse callback". The physician, when hearing the alert, returns to pump 100*a* to press a key on keyboard 106 to accept the next scheduled dosing alteration. This practice requires the status of pump 100*a* and patient 12 to be verified prior to affecting the change. While this procedure is good practice, the procedure irritates patients who are awake with extra audible alerts, increasing their general discomfort and anxiety.

To assist physicians in verifying pump operation and patient condition without the callback alert being presented, referring again to FIG. 3, physician identification device 40 can be programmed to issue an alert via speaker 45 or indicator 46 a few minutes prior to the callback alert being activated by pump 100*a*. In some circumstances speaker 45 can present a synthesized voice further indicting which patient is to be attended to or indicator 46 can be in the form of an LCD or other display showing the patient's name or room number.

Identification device 40 can be programmed using three different methods to present alerts prior to pump 100*a* issuing a nurse callback alert. First, pump 100*a* can be manually programmed with a series of dosing steps using one or more of buttons 106. As a convenience, commonly employed staged dosing steps can be preprogrammed in pump 100*a* for manual selection. The dosing steps can also be read by pump 100*a* from tag 200. When pump 100*a* is started, the pump 100*a* transmits the times of one or more nurse callbacks, via transponder 122 or via channel 255, to identification device 40. Identification device 40 then uses an on board clock to determine when the first callback time will occur and presents an alert to the physician prior to the callback time.

The second method of programming identification device 40 with callback times, is for device 40 to read tag memory contents 220 directly and record the callback times in device memory contents 60. To further determine when a callback is due, identification device 40 can monitor when pump 100*a* is started via transponder 122 or channel 255 or in response to pressing button 44.

The third method of programming identification device 40 to issue callback alerts is to use controller 260 to transfer the callback times or time intervals for a medication to the device 40 via transponder 274.

Controller 260 can also be programmed to monitor when a medication dosage is to be changed and can then issue a message to a paging service via network 272 or other communication channel (e.g., e-mail, etc.) for this purpose. The pager message will indicate the patient and medication that is to be changed. The message can be sent to a pager assigned to a physician for the healthcare unit the patient is in or to a pager assigned to the physician who provided information 220 to pump 100*a* or controller 260, e.g. a pager number stored in memory contents 60 of physician identification device 40.

When IV pump 100*a* is programmed with a multi-step prescribed dosage 240 and a physician attempts to manually change the dose via pump buttons 106 significantly earlier than the time of the next prescribed stage, pump 100*a* can present an alert using display 123, audible indicator 126, or visual indicator 124. As an example a change may be significantly early if less than 75% of the of the time or dose of the current stage has been delivered.

Figure 44:
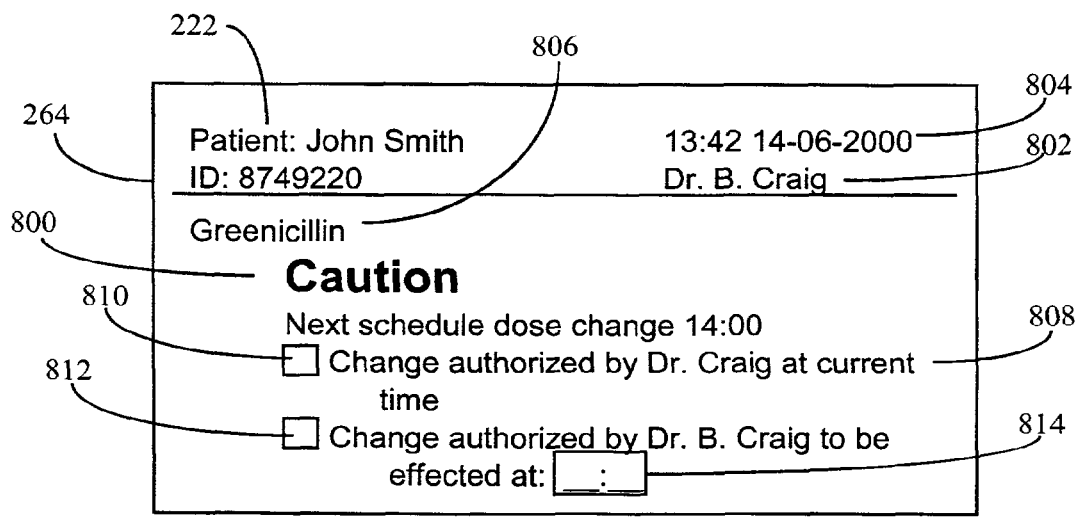
FIGS. 44-46 are exemplary screen shots according to one embodiment of the present invention.

Referring now to FIG. 44, when a physician attempts to manually change a dose via controller 260 significantly earlier than the time of the next prescribed stage change, controller 260 can present a warning screen shot 800 via display 264 or another warning device. Exemplary screen shot 800 includes information related to the patient such as name 21 and ID number 264. In addition, shot 800 identifies the physician attempting to make the change 802 and the current time 804. The medicant for which the change is to be made is identified 806 and the time of the next scheduled dose change 808 is provided. Moreover, two selections are also provided to the physician. A first icon 810 (e.g., a check box) is provided that may be selected to accept the dose change immediately. A second icon 812 (e.g., another check box) is provided that may be selected to select some time in the future at which to affect the dose change. Each one of the icon selections clearly indicates that the physician (e.g., Dr. Craig in the illustration) associated with the controller 260 is authorizing the change. Where icon 812 is selected, controller 260 requires a time to be entered in a box 814 indicating the time to alter. This process creates a complete set of physician notes and an audit trail of any changes without any or with only minimal data entry. The notes created can be printed via a printer (not illustrated) that is accessible to controller 260 or the notes can be transferred for storage to a database that is part of network 272.

I. Physician Charting Medication Titration

Referring again to FIGS. 6, 26 and 28, a medication in an IV bag 140 can have a titration standing order 245 which is usable by an attending physician to modify the dose being delivered in response to a patient's vital signs, laboratory results, or condition. When a medication is being infused via a pump 100*a* and monitored by controller 260, any changes to the dose that pump 100*a* is delivering are monitored. When the changes are made at pump 100*a*. Requests can be presented via controller 260 for the physician to identify himself and enter a note in an electronic chart regarding the change. Likewise, when the changes are made via controller 260, the physician can be requested to enter a note in the electronic chart. In this case, the change can be sent to pump 100*a* either after the note has been entered or before.

Figure 45:
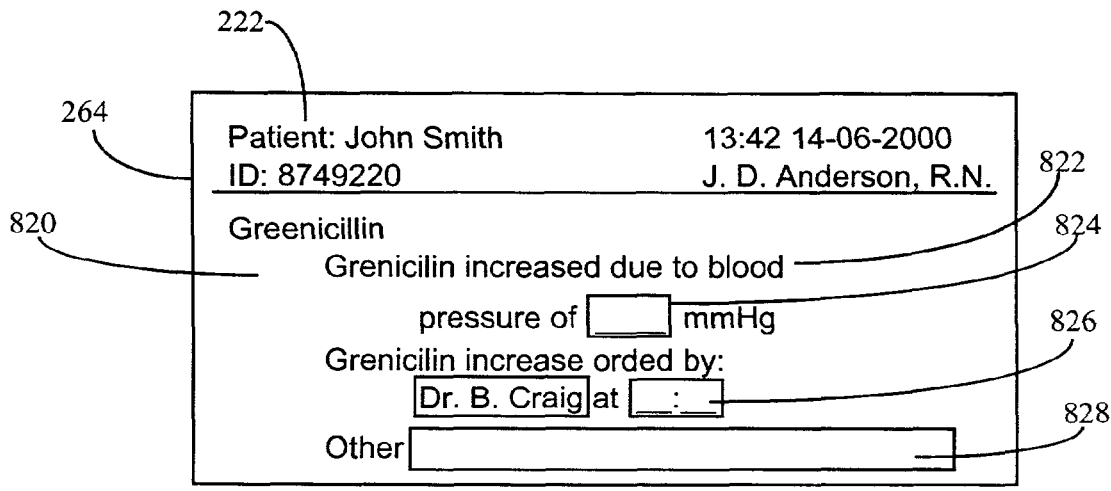

To assist the physician, it is contemplated that the note can be preformatted in part referencing the titration order 245 for the medication related to the pump for which the change is being made. For example, in FIG. 28, Greenicillin can be increased when the patient's blood pressure rises above 150 mmHg. Referring also to FIG. 45, when a physician uses softkey 306 to increase the dose of Greenicillin, controller 260 can present screen shot 820 on display 264. Where controller 260 monitors blood pressure, controller 260 can determine when Greenicillin infusion rate should be increased and provide an indication thereof to controller 260. In this case, note 822 is automatically created by controller 260 indicating that when the dose is increased, the increase is due to an increase in the patient's blood pressure above 150. The physician only needs to enter the current blood pressure in box 824 and a time in box 826 to complete this entry for the patient's chart.

Referring again to FIG. 26, in some rooms the patient is connected to one or more physiological monitors 830 with displays 831 and optional indicators 834 having a purpose similar to indicator 124*a* on pump 100*a*. Controller 260 in this case may be in communication with monitor 830 via a communication channel 255*c* or via wireless communication. When channel 255*c* is a wired connection, monitor 830 is automatically associated with the same patient as controller 260. When communication is via a wireless link, monitor 830 can be associated with a patient by equipping monitor 830 with a transponder 836 similar to pump transponder 122. Transponder 836 can obtain a portion of memory contents 20 from patient identification device 10 which can be used to associate monitor 830 with patient 12.

Here, where controller 260 broadcasts a message asking all devices (e.g., pumps 100, monitor 830, and other treatment devices) to identify themselves, each device transfers a communication address that controller 260 can use to obtain pump status or the patient's physiologic measurements. Alternately, physician identification device 40 can be used to read a tag, similar to tag 132, affixed to monitor 830. The tag would include a wireless channel address used by controller 260 to address monitor 830 to receive the physiologic measurements for the patient. Indicator 834 can be activated under circumstances when it is desirable to visually identify that monitor 830 is addressed by controller 260, (e.g., when controller 260 is receiving information from monitor 830 or sending information to monitor 830). By visually identifying monitor 830 a physician can verify that the addressed monitor is in fact monitoring the patient associated with controller 260. In some instances indicator 834 can be replaced by a message or graphic image presented on a display 831.

When controller 260 is associated with patient physiological monitors (e.g., 830), controller 260 can obtain patient 12's blood pressure sensed by a transducer 832 from monitor 830. In this case, controller 260 can insert the current blood pressure in box 824 in FIG. 45 for the physician to accept.

When the dose of Greenicillin is increased but the blood pressure has not gone above the limit (150 mHg), controller 260 may be programmed to present a warning message indicating that Greenicillin should not be increased. The physician can then authorize the increase independent of the titration requirements by entering the time in box 826. Alternately, the physician can enter a text note in an "Other" box 828.

If none of the notes or fields have an entry placed in them within a period of time (e.g. 5 minutes), an audit note can be created by controller 260 for entry into the patient's chart or a remote database. The audit note in this case may indicate the dose change, time and, when changed at the controller, who made the change. Similarly to the above process for staged dose changes, this process creates a complete set of physician notes and an audit trail of any changes with only minimal data entry.

When titration of a medication is based on a change in a patient's laboratory results, other preformatted notes may be presented on controller display 264 based upon whether the dose is being increased or decreased and the nature of the titration order, (e.g., when the dose is to be increased in relationship to the patient's urine analysis and the dose is increased, the note can be formatted to allow the physician to enter the urine analysis value(s)). When controller 260 is attached to network 272, controller 260 may be programmed to retrieve urine analysis results automatically and thereby further format the note or to alert that the dosage should not be increased.

Whenever controller 260 determines that an infusion rate change should be made, in addition to indicating the change locally via display 264 or some other indicator, controller 260 may also provide a networked indication similar to a call back described above so that if there is no physician proximate the controller 260 associated with a patient, the change request does not go unnoticed.

Where controller 260 indicates that an infusion rate change should be made but the physician associated with controller 260 is not around, a second physician may make the change (if authorized) and either the controller 260 or a pump and the second physician's badge may record the change and the second physician's identification for subsequent record keeping.

Similarly, when a dose is to be changed relative to the physician's perception of the patient's condition, other notes reflective of this titration order can be presented on controller display 264.

J. Medication Route

Medication that is in IV bag 140 may be specified for delivery via a specific route 569 (see FIG. 6) such as, for instance, intravenous delivery or epidural delivery. While the term IV bag has been used and commonly indicates a fluid bag for intravenous delivery or fluids, medication for other delivery routes can be packaged in containers that are similar to an IV bag. Packaging medications that are to be delivered via different routes in similar appearing packaging can cause serious consequences if the physician assumes they can all be delivered together or via the same route.

Figure 46:
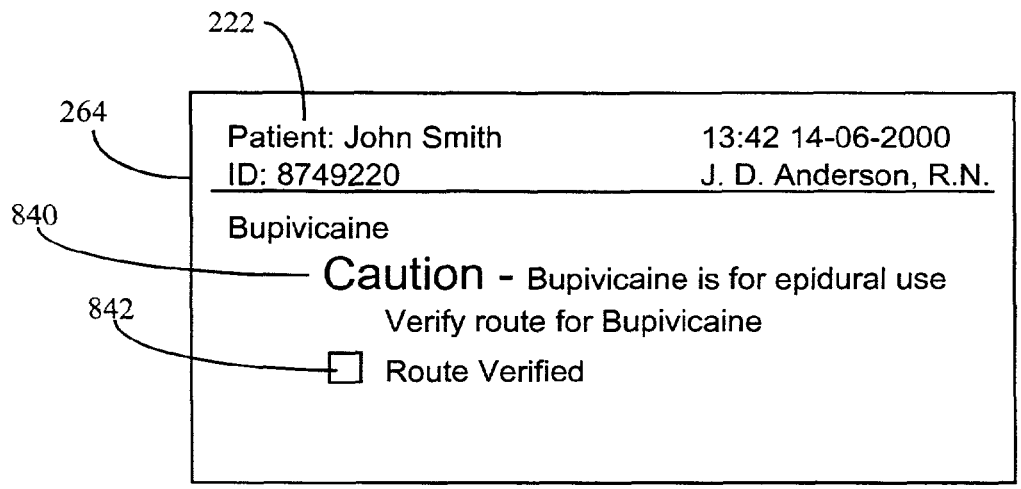

To prevent this, when medication is to be given to a patient and is to be delivered via an unusual route (e.g., any non-intravenous route), special questions and instructions can be posed via the system interface devices that make sure the physician is aware of special conditions and/or circumstances. For example, when controller 260 receives dispensed IV medication information 230, controller 260 can check route 569 for a non-standard delivery type. Referring to FIGS. 26 and 46, when a non-standard route is detected, controller 260 can present screen shot 840 or another message as appropriate for the specific medication. The physician can be requested to verify the delivery route and enter a confirmation check mark in a verification box 842.

Similar checks can be performed to determine that an IV bag containing a blood product is delivered via a pump that is compatible with the delivery the blood product. This is important as some pumps can damage the cellular structure of certain blood products. The check can be performed manually or by controller 260 receiving a code identifying the type of pump as part of pump status 291 or pump identification number 130 and comparing it with blood product information which is similar to dispensed IV medication information 230.

K. Adding Medication to IV Bag

Figure 47:
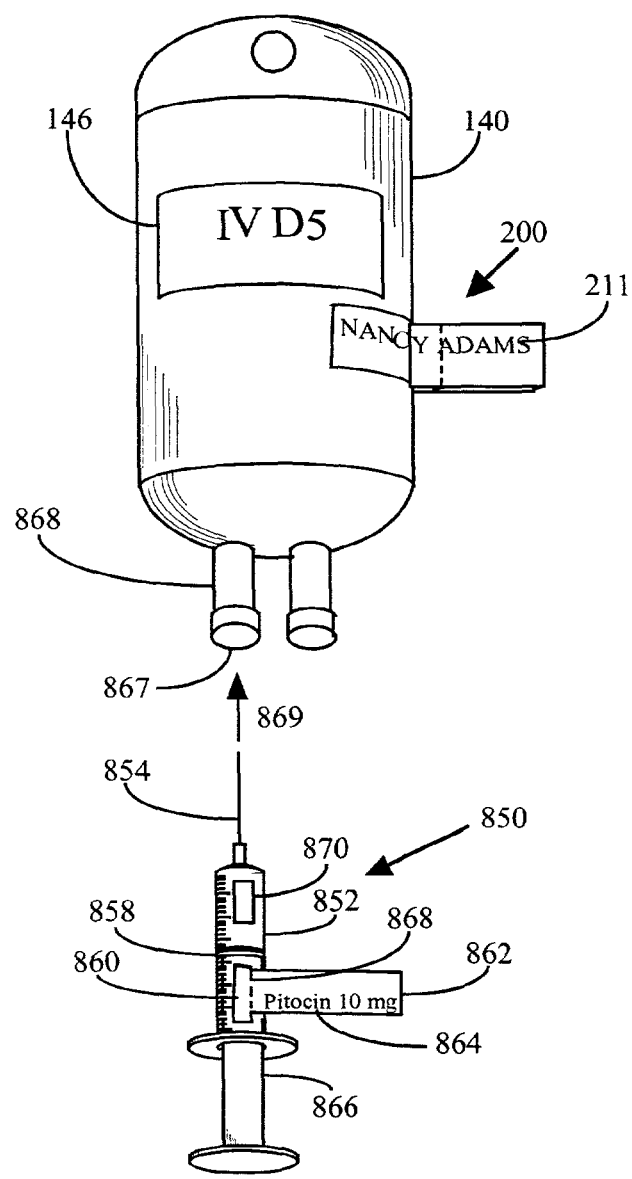
FIG. 47 is a schematic diagram of an IV bag and syringe assembly useable with the present invention.

Referring again to FIG. 16, in some instances it may be desirable for a physician to add a medication to an IV bag 140 that is already delivering or will be used to deliver fluids to a patient. Frequently, medication to be added to an IV bag 140 is dispensed into a syringe 850 (see FIG. 47). Syringe 850 includes a main body 852, a needle 854 and a plunger 856 with hydraulic seal 858. Syringe 850 includes a text label 860 affixed to it, allowing a physician to read the name of medication in syringe 850. Extended from label 860 is adhesive label 862 with text 864 and or a bar code that also identifies the medication in syringe 850. Label 862 is designed to be pulled apart from label 860 along perforations 866 in a manner similar to the labels described above.

The medication in syringe 850 is added to IV bag 140 by removing a protective cap 867 and inserting needle 854 into access port 868 following direction 869. Syringe plunger 856 is then pressed forcing the contents of syringe 685 into IV bag 140. Label 862 can be removed, a backing paper (not shown) separated from label 862 and label 862 can be adhered to IV bag 140 to clearly indicate the medication added to bag 140.

With care, this practice can be safe and efficient, but too often in a busy care center mistakes are made. To increase the safety of the procedure described above, memory device 870 can be attached to body 852 or syringe 850. Memory device 870 is similar to memory device 201 and the contents of memory device 870 are generally similar to memory contents 220 (see FIG. 6). In general, similar items in memory device 870 will be referred to by the same numbers as those in memory contents 220 with an apostrophe added. For instance, medication name 236' is used to identify the medication in syringe 850. Memory device 870 can be read by communication device 42 or an alternate sensor on physician identification device 40.

Prior to injecting the contents of syringe 850 into IV bag 140, the physician can use identification device 40 to read the memory of device 870 and memory device 201. When target patient information 222 and 222' is available, identification device 40 can compare the information to determine if the medication in the syringe is for the same patient as IV bag 140 was dispensed for. If not, an alert is presented to a physician, (e.g., via speaker 45 or other device for this purpose). In some circumstances a check may be performed to determine if the medication in syringe 200 is compatible with the fluid in IV bag 140, (e.g., one medicant may cause another medicant to precipitate out of the fluid), if the patient associated with bag 140 is allergic to the medicant in syringe 850, if the medicant in bag 140 and syringe 850 are incompatible, etc. When there is an incompatible situation, an alert can be presented to a physician, (e.g., via speaker 45).

Whether the above comparisons were made or not (e.g. the IV bag is a floor stock item and doesn't have selected patient information 222), identification device 40 may also transfer portions of memory contents 220' from memory device 870 to memory contents 220 of device 200. By transferring this information, prescribed dosage 240' for medication in syringe 850 can be transferred to memory 201. In addition, identification device 40 may also be programmed to transfer portions of updated memory contents 220 (composed of the original contents plus portions of memory contents 220') to IV pump 100 or to controller 260. This allows prescribed dosage 240' to be used in conjunction with quantity 234 to determine the concentration of medication in IV bag 140 so a corresponding pump can be programmed to pump the amount of fluid required to meet the physician's order.

Identification device 40 can also determine the time interval between reading memory contents 220' and 220 and may enforce timing rules similar to the rules described above. For instance, when a time interval between readings exceeds a limit (e.g. 5 minutes), an alert may be presented by speaker 45 or another device. This timing rule will prevent the physician from accidentally injecting the syringe contents into a bag for the wrong patient.

If identification device 40 reads memory contents 220', but not memory contents 220, when device 40 communicates with pump 100 or controller 260 an alert that a possible error has occurred can be generated by any of pump 100, controller 260 or device 40. When pump 100 has only a single line attached to it, pump controller 260 may be able to use memory contents 220'. However, when there is more than one line attached to pump 100 or controller 260 is monitoring more than one pump, memory contents 220' cannot be used to control a dosage delivered by pump 100 without being provided with memory contents 220 or pump identification 130 and the IV line number.

In an alternate embodiment memory contents 220' can be read by transponder 122 of IV pump 100 or sensor 268 of controller 260. Pump 100 and controller 260, when already associated with a patient, can determine if syringe 850 is prescribed for the associated patient by comparing target patient information 222' with the associated patient. The physician can select a pump and/or pump line through a manual selection process by using a display 123 and buttons 106 or display 264 and buttons 266. Either pump 100 or controller 260 can then use memory contents 220 previously recorded and memory contents 220' to set or alter the pump delivery parameters.

The verification process described above in the context of syringe 850 may be performed by a pharmacist prior to dispensing an IV bag. For instance, pharmacist's at a facility, like physicians, may each have a badge 40 (see FIG. 3) that can verify that medicant in a syringe should be added to an IV bag, the timing of the addition, etc., and which can create a record of the addition including time, pharmacist ID number, target patient information, etc., and which may also update information stored in tag memory 201 to reflect verification time and the content of the new bag solution prior to release.

In some situations memory device 870 can be a part of label 862, allowing memory device 870 to be removed from syringe 850 and placed on IV bag 140. When memory devices 201 and 870 are RFID tags and are placed in the presence of a strong enough field both can be read nearly at the same time. When a weaker field is present, (e.g., from identification device 40), the physician will have to perform two separate reads to obtain information from both devices.

K. Server Based Embodiments

Referring again to FIGS. 6 and 26, it should be noted that titration order 245 and other components of dispensed IV medication information 230 can be obtained by controller 260 via network 272. Memory contents 220, instead of including information 230, can be restricted to prescription order number 246 or another number used to identify the medication treatment to be given. Controller 260, upon receiving prescription order number 246, can access the remaining components of dispensed IV medication information 230 via network 272 from a hospital computer system 630 and database 632.

L. Ensuring Audit of Changes to Pump Operation

Referring to FIG. 26, when pump 100 is in communication with controller 260 and any change is made to pump operation (new rate, duration, IV line 150 removed from pump, etc), a pump status 291 message may be sent to controller 260 indicating the change. When a change is made, it is desirable to have the physician that facilitates the change identify himself to controller 260 so that an audit trail can be maintained for each change. The physician, by gaining access to controller 260 (e.g. password entry or by using physician identity device 40 to provide a wireless identification password communication via communication device 42), within a period of time (e.g. within 2 minutes) relative to the attempt to make a change may be associated with the change. The physician can be prompted for confirmation that he made the change and given an opportunity to provide a reason for the change (e.g., new physician's order). Instead of the controller based prompt, the prompt may be provided to the physician via the physician's badge 40 and, where the physician authorizes a change via her badge 40, the change may be noted by the controller 260 and then be performed.

In the event that a physician does not use controller 260 within the above mentioned period of time, controller 260 can present an audible alert requesting the physician to confirm the change. If a different physician responds to the alert than the one who made the change, the different physician may be limited to indicating he is only responding to the alert and that another physician actually made the change. Should this type of unconfirmed activity occur frequently, administrative management can receive messages to this effect via network 272.

M. Discontinued IV Medication

Referring again to FIG. 26, when an IV bag 140 is discontinued at controller 260 (e.g., stopping a corresponding infusion pump 100 or pump unit 108), controller 260 may monitor communication channel 255 for a status message indicating that the IV line 150 has been removed from pump 100 or pump unit 108 or a message indicating that pump 100 is being turned off. When controller 260 does not receive such a message within a period of time (e.g., 3 minutes), controller 260 may activate an audible alert indicating that the IV medication is still attached to pump 100 or pump unit 108 and might be administered again incorrectly to the patient. The physician can reset the alert by pressing a button 266 or by removing the discontinued IV line from pump 100 or pump unit 108 or by turning pump 100 off.

Similarly, when a pump is turned off or all medicants are removed from a pump, the change can be reported to the controller which may either disassociate from the pump or request confirmation that disassociation should be performed.

N. Pump Activation Without Communication With Controller 260

Referring to FIG. 26, when pump 100 and controller 260 are to be used together either pump 100 or controller 260 can monitor for a situation where this is not the case. For example pump 100, when running, can detect that a controller 260 is addressing or communicating with it using communication channel 255. If pump 100 detects that it is not in communication with controller 260 or has lost communication for a period of time (assuming it had been in communication previously), pump 100 may present an audible alert. A physician responding to the alert can determine that pump 100 has not been associated with controller 260 as previously described or that controller 260 is no longer functioning properly and should be replaced.

Alternatively, when pump 100 has not been associated with a specific controller 260, pump 100 may be programmed to send a general error signal using communications channel 257, indicating that no controller is monitoring its activity. The general error signal can be detected by any controller 260 monitoring communication channel 255. When any controller 260 receives this signal, the receiving controller may activate audible or visual alerts. A physician responding to this alert can determine that the pump has not been properly associated with a patient or controller 260 and correct this situation. Similarly, pumps and controllers may be programmed to periodically communicate with an associated patient identification device 10 to make sure a patient remains present during infusion.

It should be understood that the methods and apparatuses described above are only exemplary and do not limit the scope of the invention, and that various modifications could be made by those skilled in the art that would fall under the scope of the invention. For example, while an exemplary IV bag has been discussed in the above embodiments, it should be understood that inventions apply to other types of fluid or gas containers, e.g. blood bags, syringe injectors, or gas cartridges.

In addition, while some embodiments described above may not teach activation of indicators when one or more devices are communicating, it should be appreciated that such indicating is contemplated in all embodiments.

In addition, while a handful of different comparisons are described above that facilitate safe and effective use of medicants, other types are also contemplated. For instance, various advances in the study of human genes have led to the realization that certain medicants have minimal if any beneficial value when used by specific patients. Thus, where genomic information is accessible by a delivery system, as in the case of allergy identification, genomic information comparison may be facilitated to ensure that worthless medication is not performed on patients.

Thus, it should be appreciated that a comprehensive delivery system for use in a medical facility has been described which has been configured to reduce facility errors, provide peace of mind to facility patients and physicians alike, to automate record keeping and to increase overall facility security. To this end, patient, physician medicant and equipment identification devices including processors and suitable medicants are delivered to patients in a timely fashion by comparing various information types associated with each system component and either enabling delivery or performing some other health safety function.

To apprise the public of the scope of this invention, the following claims are made.

What is claimed is:

1. A system used to deliver medication to a patient comprising:
    a computer storing prescription information, including information that is specific to a first patient;
    said computer having a network connection, receiving first information indicative of a first machine readable identifier corresponding to a patient identification that is attached to a limb of a patient, receiving second information indicative of a second machine readable identifier from a medication dispensing container with medication to be administered to the patient, and receiving third information corresponding to a medical device identification that is representative of a specific one medical device that is associated with delivery of medication to a patient and is indicative of a third machine readable identifier from the specific one medical device;
    said computer operating to compare stored prescription data to at least said first and second information, and to determine if information indicative of the use of the medication is authorized to be sent, and if said information indicative of the use of the medication is authorized to be sent, then sending said information indicative of the use of the medication to said specific one medical device using the medical device identification to deliver the medication to the patient;
    wherein said medical device is a medical pump for pumping medication; and
    wherein said system monitors operation of said medical pump to deliver said medication in a specified dosage.

2. A system as in claim 1, wherein said computer sends said information indicative of the use of the medication at a current time.

3. The system as in claim 1, further comprising said medical device that includes a machine readable identifier thereon.

4. The system as in claim 1, wherein the network communication communicates using wireless communication.

5. The system as in claim 1, wherein said computer controls said operation to deliver said medicant also after receiving an identification from a badge of a medical professional.

6. The system as in claim 1, wherein said computer stores and uses information specific to the patient includes drugs to which the patient is allergic.

7. The system as in claim 1, wherein said computer disables information on said container from being used more than once.

8. The system as in claim 1, wherein said computer stores and uses information about drugs which are genomically incompatible with the patient.

9. The system of claim 1, wherein said computer further receives time data associated with the first information and the second information, and wherein said computer further operates to compare the time data associated with the first information with the time data associated with the second information, and if said time data are within a predetermined threshold period of each other, then sends said information indicative of the use of the medication to said specific one medical device.

10. The system of claim 1, wherein said computer is operable to determine if said information indicative of the use of the medication is not authorized to be sent, and if not, said computer then sending to an indicating device a message indicating said medication is not to be given to said patient.

11. The system of claim 10, wherein said indicating device is used to read and transmit said first, second, and third machine readable identifiers and said indicating device indicating the message using one of a visual indicator, a visual display, and an audio indicator.

12. A system used to deliver a prescribed amount of medication to a patient, comprising
a medical device having a first machine readable identifier;
a patient identification bracelet having a second identifier that identifies a patient identification and that is attached to a limb of a patient;
a medication container, having a third identifier indicative of contents of said medication container that is used to dispense medication to the patient;
a wireless network;
a wireless reader device that reads each of said first, second and third identifiers, and communicates information indicative of each of said first, second and third identifiers over said wireless network; and
a central computer, receiving said information indicative of each of said first, second and third identifiers that were transmitted over the wireless network, said computer operating to compare stored prescription data to at least said second identifier and said third identifier, and to determine if at least a portion of the stored prescription data related to the medication of said third indicator is authorized to be sent, and when the determination indicates that said third indicator is authorized sending said at least a portion of stored prescription data to said medical device to control operation of said medical device to deliver said medication using the information obtained from the first identifier.

13. The system as in claim 12, wherein said computer determines whether the prescription data is authorized at a current time, and if so, sends said portion at the current time.

14. A system as in claim 12, wherein said medical device is a medical pump for pumping medication.

15. The system as in claim 12, wherein said central computer controls said operation after receiving an identification from a badge of a medical professional.

16. The system as in claim 12, wherein said computer stores and uses information specific to the patient includes drugs to which the patient is allergic.

17. The system as in claim 12, wherein said computer stores and uses information about drugs which are genomically incompatible with the patient.

18. The system as in claim 12, wherein said computer disables information on said container from being used more than once.

19. The system as in claim 12, wherein said wireless reader device has a readable screen, that shows information from said indicator.

20. The system of claim 12, wherein the wireless reader device further provides time data associated with said second and third identifiers and communicates said time data over said wireless network; and
wherein said central computer further operates to compare the time data associated with the second identifier with the time data associated with the third identifier, and if said time data are within a predetermined threshold period of each other, then sends the at least a portion of stored prescription data to said medical device.

21. The system of claim 12, wherein said computer is operable to determine that at least a portion of the stored prescription data related to the medication of said third indicator is not authorized to be sent, and if not, the computer is operable to send a message indicating said contents of the medication container are not to be given to said patient to said wireless reading device and the reading device activating an indicator selected from a visual indicator, a visual display, and an audio indicator.

22. A system used to deliver medication to a patient comprising:
a computer storing prescription information, including information that is specific to a patient;
said computer having a network connection,
(i) receiving first information indicative of a first machine readable identifier corresponding to a patient identification that is attached to a patient,
(ii) receiving second information indicative of a second machine readable identifier from a medication dispensing container with medication to be administered to said patient, and
(iii) receiving third information corresponding to a pump identification that is representative of a specific pump that is associated with delivery of a specific dosage of medication to a patient and is indicative of a third machine readable identifier from said specific pump; and
said computer operating to compare stored prescription data to at least said first and second information, and
to determine if information indicative of the use of said medication is authorized to be sent, and
when said information indicative of the use of said medication is authorized to be sent to said specific pump, then using said pump identification to send said information indicative of the use of said medication to said specific pump and to deliver said specific dosage of medication to said patient.

23. The system of claim 22, wherein said computer is configured to determine if said information indicative of the use of the medication is not authorized to be sent to said specific pump, and if not, said computer sends a message to an indicating device reflective that said medication in said medication dispensing container is not to be given to said patient.

24. The system of claim 23, wherein said indicating device is associated with a physician and indicates said message using one of a visual indicator, a visual display, and an audio indicator.

25. The system of claim 24, wherein said indicating device enables said receiving of said first, second, and third information.

26. The system of claim 25, wherein said receiving by said indicating device includes receiving a visual pattern corresponding to a bar code.

* * * * *